United States Patent
Schouten

(10) Patent No.: US 6,955,901 B2
(45) Date of Patent: Oct. 18, 2005

(54) MULTIPLEX LIGATABLE PROBE AMPLIFICATION

(75) Inventor: Johannes Petrus Schouten, Amsterdam (NL)

(73) Assignee: De Luwe Hoek Octrooien B.V., Amsterdam (NL)

( * ) Notice: Subject to any disclaimer, the term of this patent is extended or adjusted under 35 U.S.C. 154(b) by 0 days.

(21) Appl. No.: 10/218,567

(22) Filed: Aug. 15, 2002

(65) Prior Publication Data

US 2003/0108913 A1 Jun. 12, 2003

Related U.S. Application Data

(63) Continuation of application No. PCT/EP01/01739, filed on Feb. 15, 2001.

(30) Foreign Application Priority Data

Feb. 15, 2000 (EP) .............................................. 00200506

(51) Int. Cl.[7] .......................... C12P 19/34; C12Q 1/68; C07H 21/04
(52) U.S. Cl. ...................... 435/91.1; 435/91.21; 435/6; 536/23.1; 536/24.3; 536/24.33
(58) Field of Search .................. 435/6, 91.1; 536/23.1, 536/24.32, 24.33

(56) References Cited

U.S. PATENT DOCUMENTS

| | | | |
|---|---|---|---|
| 6,534,293 B1 * | 3/2003 | Barany et al. .............. | 435/91.2 |
| 6,812,005 B2 * | 11/2004 | Fan et al. ................... | 435/91.2 |
| 2003/0022182 A1 * | 1/2003 | Barany et al. ................. | 435/6 |

FOREIGN PATENT DOCUMENTS

| | | |
|---|---|---|
| WO | WO 96/15271 | 5/1996 |
| WO | WO 97/08344 | 3/1997 |
| WO | WO 97/19193 | 5/1997 |
| WO | WO 97/45559 | * 12/1997 |
| WO | WO 98/03673 | 1/1998 |
| WO | WO 98/04746 | 2/1998 |
| WO | WO 98/37230 | 8/1998 |

OTHER PUBLICATIONS

Martin Wiedmann et al, "Ligase Chain Reaction (LCR)—Overview and Applications," Cold Spring Harbor Laboratory Press, New York, Ny, vol 4, No. 4, 1994, pp. 551–564.

* cited by examiner

*Primary Examiner*—Kenneth R. Horlick
*Assistant Examiner*—Cynthia Wilder
(74) *Attorney, Agent, or Firm*—Browdy and Neimark, PLLC

(57) ABSTRACT

Described is an improved multiplex ligation-dependent amplification method for detecting the presence and quantification of at least one specific single stranded target nucleic acid sequence in a sample using a plurality of probe sets of at least two probes, each of which includes a target specific region and a non-complementary region comprising a primer binding site. The probes belonging to the same set are ligated together when hybridised to the target nucleic acid sequence and amplified by a suitable primer set. By using a femtomolar amount of the probes a large number of different probe sets can be used to simultaneously detect and quantify a corresponding large number of target sequences with high specificity.

35 Claims, 31 Drawing Sheets

FIGURE 1 : MLPA : Multiplex Ligatable Probe Amplification.

Application 1 : Multiplex Single Nucleotide Polymorphism analysis.

Genomic DNA sequences :

Strain V :   ATTGTCTGAAGCACAATATATTCTGTTGCGCCTGGGATTT
Strain W :   ATTGTCTGAAGCACAATATTTTCTGTTGCGCCTGGGATTT

Sequence D (20 nucl.)    SNP site 1    Sequence E (20 nucl.)
    Including SNP1 site                                  Starts next to SNP 1 site Strain V :   CCTGTATTGATAGGAGTTACAGAGCATGCTGCATATGCTC
Strain W :   CCTGTATTGATAGGAGTTAAAGAGCATGCTGCATATGCTC

Sequence F (20 nucl.)    SNP site 2    Sequence G (20 nucl.)
    Including SNP2 site                                  Starts next to SNP 2 site

Probes for SNP 1 :

Probe B1                                         Probe B2
————————┼————————ATA     ————————┼┼————————ATT PCR sequence   Sequence D        PCR sequence     Sequence D
tag Y (20 nucl.)                            tag Y
                                                                        4 nucleotides stuffer Probe A1
TTC————————┼————————————————┼————————

Sequence E     100 nucleotides stuffer     PCR sequence
                                                     tag X' (20 nucl.)

Probes for SNP 2 :

Probe B3                                       Probe B4
————————┼————————TAC     ————————┼┼————————TAA PCR sequence   Sequence F        PCR sequence     Sequence F
tag Y                                      tag Y
                                                                         4 nucleotides stuffer Probe A2
AGA————————┼————————————————┼————————

Sequence G     110 nucleotides stuffer     PCR sequence tag X'

Figure 1, part 2.
Annealing of probes to denatured chromosomal DNA of strain V, and Ligation of probes :

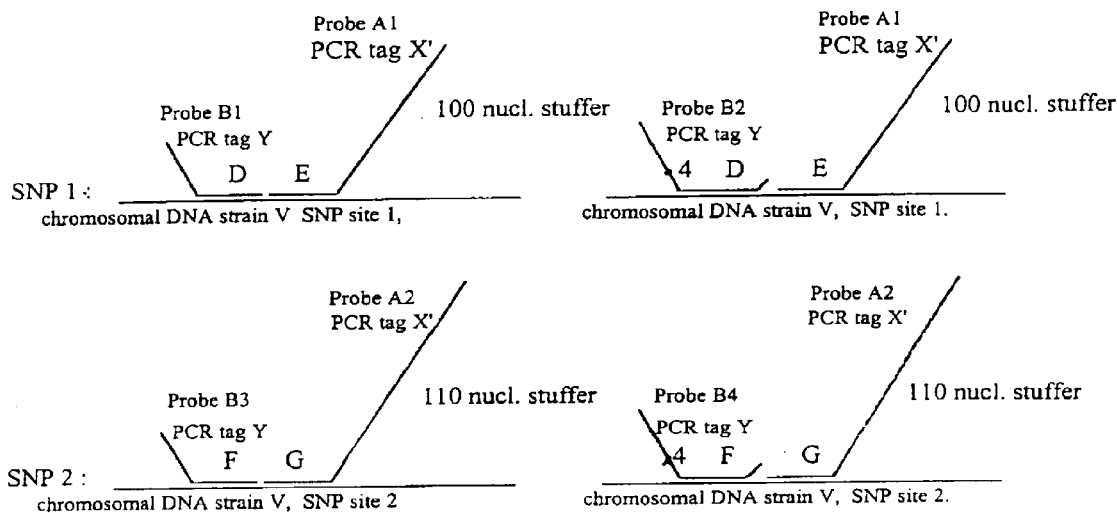

Ligation products with DNA of strains V and W used as ligation template :

| Strain | SNP | Probes    | Relative amount | Length of amplification product with primers X and Y | |
|--------|-----|-----------|-----------------|------------------------------------------------------|---|
| V      | 1   | A1 + B1   | Large           | Y + D + E + 100 − X                                  | = 180 bp. |
|        | 1   | A1 + B2   | Small           | Y + 4 + D + E + 100 + X                              | = 184 bp. |
|        | 2   | A2 + B3   | Large           | Y + F + G + 110 + X                                  | = 190 bp. |
|        | 2   | A2 + B4   | Small           | Y + 4 + F + G + 110 + X                              | = 194 bp. |

| Strain | SNP | Probes    | Relative amount | Length of amplification product with primers X and Y | |
|--------|-----|-----------|-----------------|------------------------------------------------------|---|
| W      | 1   | A1 + B1   | Small           | Y + D + E + 100 + X                                  | = 180 bp. |
|        | 1   | A1 + B2   | Large           | Y + 4 + D + E + 100 + X                              | = 184 bp. |
|        | 2   | A2 + B3   | Small           | Y + F + G + 110 + X                                  | = 190 bp. |
|        | 2   | A2 + B4   | Large           | Y + 4 + F + G + 110 + X                              | = 194 bp. |

Sequencing type gel : DNA from strain V as ligation template : 

DNA from strain W as ligation template : 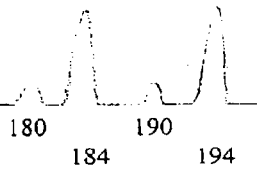

180    190
184    194

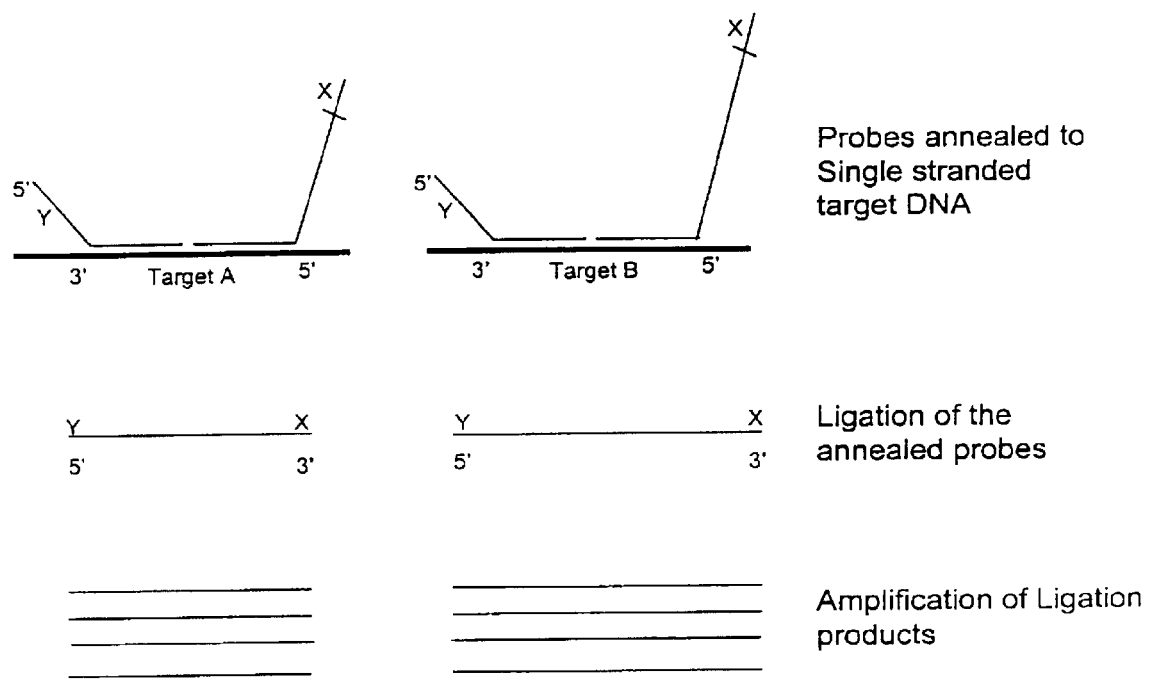
Figure 2: Graphic Outline of the MLPA technique

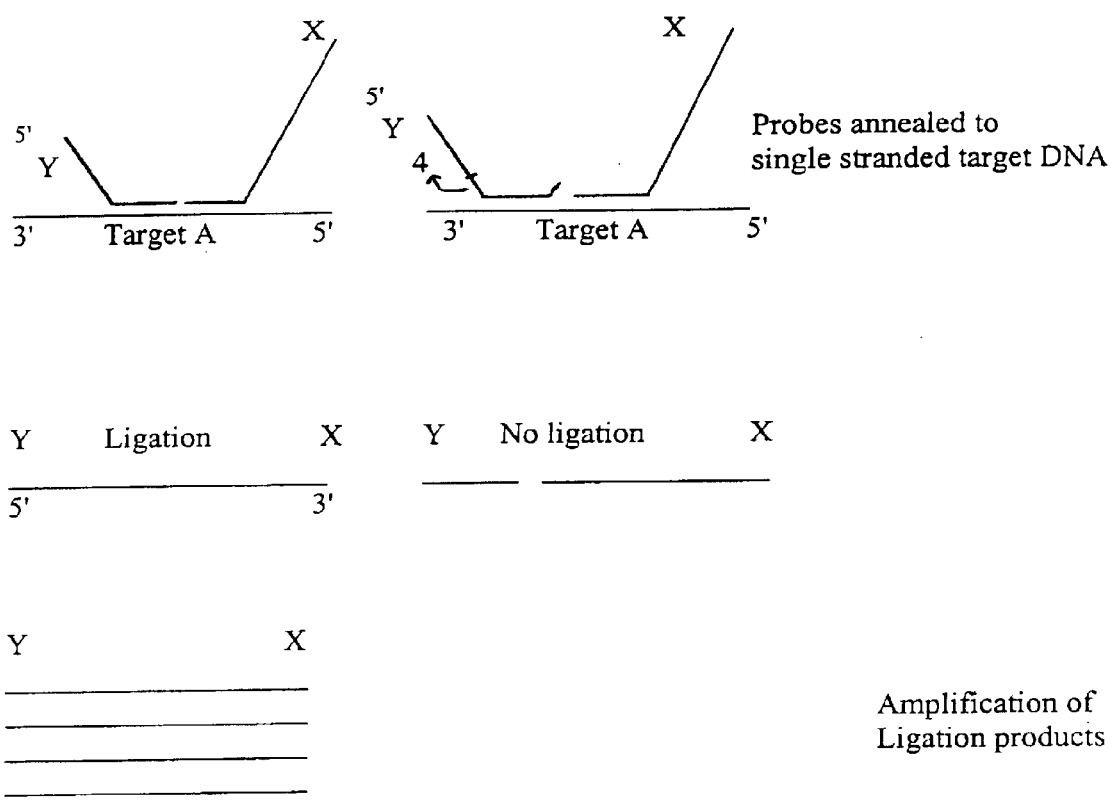
FIGURE 3 : Graphic outline of the MLPA invention for mutation detection.

FIGURE 4 : Graphic outline of a M13 clone used to prepare long Probes.
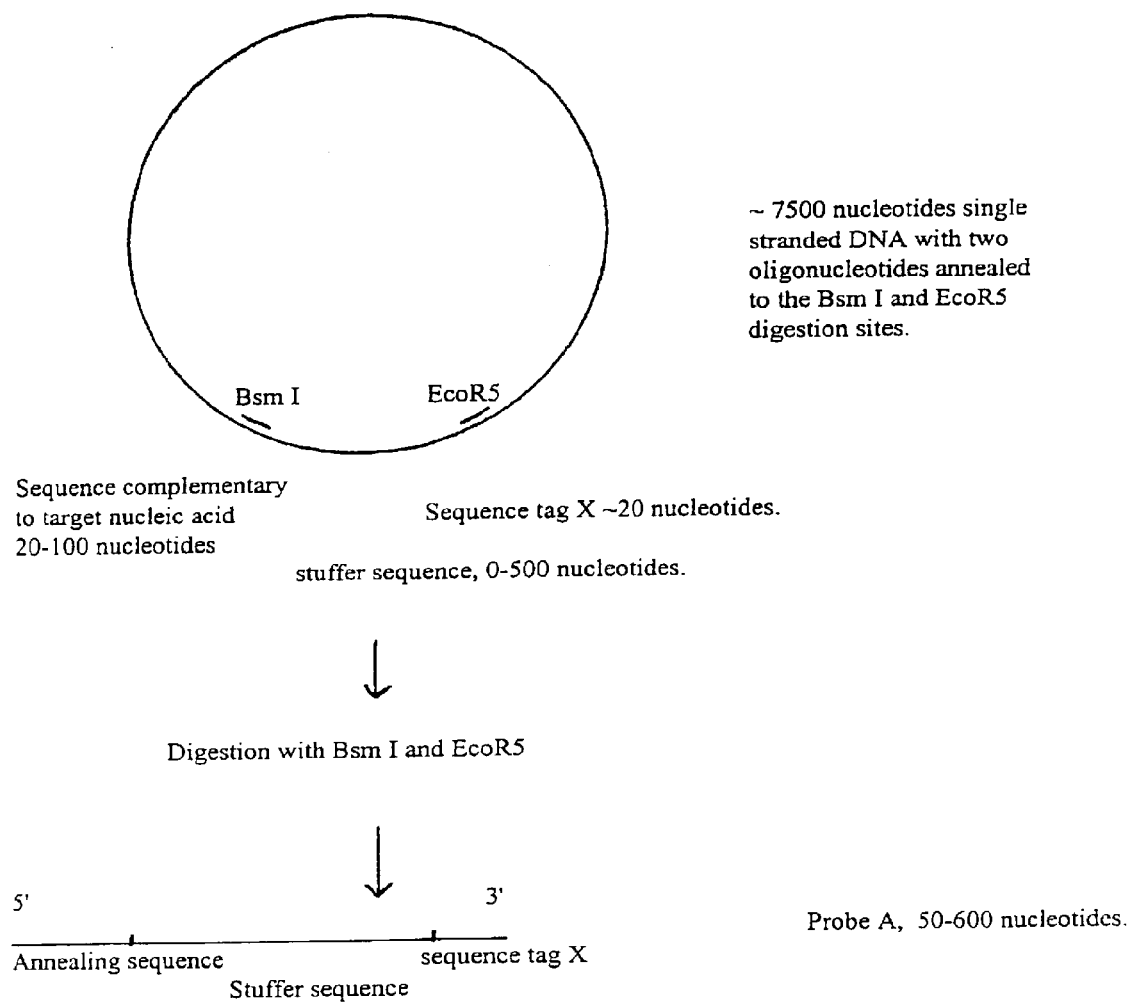

FIGURE 5 : Simplified way of performing the MLPA invention.

Probes provided in the MLPA assay:

| Target sequence | A probe | wild type specific Probe type B | mutant specific Probe type B | Length of amplification product |
|---|---|---|---|---|
| Control sequence 1 | Yes | Yes | - | 150 bp. |
| Control sequence 2 | Yes | Yes | - | 350 bp. |
| Mutation site 1 (abundant) | Yes | No | Yes | 200 bp. |
| Mutation site 2 (rare) | Yes | No | Yes | 250 bp |
| Mutation site 3 (rare) | Yes | No | Yes | 250 bp. |
| Mutation sites 4-100 | Yes | No | Yes | 250 bp. |

Except for the control target sequences, no type B probes specific for wildtype sequences are used.

Results obtained on agarose gel electrophoresis :

| Lane | 1 | 2 | 3 | 4 | 5 | 6 | 7 | 8 | 9 | 10 | 11 | 12 |
|---|---|---|---|---|---|---|---|---|---|---|---|---|
| Control band | — | — | — | — | — | — | — | — | — | — |  | — |
| Rare mutation |  |  |  |  |  |  |  | — |  |  |  |  |
| Abundant mutation |  |  |  |  | — |  |  |  |  |  |  |  |
| Control band | — | — | — | — | — | — | — | — | — | — |  | — |

Conclusion: Sample 5 contains the abundant mutation.
    Sample 8 contains one of the 99 rare mutations
    MLPA assay on sample 11 failed
    Other samples do not contain any of the 100 mutations tested.

FIGURE 6 : Use of the MLPA invention for the detection of mRNA's.
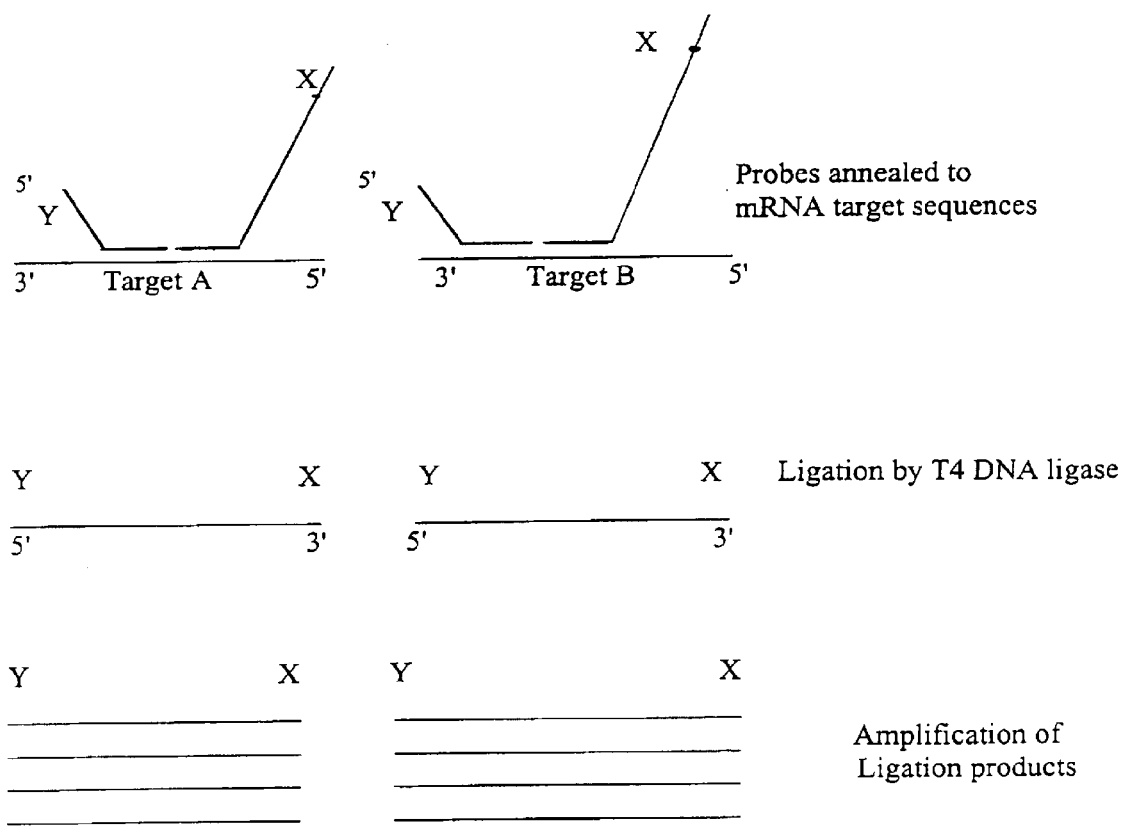

FIGURE 7 : Detection of cDNA target sequences.
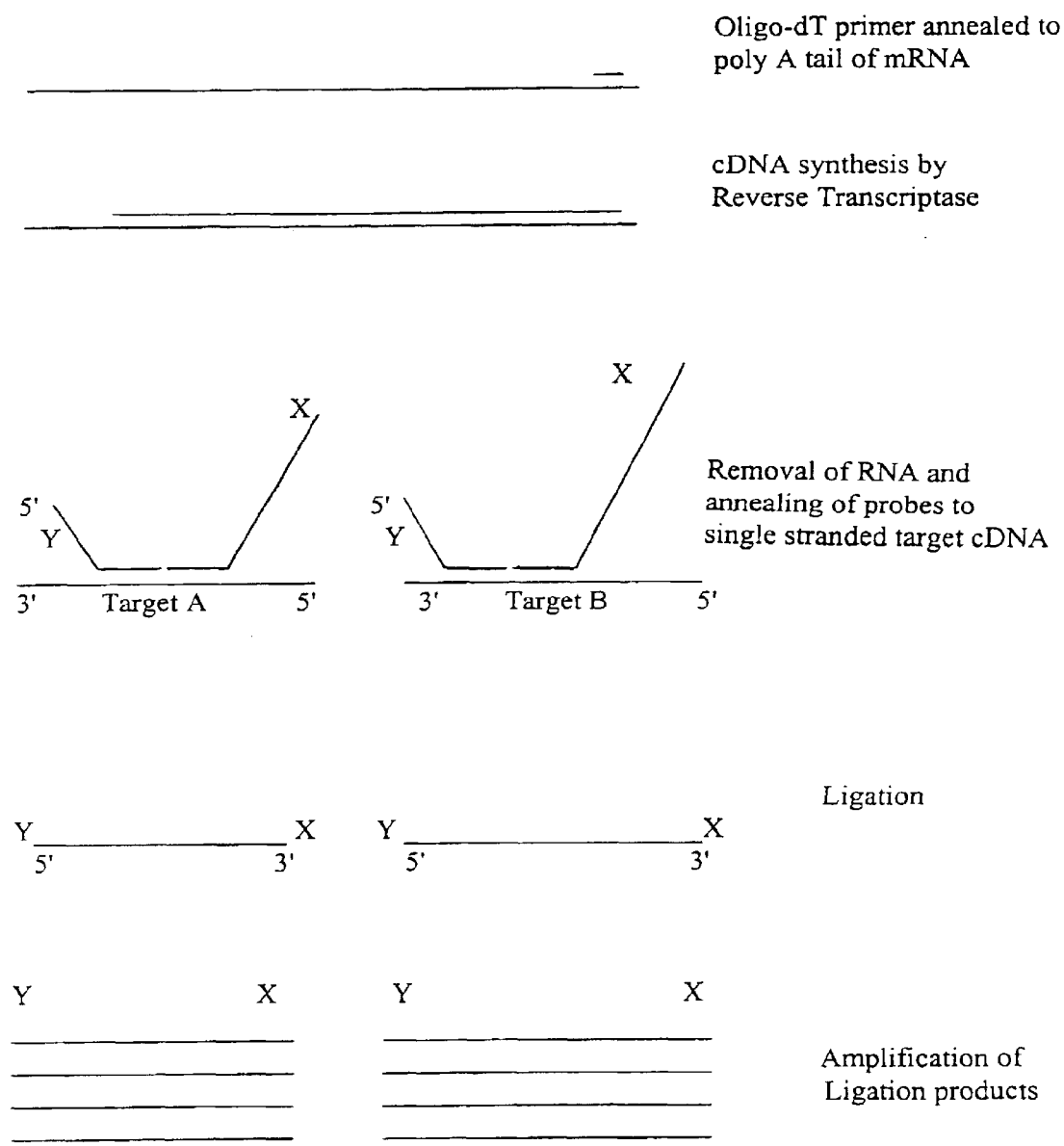

FIGURE 8 : Detection of cDNA target sequences using gene specific reverse transcription primers.
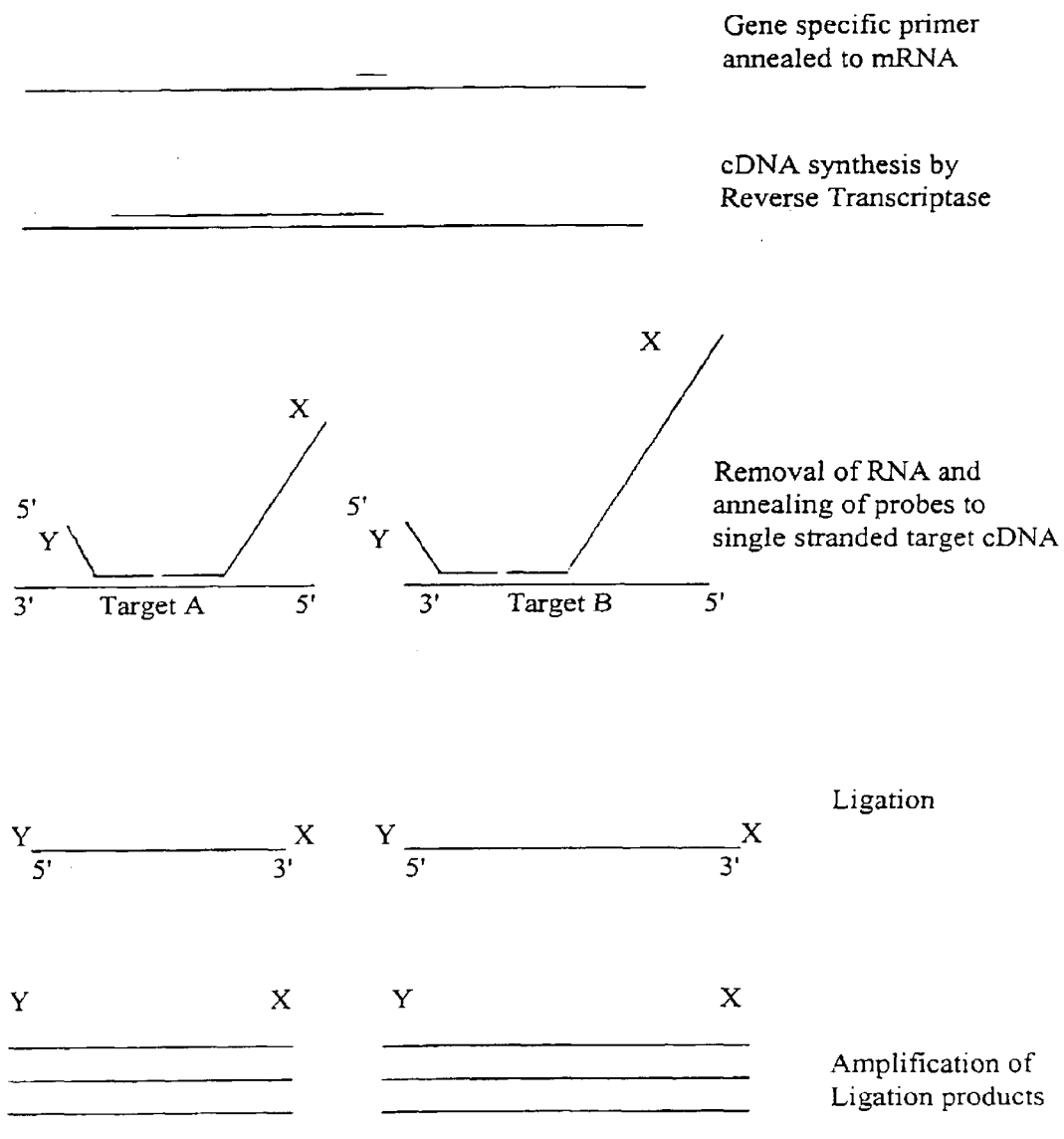

FIGURE 9: Detection of cDNA target sequences using tagged gene specific reverse transcription primers.
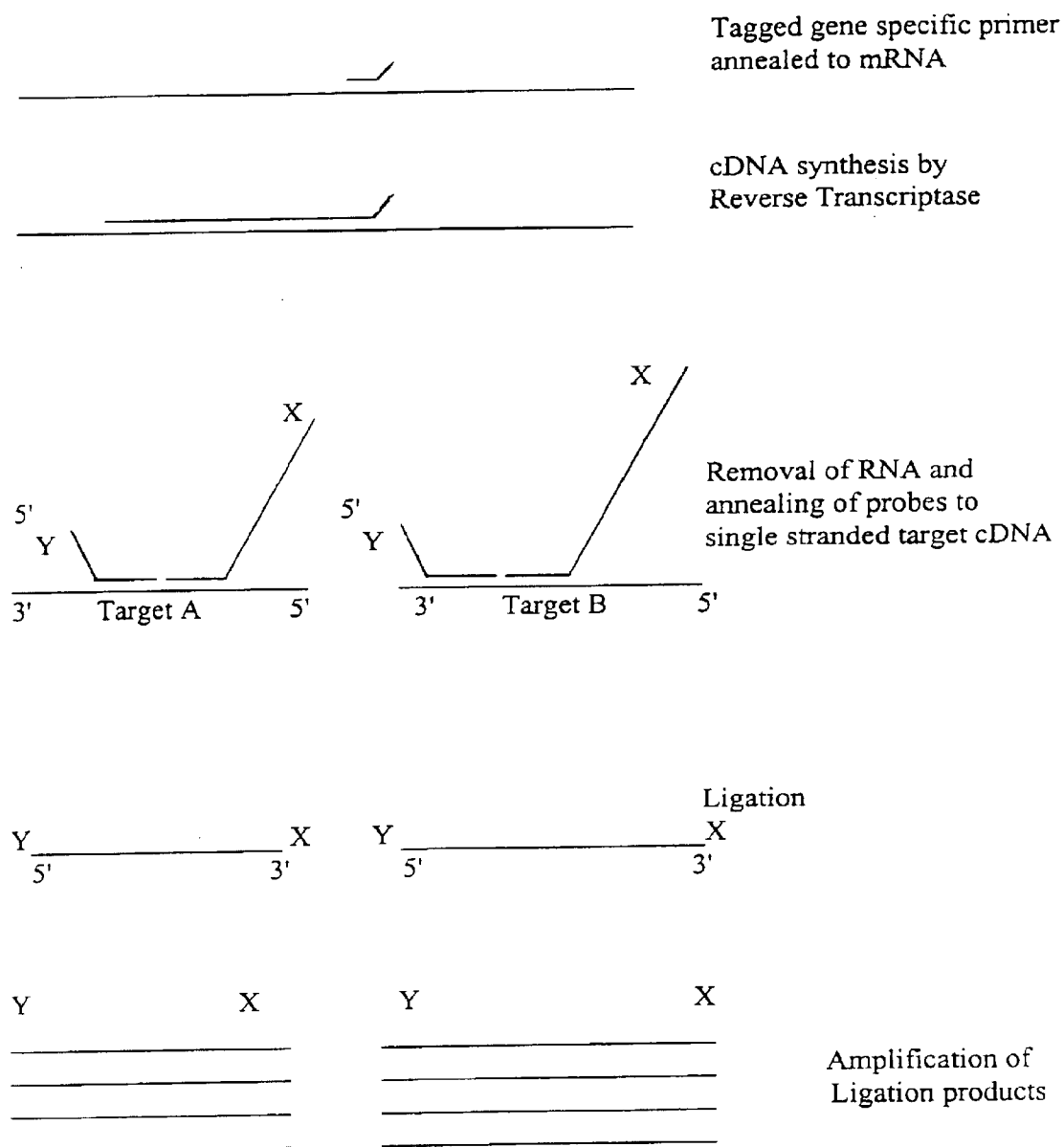

FIGURE 10 : Detection of cDNA target sequences using tagged gene specific reverse transcription primers.

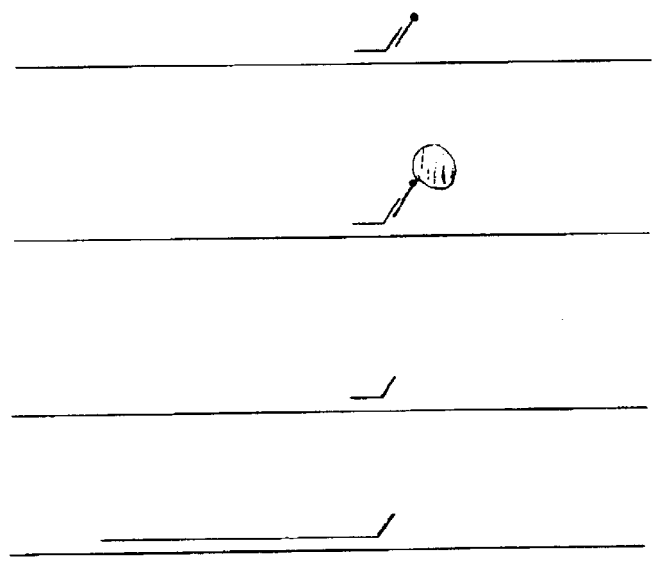

Annealing of sequence tagged reverse transcription primer + biotinylated complementary oligonucleotide to target RNA in whole cell lysates Purification of biotin contai ning complexes with immobi- sed streptavidine.

Elution at a temperature at which the RT primer-RNA complex is not dissociated cDNA synthesis by Reverse Transcriptase

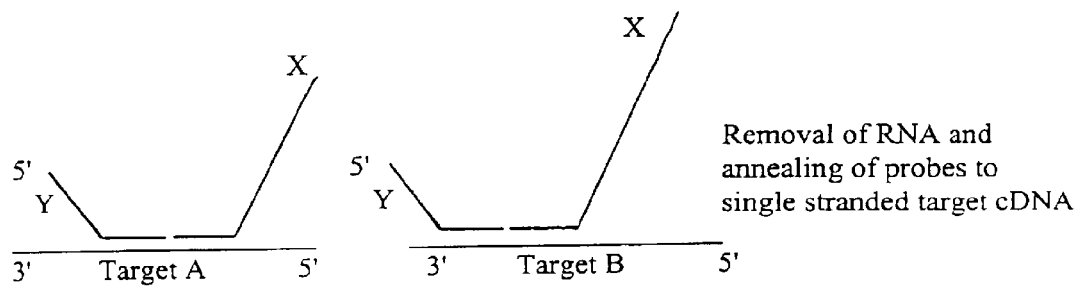

Removal of RNA and annealing of probes to single stranded target cDNA

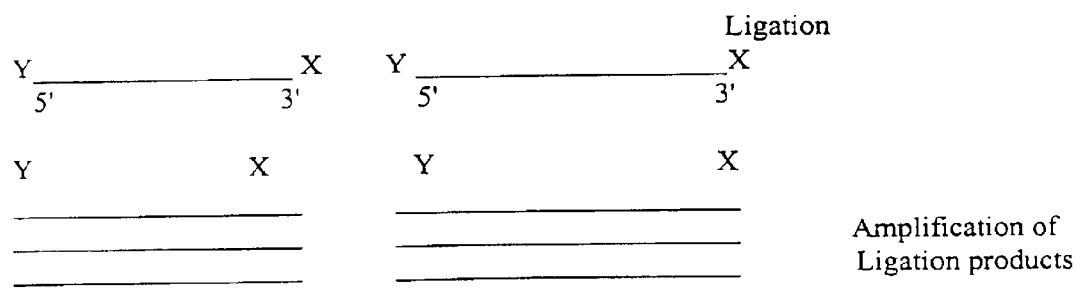

Ligation

Amplification of Ligation products

FIGURE 11 : The use of reverse transcriptase primers that are part of one of the probes.
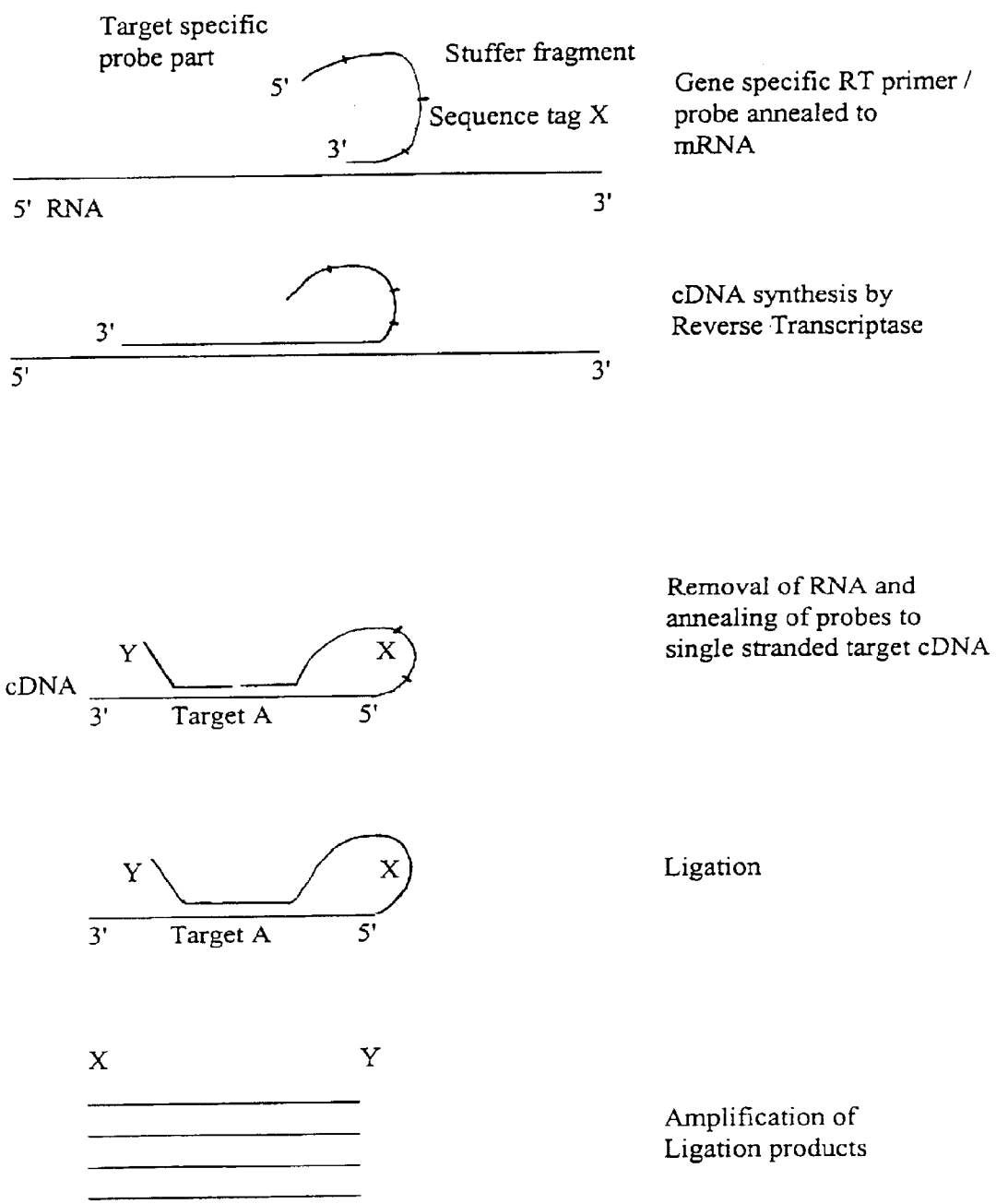

FIGURE 12: The use of the MLPA invention without the use of target specific clones.
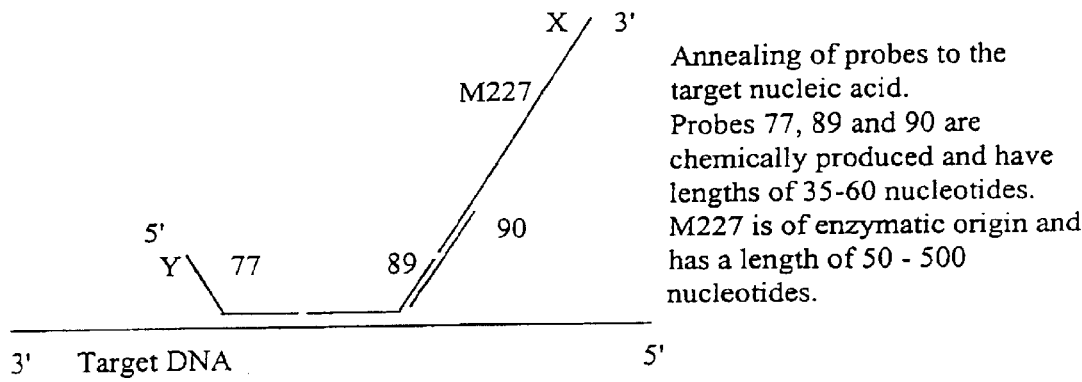
Annealing of probes to the target nucleic acid.
Probes 77, 89 and 90 are chemically produced and have lengths of 35-60 nucleotides.
M227 is of enzymatic origin and has a length of 50 - 500 nucleotides.
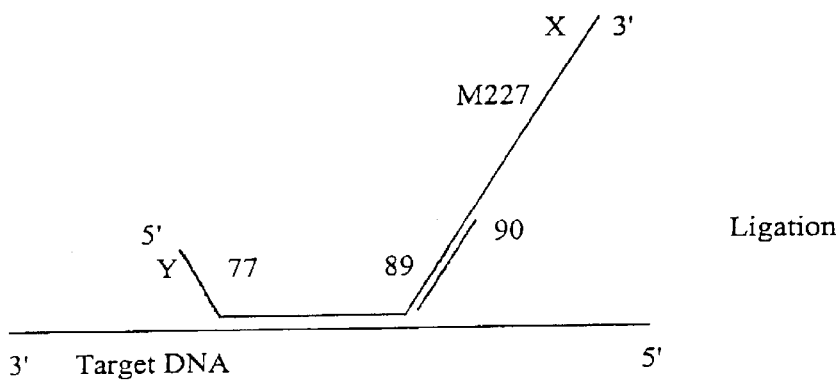
Ligation
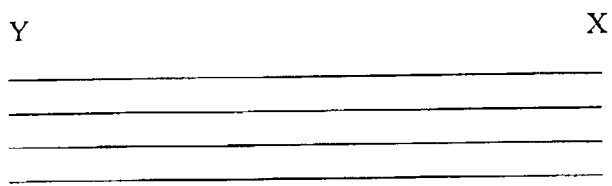
Amplification of ligation products, using sequence tag X of M227 and tag Y of probe 77.

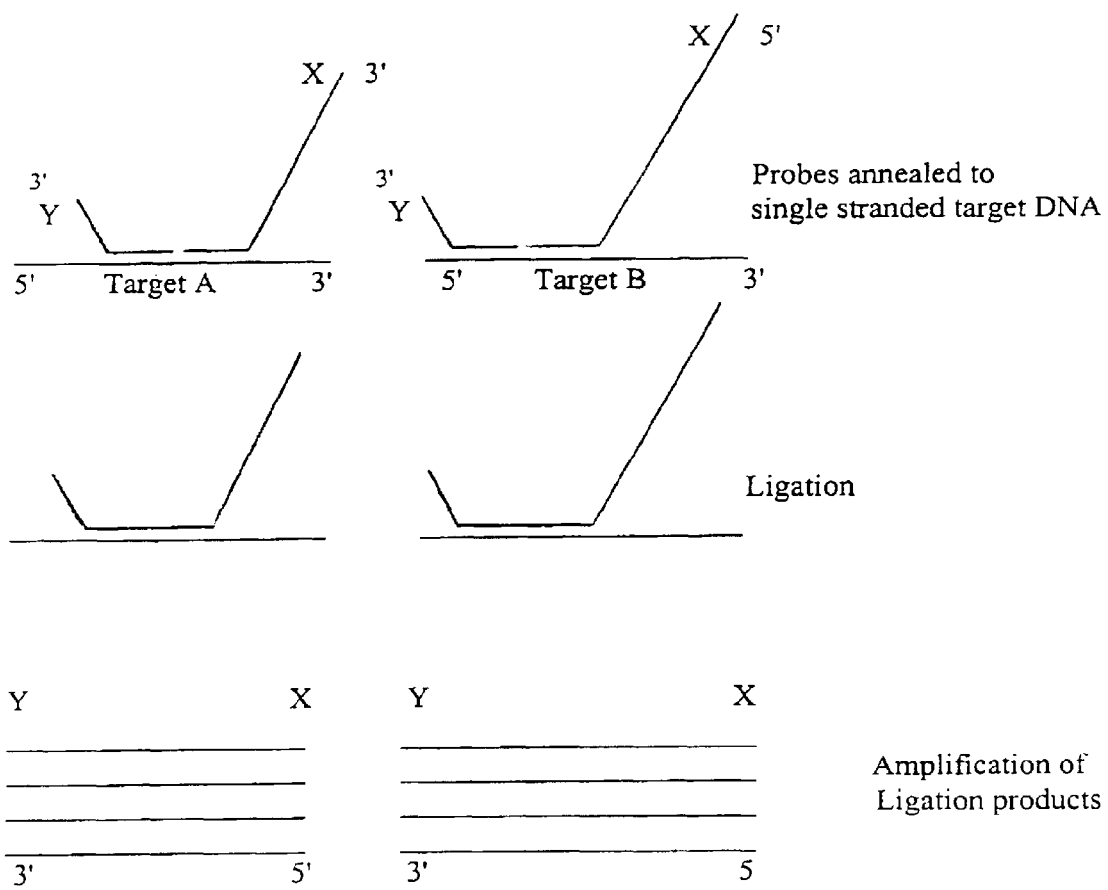
FIGURE 13 : Alternative way of performing the MLPA invention.

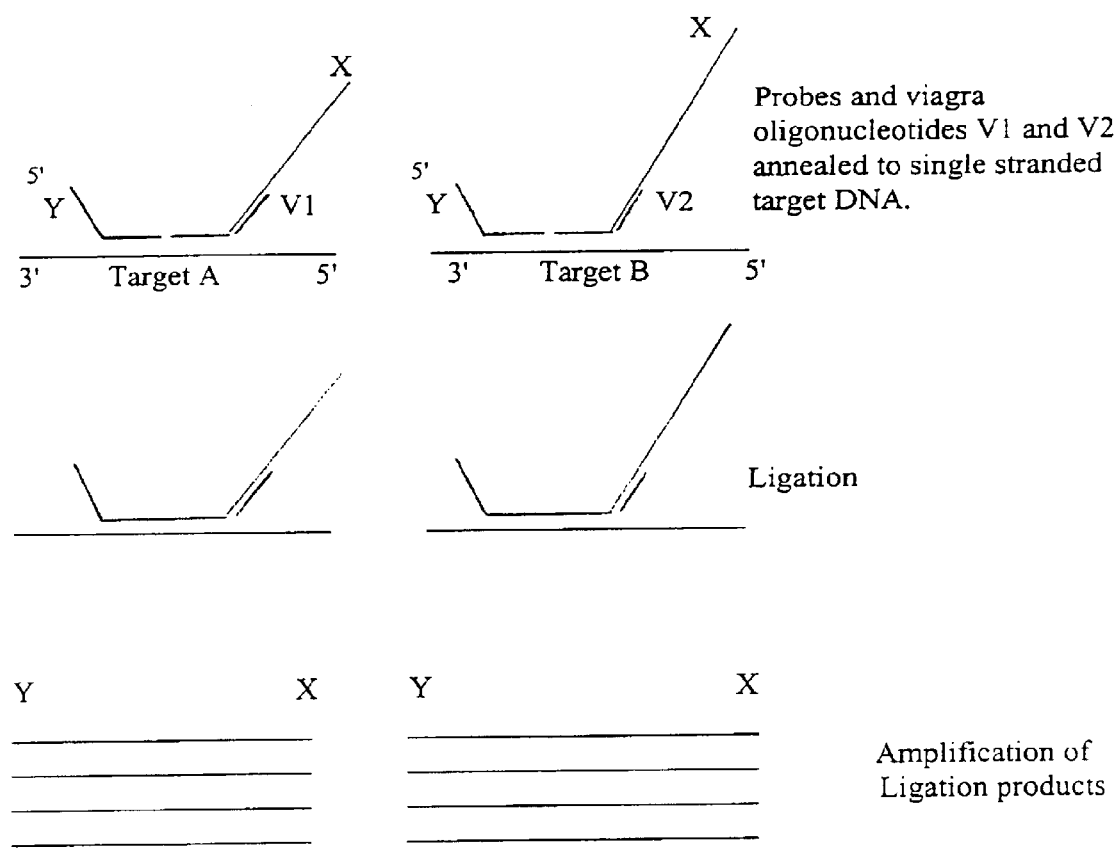
FIGURE 14: The use of "viagra" oligonucleotides to reduce internal secondary structures of the probes.

FIGURE 15 : mRNA detection and relative quantification with complete probes.
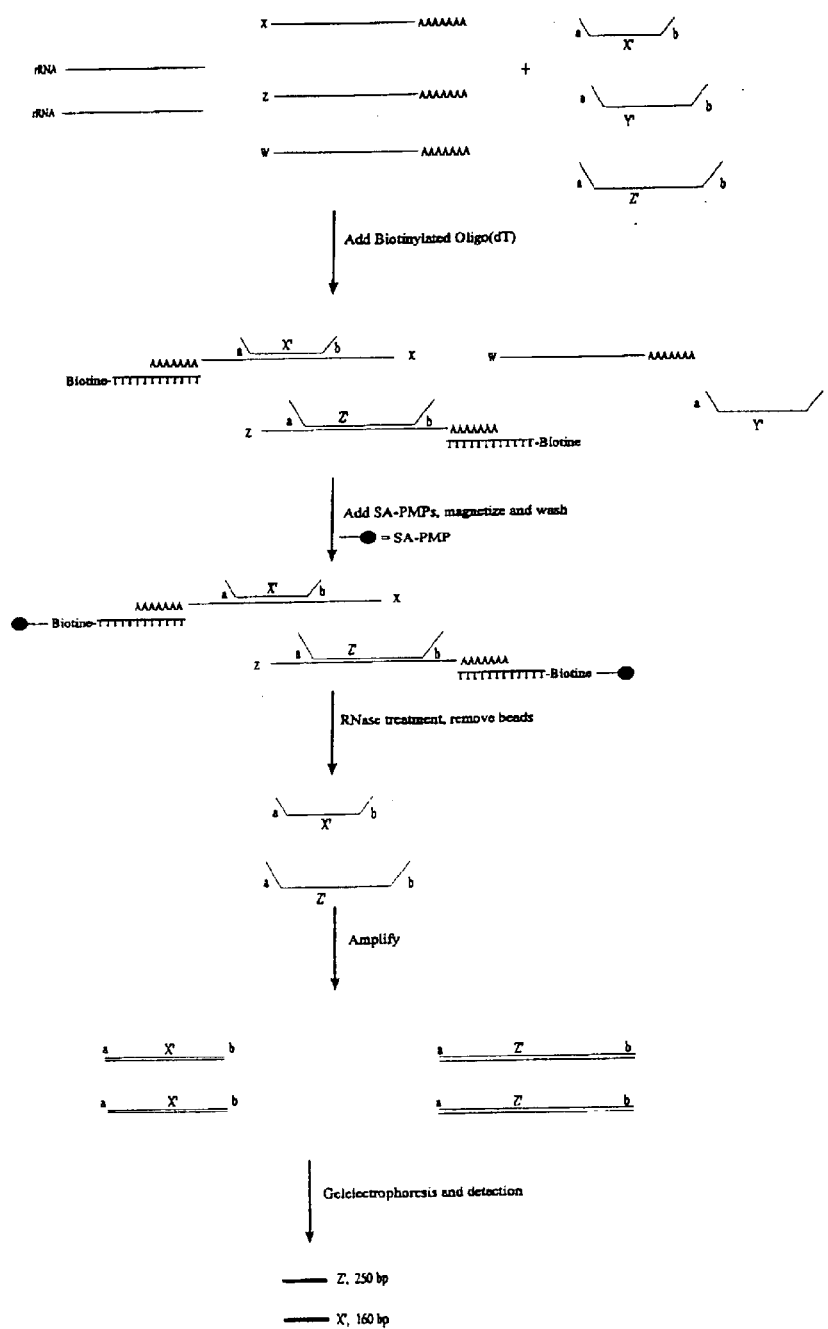

FIGURE 21 : Alternative way of performing the MLPA invention.
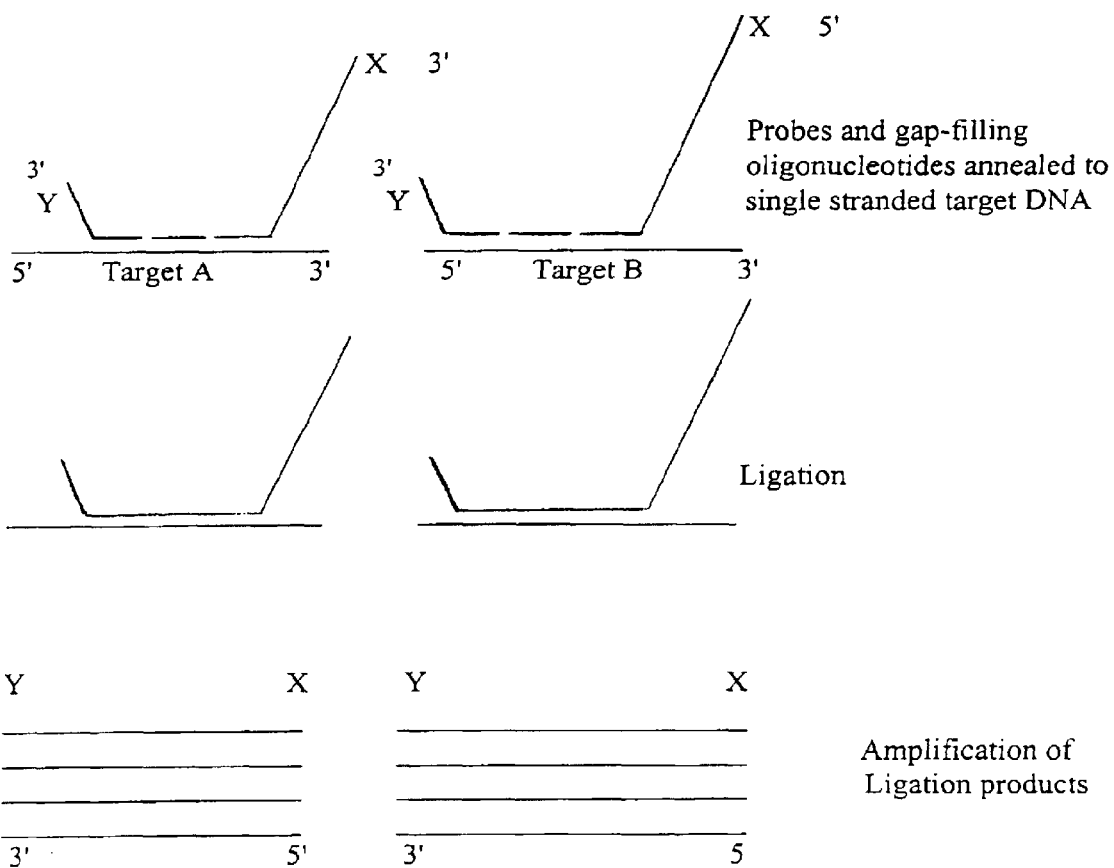

FIGURE 22 : Alternative way of performing the MLPA invention.
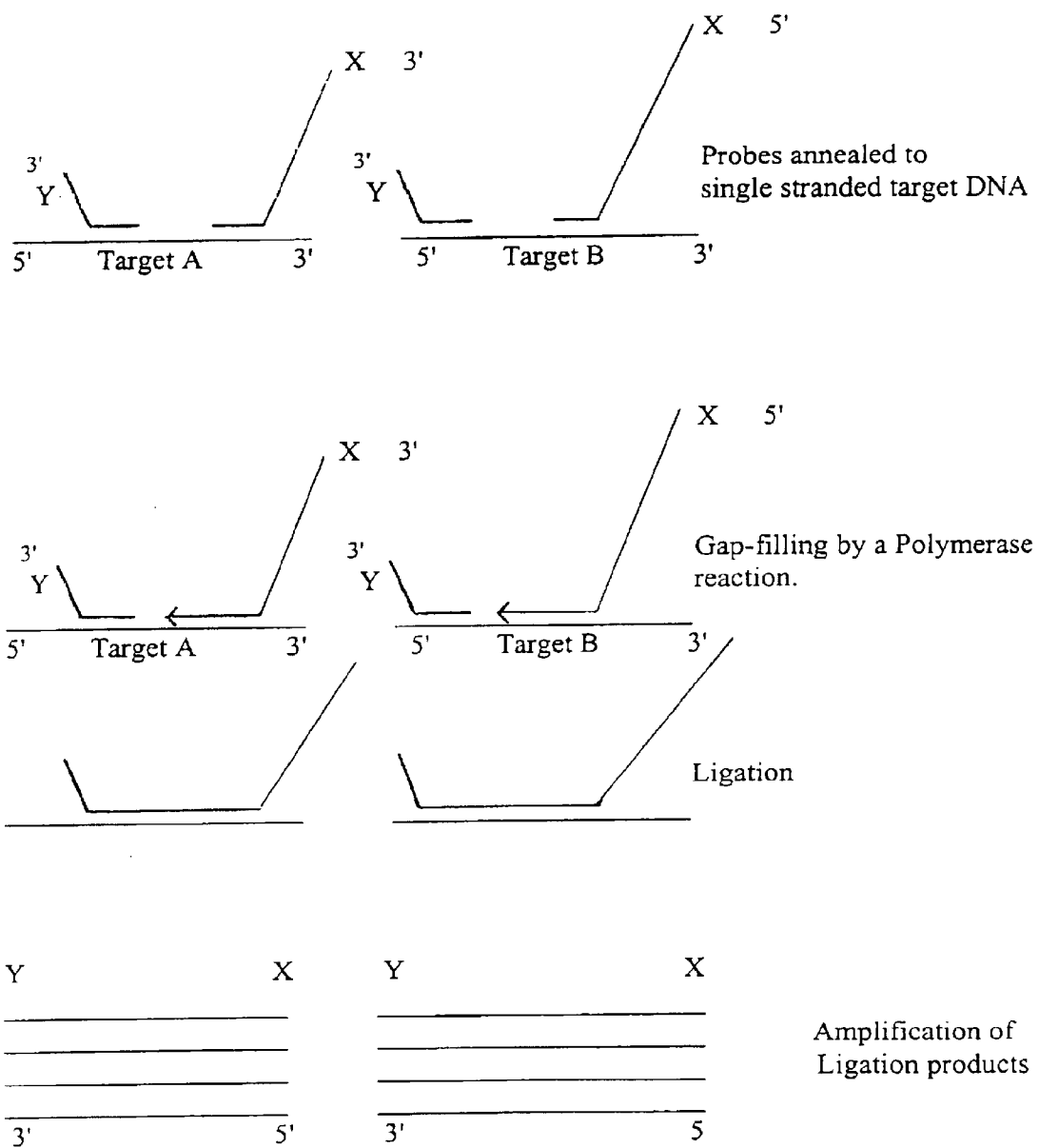

FIGURE 23 : The use of the MLPA invention for the determination of the break-point site in chromosomal rearrangements.

Wildtype DNA + Probes:
BCR: 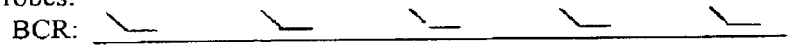

ABL: 

Elongation of Probes:
BCR: 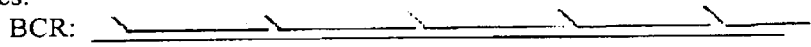

ABL: 

No ligation events possible ; No exponential amplification of ligated probes.

Rearranged DNA + Probes:
BCR  ABL

Elongation of Probes:
BCR  ABL

Ligation of probes:
BCR  ABL

Amplification of the fragment spanning the breakpoint.

Sequence determination of the amplified fragment to confirm that it contains both BCR and ABL sequences, and to determine the exact breakpoint.

Design of (nested) PCR primers specific for the rearranged DNA.

Figure 24

| mix 1C ||| mix 2C ||| mix 3C |||
| HUGO | Chr pos | Length | HUGO | Chr pos | Length | HUGO | Chr pos | Length |
| --- | --- | --- | --- | --- | --- | --- | --- | --- |
| PTK2 | 08q24 | 130 | RAD17 | 05q | 142 | LTA | 06p21 | 136 |
| ERBB2 | 17q21.1 | 142 | FGF3 | 11q13 | 148 | CFLAR | 02q33 | 142 |
| NRAS | 01p13.2 | 148 | MYC | 08q24.12 | 154 | PTEN | 10q23.3 | 148 |
| IL4 | 05q31.1 | 154 | MET | 07q31 | 160 | AR | Xq | 154 |
| RB1 | 13q14 | 160 | DNMT1 | 19p13.3-p13.2 | 166 | TNFRSF1B | 01p36.3 | 166 |
| ABCB1 | 07q21 | 166 | RELA | 11q13 | 175 | TNFRSF1A | 12p13 | 175 |
| Hs.28355 | 15 | 175 | KIAA0170 | 06p21 | 184 | CASP1 | 11q22.2-q22.3 | 184 |
| CCND1 | 11q13 | 184 | IL6 | 07p21 | 193 | B2M | 15q21-q22.2 | 194 |
| NCOA3 | 20q12 | 193 | TP53 | 17p13.1 | 202 | MME | 03q21-q27 | 202 |
| CDKN2A | 09p21 | 202 | CDKN2B | 09p21 | 211 | IFNG | 12q14 | 211 |
| GADD45A | 01p34-p12 | 211 | RB1 | 13q14 | 220 | SLA | 08q24.2-q24.3 | 220 |
| TANK | 02q24-q31 | 220 | PDGFB | 22q13.1 | 229 | SCYA3 | 17q11-q21 | 229 |
| EMS1 | 11q13 | 229 | BAK1 | 06p21.3 | 238 | IL1RN | 02q14.2 | 238 |
| MYC | 08q24.12 | 238 | ATM | 11q22-q23 | 247 | ETV6 | 12p13 | 247 |
| IL1A | 02q14 | 256 | BCL2 | 18q21.3 | 256 | TP73 | 01p36 | 256 |
| PIK3CA | 03q26.3 | 265 | CDKN2D | 19p13 | 265 | THBD | 20p11.2 | 265 |
| IL13 | 05q31 | 274 | BRCA1 | 17q21 | 274 | IRF4 | 06p25 | 274 |
| BRCA1 | 17q21 | 283 | NFKB1 | 04q24 | 283 | FMR2 / FRAXE | Xq28 | 283 |
| DNTT / TDT | 10q23-q24 | 292 | CCND1 | 11q13 | 292 | TFF1 | 21q22.3 | 292 |
| BAX | 19q13.3-q13.4 | 301 | IL12A | 03p12-p13 | 301 | BCL6 | 03q27 | 301 |
| TMSB10 | 02 | 310 | AXIN2 | 17q23-q24 | 310 | LRMP | 12 | 310 |
| F3 | 01p22-p21 | 328 | TNF | 06p21.3 | 319 | CTPS | 01p34.1 | 319 |
| HRAS | 11p15.5 | 337 | SRY | Yp11.3 | 328 | BRCA1 | 17q21 | 328 |
| BCL2 | 18q21.2 | 346 | CCNB1 | 05q | 337 | ERBB2 | 17q21.1 | 337 |
| BRCA2 | 13q12.3 | 355 | THRSP | 11q13.5 | 346 | MVP | 16 | 346 |
| MDM2 | 12q14.3-q15 | 364 | CCND2 | 12p13 | 355 | BIRC2 | 11q22-q23 | 355 |
| XRCC4 | 05q12 | 373 | PTPN1 | 20q13.1-q13.2 | 364 | SEMA3C | 07q21-q31 | 364 |
| CDH1 | 16q22.1 | 382 | CASP6 | 04q25 | 373 | IL2 | 04q26 | 373 |
| CRK | 17p13.3 | 391 | VEGF | 06p12 | 382 | IL12B | 05q31.1-q33.1 | 382 |
| STK15 | 20q13 | 400 | KLK3 | 19q13 | 391 | NFKBIA | 14q13 | 391 |
| ABCB4 | 07q21.1 | 409 | BCAS2 | 01p13.3 | 400 | PRKDC | 08q11 | 400 |
| BCAR3 | 01p13.2 | 418 | ERBB2 | 17q21.1 | 409 | CD44 | 11pter-p13 | 409 |
| CDKN1A | 06p21.2 | 427 | ABCG2 | 04q22 | 418 | Hs.89125 | 06p21 | 418 |
| LMO2 | 11 | 436 | ERBB4 | 02q33 | 427 | CASP2 | 07q35 | 427 |
| IL1B | 02q14 | 445 | TRAF2 | 09q34 | 436 | TGFB2 | 01q41 | 436 |
| TIMP2 | 17q25 | 454 | IER3 | 06p21.3 | 445 | TNFRSF7 | 12p13 | 445 |
| THBS1 | 15q15 | 463 | CTNNB1 | 03p22 | 454 | IGFIR | 15q25-q26 | 454 |
|  |  |  | MDM2 | 12q14.3-q15 | 463 |  |  |  |

| Probe | Chr. Pos. | DNA mix | Male Norm. signal | Female Norm. signal | Gene copy nr. in Female DNA-sample |
|---|---|---|---|---|---|
| ERBB2(1) | 17q21.1 | 1C | 1.0 | 1.0 | |
| MYC(1) | 8q24.12 | 1C | 1.0 | 1.0 | |
| CDH1 | 16q22.1 | 1C | 1.0 | 1.0 | |
| MYC(2) | 8q24.12 | 2C | 1.0 | 1.2 | |
| SRY | Yp11.3 | 2C | 1.0 | 0.0 | 0 copies |
| ERBB2(2) | 17q21.1 | 2C | 1.0 | 1.0 | |
| AR | Xq | 3C | 1.0 | 1.8 | 2 copies |
| ERBB2(3) | 17q21.1 | 3C | 1.0 | 1.0 | |

B

| Probe | Chr. Pos. | DNA mix | Female Norm. signal | SKBR-3 Norm. signal | Rel. gene copy nr. in SKBR-3 DNA-sample |
|---|---|---|---|---|---|
| ERBB2(1) | 17q21.1 | 1C | 1.0 | 5.3 | 10 copies |
| MYC(1) | 8q24.12 | 1C | 1.0 | 6.1 | 12 copies |
| CDH1 | 16q22.1 | 1C | 1.0 | 0.0 | 0 copies |
| MYC(2) | 8q24.12 | 2C | 1.0 | 5.3 | 10 copies |
| SRY | Yp11.3 | 2C | 1.0 | 1.0 | 0 copies |
| ERBB2(2) | 17q21.1 | 2C | 1.0 | 6.5 | 13 copies |
| AR | Xq | 3C | 1.0 | 0.9 | 2 copies |
| ERBB2(3) | 17q21.1 | 3C | 1.0 | 6.0 | 12 copies |

Total RNA from:
1. untreated blood
2. blood + 1 ng/ml LPS
3. blood + 10 ng/ml LPS
4. salivary gland
5. prostate
6. pancreatic tissue
7. liver
8. adrenal gland
9. thyroid

SEQUENCE LISTING

<160> NUMBER OF SEQ ID NOS: 113

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 1
cggcgtcgag actagaccgg ctgggtcggc acagcctg                         38

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 2
cccgcgccag caagatccga caggcggagc agcatgag                         38

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 3
cggcgtcgag actagaccgg gaaggcgaca gtgcctaag                        39

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 4
cccgcgccag caagatccta ggtcttcagg agctgatcaa ca                        42

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 5
ggcgtcgaga ctagaccg                                                   18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 6
gacgcgccag caagatcc                                                   18

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 7
tttttttttt tttttttttt tttttttttt tttttttttt ttt                       43

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 8
aatttcgcga tatcccatgg cttaagagtc gactcgcgat atc                       43

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 9
agctgatatc gcgagtcgac tcttaagcca tgggatatcg cga                       43

<210> SEQ ID NO 10

<211> LENGTH: 58
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 10
catggcgtcg agactagacc gaattcgagc gcgcaaagct tggatcttgc tggcgcgt     58

<210> SEQ ID NO 11
<211> LENGTH: 56
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 11
cgacgcgcca gcaagatcca agctttgcgc gctcgaattc ggtctagtct cgacgc       56

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 12
cctgtagcgt tccacagaca accctc                                         26

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 13
ggaacgctac aggcgttgta gtttgtactg                                     30

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 14
catggcagtt cgaacttgaa tgccttagag tactcatcac cggttctgg                49

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 15
aattccagaa ccggtgatga gtactctaag gcattcaagt tcgaactgc                49

<210> SEQ ID NO 16
<211> LENGTH: 47

<212> TYPE: DNA
<213> ORGANISM: Artificial Sequence
<220> FEATURE:
<223> OTHER INFORMATION: Description of Artificial Sequence:synthetic
      DNA

<400> SEQUENCE: 16
ccggtgcatg cttagcgcgc actctagatt ggatcttgct ggcgcgt                    47

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 17
cgacgcgcca gcaagatcca atctagagtg cgcgctaagc atgca                      45

<210> SEQ ID NO 18
<211> LENGTH: 121
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 18
gaatttcgcg atatcccatg gcagttcgaa cttgaatgcc ttagagtact catcaccggt      60
gcatgcttag cgcgcactct agattggatc ttgctggcgc gtcgactcgc gatatcagct     120
t                                                                    121

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 19
caccacgcat gctcgccata gtcgccttca                                       30

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 20
cacaacctct agactgataa tcaacgtcct cagg                                  34

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 21
caccacgcat gctgctggcg tggtcaactc                                       30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 22
caacctctag actccctcaa gttaacaccg                                      30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 23
caccacgcat gcggctagca tgactggtgg                                      30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 24
cacaacctct agaaacgtca gccgtcagga                                      30

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 25
caccacgcat gccgtggatg accgcgatg                                       29

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 26
cacaacctct agaacggtct gcttgctgtt c                                    31

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 27
cccgcttatt gttgaaccta ctgcggcata gagtct                               36

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 28
ctagagactc tatgccgcag taggttcaac aataagcggg catg                44

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 29
agctgatatc gcgagtg                                              17

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 30
agctggcttc aaagaaaaat cctaaacaat caactagaaa catg                44

<210> SEQ ID NO 31
<211> LENGTH: 42
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 31
tttctagttg attgtttagg atttttcttt gaagccagct gg                  42

<210> SEQ ID NO 32
<211> LENGTH: 44
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 32
cttcttataa atcaaactaa acatagctat tctcatctaa catg                44

<210> SEQ ID NO 33
<211> LENGTH: 42
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 33
ttagatgaga atagctatgt ttagtttgat ttataagaag gg                  42

<210> SEQ ID NO 34

<211> LENGTH: 44
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 34
ttggtgtttc ctatgatgaa tatagataca gaagatacaa catg           44

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 35
ttgtatcttc tgtatctata ttcatcatag gaaacaccaa gg             42

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 36
taggtttacc ttctgttggc atgtcacatg                           30

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 37
tgacatgcca acagaaggta aacctagg                             28

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 38
caatctttta aacagactgg agagtttgga atcatg                    36

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 39
attccaaact ctccagtctg tttaaaagat tggg                      34

<210> SEQ ID NO 40
<211> LENGTH: 19

```
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 40
cagctggcat tcaagttca                                                    19

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 41
taagaagggc attcaagtta                                                   20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 42
acaccaaggc attcaagttc a                                                 21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 43
taaacctagg cattcaagtt a                                                 21

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 44
aagattgggc attcaagtta                                                   20

<210> SEQ ID NO 45
<211> LENGTH: 46
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 45
gggttcccta agggttggat attcttttgc agagaatggg atagag                      46

<210> SEQ ID NO 46
<211> LENGTH: 50
<212> TYPE: DNA
```

<213> ORGANISM: Artificial Sequence
<220> FEATURE:
<223> OTHER INFORMATION: Description of Artificial Sequence:synthetic
      DNA

<400> SEQUENCE: 46
gggttcccta agggttggag atatattctt ttgcagagaa tgggatagat         50

<210> SEQ ID NO 47
<211> LENGTH: 46
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 47
gggttcccta agggttggac taagggcctg tgcaaggaag tattac             46

<210> SEQ ID NO 48
<211> LENGTH: 50
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 48
gggttcccta agggttggag atactaaggg cctgtgcaag gaagtattaa         50

<210> SEQ ID NO 49
<211> LENGTH: 46
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 49
gggttcccta agggttggac tggcaccatt aaagaaaata tcatct             46

<210> SEQ ID NO 50
<211> LENGTH: 50
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 50
gggttcccta agggttggag atacacctgg caccattaaa gaaatatca          50

<210> SEQ ID NO 51
<211> LENGTH: 45
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 51
gggttcccta agggttggaa atcttgtatg gtttggttga cttgg              45

<210> SEQ ID NO 52
<211> LENGTH: 49
<212> TYPE: DNA
<213> ORGANISM: Artificial Sequence

```
<220> FEATURE:
<223> OTHER INFORMATION: Description of Artificial Sequence:synthetic
      DNA

<400> SEQUENCE: 52 ggggttcccta agggttggaa gatcattctt gtatggtttg gttgacttg                    49

<210> SEQ ID NO 53
<211> LENGTH: 45
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 53 ggggttcccta agggttggaa tgtctcctgg acagaaacaa aaaaa                        45

<210> SEQ ID NO 54
<211> LENGTH: 49
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 54 ggggttcccta agggttggag atgactgtct cctggacaga aacaaaaaa                    49

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 55 ggggttcccta agggttgg                                                      18

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 56
gtgccagcaa gatccaatct aga                                                 23

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 57
caccacgcat gctgcgggtg ctgccttagg                                          30

<210> SEQ ID NO 58
<211> LENGTH: 34
<212> TYPE: DNA
<213> ORGANISM: Artificial Sequence
<220> FEATURE:
```

<223> OTHER INFORMATION: Description of Artificial Sequence:synthetic
      DNA

<400> SEQUENCE: 58
cacaacctct agagaactca ttgtcgaact cagc                              34

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 59
caccacgcat gcggctgcgc gaggaatc                                     28

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 60
cacctctaga ctcatggatg tcagaagctg                                   30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 61
caccacgcat gcccgtgagc ctatgcttga                                   30

<210> SEQ ID NO 62
<211> LENGTH: 34
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 62
cacaacctct agacttgatg gtctggaaga ggtg                              34

<210> SEQ ID NO 63
<211> LENGTH: 34
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 63
caccacgcat gcgtacgatg agaaccctga ggca                              34

<210> SEQ ID NO 64
<211> LENGTH: 34
<212> TYPE: DNA
<213> ORGANISM: Artificial Sequence
<220> FEATURE:
<223> OTHER INFORMATION: Description of Artificial Sequence:synthetic

DNA

<400> SEQUENCE: 64
cacaacctct agaacaatcg tggtacgtat gcag                34

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 65
caaaatgtac aagaccacac cggcatg                27

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 66
ccggtgtggt cttgtacatt ttggg                25

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 67
ctgcccactg catcaggaac taacatg                27

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 68
ttagttcctg atgcagtggg caggg                25

<210> SEQ ID NO 69
<211> LENGTH: 33
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 69
aagatcctgg aggatttcct acccaaatac atg                33

<210> SEQ ID NO 70
<211> LENGTH: 31
<212> TYPE: DNA
<213> ORGANISM: Artificial Sequence
<220> FEATURE:
<223> OTHER INFORMATION: Description of Artificial Sequence:synthetic
      DNA

```
<400> SEQUENCE: 70
tatttgggta ggaaatcctc caggatcttg g                              31

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 71
agcagaggaa gaccatgtgg accaaacatg                                30

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 72
tttggtccac atggtcttcc tctgctgg                                  28

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 73
cattttgggc attcaagtta                                           20

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 74
ggcagggcat tcaagtta                                             18

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 75
aggatcttgg cattcaagtt a                                         21

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence:synthetic
      DNA
```

```
<400> SEQUENCE: 76
tctgctggca ttcaagtta                                              19

<210> SEQ ID NO 77
<211> LENGTH: 49
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 77
gggttcccta agggttggaa aataagacag aaattcggga aaaactagc              49

<210> SEQ ID NO 78
<211> LENGTH: 45
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 78
gggttcccta agggttggaa gatgaacccc agtgggtcct cacag                  45

<210> SEQ ID NO 79
<211> LENGTH: 45
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 79
gggttcccta agggttggaa atggagaagc ggagtgaaat ttcct                  45

<210> SEQ ID NO 80
<211> LENGTH: 42
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 80
gggttcccta agggttggaa caactgctct gctgcagggg ac                    42

<210> SEQ ID NO 81
<211> LENGTH: 60
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 81
gtgtgtgtgt gtgtgtgtgt gtgtgtgaat ccagggaatc ataaatcatg ccaaagccag  60

<210> SEQ ID NO 82
<211> LENGTH: 60
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 82
```

```
gtgtgtgtgt gtgtgtgtgt gtgtgtggcc tgtgtcttca ggatgaaaca ggctgtgccg    60
```

<210> SEQ ID NO 83
<211> LENGTH: 60
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 83

```
gtgtgtgtgt gtgtgtgtgt gtgtgtggca ggtggctctt cctccacatc acgactgggg    60
```

<210> SEQ ID NO 84
<211> LENGTH: 60
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 84

```
gtgtgtgtgt gtgtgtgtgt gtgtgtgcag cctgctcccc tgagcgaggc acaagggtac    60
```

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 85

```
agtcgacgcg ccagcaaga                                                 19
```

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 86

```
caccacgcat gcctaccctg cgtccattgc                                     30
```

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 87

```
cacacctcta gagctggacc tcggactagc                                     30
```

<210> SEQ ID NO 88
<211> LENGTH: 17
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 88
ggtaggcatg caccgga                                                    17

<210> SEQ ID NO 89
<211> LENGTH: 50
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 89
caaaatgtac aagaccacac cggaacccgt atcactcgtg agaaaggcgc                 50

<210> SEQ ID NO 90
<211> LENGTH: 49
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 90
ggttcgcaat ggacgcaggg tagggcgcct ttctcacgag tgatacgga                  49

<210> SEQ ID NO 91
<211> LENGTH: 35
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 91
caccacgcat gctccagact ctgctgactt ctttg                                 35

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 92
caacctctag atgtccttgg gtcctcttgg                                       30

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 93
caccacgcat gccgcatccg acaaggcgca                                       30

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 94
acaacctcta gacagccatt tacctcccca                                       30

<210> SEQ ID NO 95
<211> LENGTH: 35
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 95
ttttgagact actgaacact gaaggagaat acatg                          35

<210> SEQ ID NO 96
<211> LENGTH: 33
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 96
tattctcctt cagtgttcag tagtctcaaa agg                            33

<210> SEQ ID NO 97
<211> LENGTH: 46
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 97
tattaccaaa aatagaaaat tagagagtca cttttagtaa cacatg              46

<210> SEQ ID NO 98
<211> LENGTH: 44
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 98
tgttactaaa agtgactctc taattttcta ttttggtaa tagg                 44

<210> SEQ ID NO 99
<211> LENGTH: 35
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 99
gctcacagat cgcatctgaa ataaaataca tcatg                          35

<210> SEQ ID NO 100
<211> LENGTH: 33
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 100
atgtatttta tttcagatgc gatctgtgag cgg                            33

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 101
ctcaaaaggc attcaagtta                                              20

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 102
ttggtaatag gcattcaagt ta                                           22

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 103
tgagcggcat tcaagtta                                                18

<210> SEQ ID NO 104
<211> LENGTH: 48
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 104
gggttcccta agggttggag atgtttctct gcaaacttgg agatgtct               48

<210> SEQ ID NO 105
<211> LENGTH: 50
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 105
gggttcccta agggttggag atgaggcatg tcaatgaact taaagactca             50

<210> SEQ ID NO 106
<211> LENGTH: 46
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 106
gggttcccta agggttggac agggaagagt actttgttat cagctt                 46

<210> SEQ ID NO 107
<211> LENGTH: 50
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 107
gggttcccta agggttggag atcagggaag agtactttgt tatcagcttt         50

<210> SEQ ID NO 108
<211> LENGTH: 28
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 108
caccacgcat gcggctgcgc gaggaatc                                 28

<210> SEQ ID NO 109
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 109
cacctctaga ctcatggatg tcagaagctg                               30

<210> SEQ ID NO 110
<211> LENGTH: 46
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 110
tattaccaaa aatagaaaat tagagagtca cttttagtat gccatg             46

<210> SEQ ID NO 111
<211> LENGTH: 44
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 111
gcatactaaa agtgactctc taattttcta tttttggtaa tagg               44

<210> SEQ ID NO 112
<211> LENGTH: 22
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 112
ttggtaatag gcattcaagt ta                                       22

<210> SEQ ID NO 113

```
<211> LENGTH: 49
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 113
gggttcccta agggttggag cttgctagac caataattag ttattcacc              49
```

MULTIPLEX LIGATABLE PROBE AMPLIFICATION

CROSS-REFERENCE TO RELATED APPLICATIONS

This is a continuation application of PCT/EP01/01739 filed Feb. 15, 2001, which PCT application claims priority of European patent application number 00200506.4 filed Feb. 15, 2000, both herein incorporated by reference.

FIELD OF THE INVENTION

The invention relates to the field of biotechnology. In particular, the invention relates to a method according to the preamble of claim 1, to nucleic acid probes for use in the said method and to a kit for performing the said method.

BACKGROUND OF THE INVENTION

Detection of specific nucleic acids in a sample has found many applications. One of these applications is the detection of single nucleotide substitutions in genes. Single nucleotide substitutions are the cause of a significant number of inherited diseases and/or may confer a greater susceptibility to display a certain phenotype such as a disease or an infliction. Detection of nucleic acid sequences derived from a large variety of viruses, parasites and other micro-organisms is very important in medicine, the food industry, agriculture and other areas.

The relative quantification of specific nucleic acid sequences has important applications but is more complex and is therefore not routinely performed. One application of the relative quantification of DNA sequences is detection of trisomies such as Down's syndromes which is due to a trisomy of chromosome 21. In cancer cells deletions or amplifications of specific chromosomal areas often occur. Analysis of these can provide important information needed for optimal treatment. One example is amplification of the ERBB2 (Her-Neu) region on human chromosome 17 which defines a specific class of breast tumors requiring treatment different from other breast cancers. Detection of mutations as well as deleted or amplified chromosomal area's can potentially be used to distinguish benign and malignant tumors in small micro-biopts and can provide a fingerprint of a tumor for clonality analysis. Relative quantification of mRNAs is studied for many different reasons among which improved classification and molecular characterisation of tumors. Relative quantification of cytokine mRNAs from in vitro stimulated blood samples can potentially be used to characterise immune responses.

Many methods are known for the detection of specific nucleic acids in a sample. The most sensitive methods currently available rely on exponential amplification of the nucleic acid(s) to be detected e.g. with the use of the Polymerase Chain Reaction (PCR), Ligase Chain Reaction (LCR) or the self-sustained sequence amplification (3SR).

In PCR, nucleic acid oligomers are provided to the sample to enable priming of nucleic acid synthesis on specific sites on the nucleic acid. Subsequently the nucleic acid sequence between the two amplification primers is amplified through successive denaturation, hybridisation and nucleic acid polymerisation steps.

Detection of an amplified nucleic acid, a so-called amplicon, can occur in many different ways. Non-limiting examples are size fractionation on a gel followed by visualisation of nucleic acid. Alternatively, specific amplified sequence can be detected using a probe specific for a part of the amplified sequence.

When it is not, or only superficially, known what sequences to look for in a sample, it is advantageous to use a strategy in which a large variety of different sequences can be detected in a single test. When this so-called multiplex amplification is used to determine the relative abundance of various target nucleic acid in the original sample, it is particularly important that the difference in the number of amplified molecules per amplicon is correlated to the difference in the number of target sequences per amplicon in the sample.

To ensure this correlation, a bias in the amplification of sequences not due to a difference in the relative abundance of target nucleic acids in the sample should be avoided as much as possible.

Multiplex nucleic acid amplification methods can be divided in methods in which one amplification primer pair is used for all fragments to be amplified such as RAPD, AFLP and differential display techniques, and methods using a different amplification primer pair for each fragment to be amplified. The currently available amplification techniques using only one primer pair for all fragments to be amplified are typically used to amplify a random subset of the nucleic acid fragments present in a sample. It is not uncommon that more than 50 fragments are amplified in one reaction using these techniques. It has been shown by Vos et al.(1995), Nucleic Acid Research 23, 4407-14 that the Polymerase Chain Reaction as used in AFLP is capable of amplifying large numbers of unrelated fragments with almost equal efficiency provided that these fragments can be amplified with the same set of PCR primers. Relative amounts of amplification products obtained by AFLP can be used to determine relative copy number of specific fragment sequences between samples.

Multiplex methods for the amplification of specific targets typically use a different primer pair for each target sequence to be amplified. The difference in annealing efficiency of different primer pairs result in a strong bias in the amplification of the different amplicons thereby strongly reducing the fidelity of a quantitative multiplex assay. Furthermore the presence of a large number of different primers results in a strongly increased risk of primer dimer formation diminishing the possibility of reproducible amplifying small amounts of target nucleic acids. Amplification of more than 10 specific nucleic acid fragments in one test is therefore not recommended in the art and usually leads to unreliable results.

The method of the preamble is known from e.g. WO 96/15271 (herein incorporated by reference), providing a method for copying and detecting sequence information of a target nucleic acid present in a sample, into a well characterised DNA template. The method comprises hybridising up to 5 different probe sets of single stranded first and second DNA probes to a target nucleic acid wherein the first and second probe, after hybridisation to the target sequence and subsequently ligation of the probes are used as a template for amplification. The method is suited for the copying of sequence information of RNA or DNA into a DNA template. Said first and/or said second probe further comprises a tag which is essentially non-complementary to said target nucleic acid. The tags are used for the priming of nucleic acid synthesis in the amplification reaction. Such tag can also be used for detection of the resulting amplicon. Thus, said amplification is initiated by binding of a nucleic acid primer specific for said tag. A bias due to difference in primer sequences is avoided by including into the copying action a nucleic acid tag to which amplification primers are directed. Thus, for the analysis of nucleic acid in a sample the sample is provided with one or more DNA probes wherein said probes comprise a first nucleic acid tag and a second nucleic acid tag, optionally denaturing nucleic acid in said sample, incubating said sample to allow hybridisation of complementary nucleic acid in said sample, functionally separating hybridised probes from non-hybridised probes, providing said hybridised probes with at least a first primer, complementary to said first tag, and a second oligomer primer, complementary to said second tag, amplifying at least part of said DNA probes after hybridisation and analysing the amplificate for the presence of amplified products.

Said first and said second probe can only be amplified exponentially by e.g. PCR when the probes are connected. Since connection can essentially only take place when the probes are substantially adjacent to each other, exponential amplification, and thereby detection of the amplicon is only possible if said first and said second probe where hybridised to the target nucleic acid. Non hybridised probes are not exponentially amplified. Removal of non-hybridised and non-ligated probes is therefore not essential, and the reactions can be carried out in the same reaction vessel. Dependent on the temperature, buffer-conditions, ligase-enzyme and oligonucleotides used, the difference in ligation efficiency of oligonucleotides that are perfectly matched to the target nucleic acid and mismatched oligonucleotides can be very large providing increased possibilities to discriminate closely related target sequences.

A similar method is known from WO 97/45559. Both prior art methods however suffer from serious limitations preventing their use for the detection and relative quantification of more than 5 specific nucleic acid target sequences in a single "one-tube" assay in an easy to perform and robust test with unequivocal results using only a small amount of a nucleic acid sample.

The above identified prior art methods were derived from the Ligase Chain Reaction (LCR; Barany F., Proc.Natl.Acad.Sci.USA, 88:189–93 (1991). In fact, these previous art methods are designed to use two consecutive amplification reactions, starting with several cycles of LCR. In LCR very short hybridisation reactions and therefore high probe concentrations are used. The ligation and amplification reactions are performed in the same reaction vessel, i.e. without sample immobilisation and without removal of non-ligated probe molecules and buffer constituents. All probe oligonucleotides used in the ligation reaction remain therefore present during the amplification reaction. One of the tags used for amplification which is present at the 3' end of one of the two probe oligonucleotides is however complementary to one of the PCR primers and will therefore provide a template for primer elongation during the PCR reaction. These unligated probe molecules only contain one of the two tags used in the PCR reaction and can therefore not be amplified exponentially but only linearly. During each PCR cycle each picomole of probe will consume one picomole of one of the PCR primers. For each probe pair present, the probe amounts used in the art, 200–500 femtomoles (WO97/45559) of each probe, 750–1500 femtomoles (WO96/15271) or 160 fmoles (WO 98/04746) will consume 5–45 picomoles of one of the PCR primers during the 25–30 PCR cycles that are needed when nanogram amounts of human nucleic acids are being analysed. The use of more than 10 probes simultaneously requires, apart from the amounts necessary for exponential amplification of ligated probes, PCR primer amounts in excess of 50 pMoles for the linear amplification of unligated probes (that are not removed, but still present in the reaction mixture) which results in strongly increased amounts of aspecific amplification products. The multiplex methods in the art are therefore limited to the use of a maximum of 5–10 probes per detection reaction. In related previous art methods even higher probe concentrations are used. In WO 98/37230, 5000 femtomoles of each of three probe oligonucleotides is used. In WO 97/19193, 3200 femtomoles probe are used in each assay. These previous art methods are therefore not suitable for multiplex detection of several probes. The high probe amounts used in the previous art reduces the number of probes that can be used simultaneously as well as the sensitivity of the assay.

SUMMARY OF THE INVENTION

According to the present invention, this serious limitation is solved by using probe amounts more than one order of magnitude lower than described in the previous art. Thereto, the invention is characterized in that the amount of at least the first probe of at least one probe set in the mixture is less than 40 femtomoles, and the molar ratio between the said first primer and the first probe being at least 200. The use of such substantial low probe amounts and a relatively high molar ratio between the first primer and the first probe also solves the problem of false positive signals due to extension of the probes having the target specific sequence at their 3' end when hybridized to the target sequence during the PCR reaction, followed by elongation of the complement of the second target specific probe on these extension products as described in detail in WO97/45559A and U.S. Pat. No. 6,027,889 (both herein incorporated by reference).

A consequence of this reduced probe amount is that hybridisation reactions are slower. In the examples provided herein hybridisation reactions typically are performed for 16 hrs. This can be reduced by inclusion of certain chemicals and/or proteins in the reactions as is well known in the art. Previous art methods using, or being derived from LCR reactions use typical hybridisation treatments of 1–5 minutes (WO 97/45559).

Further, by using a low probe amount according to the invention, a plurality of probe sets can be used in the invention for detecting one or more specific nucleic acid sequences, without the above-mentioned drawback that the probes are significantly consumed by amplification of unligated probes. In order to detect a plurality of different target nucleic acid sequences, the first probes from the probe sets, specific for hybridising to the corresponding nucleic acid sequences and containing a tag complementary to one of the amplification primers, are present in the mixture in the above-mentioned amount.

Preferably, the amount of at least the first probe of each probe set in the mixture is less than 40 femtomoles, the molar ratio between the first primer and the first probe being at least 200. The probe sets differ from one another in that at least one of the probes of different probe sets have different target specific regions, therewith implicating that each probe set is specific for a unique target nucleic acid sequence. However, probe sets may only differ in one of the probes, the other probe(s) being identical. Such primer sets can e.g. be used for the determination of a specific point mutation or polymorphism in the sample nucleic acids.

The molar ratio between the first primer and the first probe is preferably at least 500, more preferably at least 1000, and most preferably at least 2000. The higher the said ratio, the more different primer sets for the detection of a corresponding number of different amplicons can be used. However, as indicated above, unspecific amplification reactions as a result of high primer concentrations is to be avoided. Thereto, the primer concentration preferably is below 50 pMoles, more preferably below 20 pMoles in a reaction volume of 10–100 µl.

Preferably, the molar amount of at least the first probe of at least one probe set, preferably of a plurality of probe sets, more preferably of each probe set in the mixture is less than 10 femtomoles, preferably 4–5 femtomoles. By such low probe amounts, reliable amplification of up to 40 different sets of probes can be achieved. In a multiplex assay as described in examples 12–14, 4 femtomoles each of 40 different probe pairs is used in one assay on 5–100 ng amounts of human chromosomal target DNA. During the at least 30 PCR cycles of the amplification reaction 30×4×40=4800 femtomoles of one of the PCR primers is consumed by linear amplification of unligated probes corresponding to 48% of the available 10 picomoles PCR primer.

Preferably, the probes of the same probe set are present in the mixture in substantially equal amounts, although the said amounts can differ from one another, e.g. dependent on the hybridisation characteristics of the target specific regions with the target nucleic acid sequence. However, the amount of second probe may optionally be a factor 1–5 higher than that of the corresponding first probe, without negatively affecting the reaction.

Although it is possible for the first probe of different probe sets to have different tag sequences, implicating that a plurality of different first primers are to be used in the amplification step it is highly preferred that the first tag sequences of the first nucleic acid probes of the different probe sets are identical, so that only one first primer has to be used in the amplification reaction. A bias in the amplification due to a difference in the sequence of different primers used for the amplification can thus be completely avoided, resulting in a substantially uniform amplification for all probe assemblies. According to the invention it is however also possible that a number of first nucleic acid probes comprise the same tag sequence, whereas first probes belonging to another probe set may comprise another first tag sequence.

In a preferred embodiment, the amplification step comprises binding of a second nucleic acid primer, specific to the second tag sequence, to the elongation product of the first primer. By the use of a second primer, the amplification reaction is not linear, but exponential. Said first and said second probe preferably each comprise a different tag. Preferably said amplification of connected probes is performed with the use of the Polymerase Chain Reaction (PCR).

For the same reasons as discussed above, the molar ratio between the second primer and the second probe is preferably at least 200, more preferably at least 500, even more preferably at least 1000 and most preferably at least 2000.

In line with the above, preferably the second tag sequences of the second nucleic acid probes of the different probe sets are identical, so that for amplification of the primer assemblies a limited amount of different primers may be used. In this way, amplification of all possible primer assemblies can be accomplished using a limited number of primer pairs, preferably only one primer pair. As in such a case, all the probes comprise the same first tag and the same second tag, thereby excluding any bias in the amplification of the probes due to sequence differences in the primers.

In order to prevent competition during a PCR reaction between probe and primer binding in case a single second primer is used in the reaction mixture, the molar ratio between the second primer and the total amount of second probes present in the reaction mixture is preferably at least 5, more preferably at least 15 and most preferably at least 25.

However, it is of course possible to use probes that comprise different first tags and/or different second tags. In this case it is preferred that the primers are matches for similar priming efficiencies. However, some bias can be tolerated for non quantitative applications or when the bias is known, it can be taken into account in a quantitative application.

Because of the low amounts of probes present in the reaction mixture, the number of different probe sets in one reaction may exceed the maximum number of probe sets that can be achieved with the multiplex methods known in the art. The reaction mixture preferably comprises at least 10 probe sets, preferably at least 20 and most preferably 30–40 different sets of probes. It is to be understood that it is preferred to use lower probe amounts when the number of different probe sets increases. Using e.g. 10 different probe sets, the amount of each first probe is preferably less than 20–40 femtomoles, whereas when 30–40 different probe sets are used, the amount of each different first probe is preferably in the range of 1–8 femtomoles in the reaction mixture.

As indicated above, the presence of a second, or further additional, distinct target nucleic acid can be detected with the method according to the present invention. To enable this it is preferred that said sample is provided with at least two probe sets, i.e. the target specific regions of at least one of the first, second, or, when present, the third probes of each set differ from one another. In this case at least two different amplicons can be detected. For instance when a first or said second nucleic acid probe of a probe set is capable of hybridising to target nucleic acid essentially adjacent to a probe of the second probe set. Successful connecting of probes can then result in an amplicon resulting from the connection of said first and said second probe of the first set and an amplicon resulting from the connection of the first and second of the second set. It should be understood that in the above-mentioned case, one of the probes of the first and second set may be identified. This embodiment of the invention has applications in the detection of for instance SNPs which are different in only one nucleotide. One can choose for instance a first probe set comprising a first probe capable of hybridising to a common target nucleic acid sequence adjacent or in close proximity to the site of the SNP and a second capable of hybridising to the site adjacent to the first probe. A second probe set can simultaneously be used comprising the same first probe as in the first probe set, and a second probe differing from the second probe of the first probe set in the nucleotide at the site of the SNP. In case both second probes are present at the same concentration and are both able to hybridise to the target nucleic acid sequence under the incubation conditions used, half of the target nucleic acids will hybridise to probes of the first probe set and the other half will hybridise to probes of the second probe set. One can than exploit the difference in ligation efficiency between perfectly matched and mismatched probes in order to determine the nucleotide present at the site of the SNP. At a certain target molecule the second probe of either the first or second probe set will have a mismatch at the site of the SNP which strongly reduces the enzymatic or chemical ligation efficiency and thereby reduces the formation of the corresponding amplicon in the amplification reaction.

If both SNP alleles are present both amplicons will be formed. These can be distinguished by length if the second probes of probe sets 1 and 2 differ not only at the site of the SNP but also by the length of the sequence between the PCR tag and the end of the probes for instance by the introduction of a small stuffer sequence between the hybridising sequence and the PCR tag in one of both probes. Probes were made for the detection of polymorfisms in the human TNF gene. Although approximately 40% of the probe pairs worked excellent and gave band of almost identical peak areas on DNA samples from heterozygotes, it was noted that the amplification reaction often resulting in a preferred amplification of one, most often the smallest, amplicon.

As the two amplicons in this particular embodiment have an almost identical sequence, not only homoduplexes but also heteroduplexes will be formed during the final part of the amplification reaction. We discovered that the incorporation of small non-identical stuffer sequences between the hybridising sequence and the PCR tag in both the second and third probe diminished this bias in amplification efficiency. Preferably these non-identical stuffer regions do have the same nucleotide immediately adjacent to the primer tag sequence. During later stages of the PCR reaction a competition takes place between primer-binding/elongation and duplex formation of the amplicons. If a heteroduplex is formed between strands at which a PCR primer is already annealed, the PCR primer will not be as easily be displaced when a short mismatch region is present immediately adjacent to the PCR primer binding site.

In practice one often would need to further provide said sample with an additional probe pair, having different first and second probes, complementary to a different target nucleic acid. Thus resulting in a possible detection of an amplicon resulting from the connection of the first and second probe of the first primer set and an amplicon resulting from the first and second probe of the additional primer set. For enabling detection of each additional target nucleic acid one can similarly provide one or two additional probes. This has applications for the detection and relative quantification of more than one target nucleic acid which need not be in the same chromosomal region.

To allow connection of essentially adjacent probes through ligation, the probes preferably do not leave a gap upon hybridisation with the target sequence. In that case the first and second segments of the target nucleic acids are adjacent. However, it is also possible that between the first and second segments a third segment is located on the target nucleic acid. In that case a third probe may be provided in a probe set complementary to the third segment of said target nucleic acid, whereby hybridisation of the third probe to said third segment allows the connecting of the first, second and third probes. In this embodiment of the invention a gap upon hybridisation of the first and second probes to the target nucleic acid is filled through the hybridisation of the third probe. Upon connecting and amplification, the resulting amplicon will comprise the sequence of the third probe. One may choose to have said interadjacent part to be relatively small thus creating an increased difference in the hybridisation efficiency between said third segment of the target nucleic acid and the third probe that comprises homology with said third segment of said target nucleic acid, but comprises a sequence which diverges from the perfect match in one or more nucleotides. In another embodiment of the invention a gap between first and second probes on said target nucleic acid is filled through extending a 3' end of a hybridised probe or an additional nucleic acid filling part of an interadjacent part, prior to said connecting. Applications for this particular embodiment include the determination of the breakpoint sites in chromosomal translocations.

Preferably at least a portion of the probes, not hybridised in the incubation step are not removed in the course of the method according to the invention and remain in the reaction mixture together with the hybridised probes.

In the method of the present invention, reaction conditions are used that do not require unligated probe removal or buffer exchange With "portion" an amount of probes is meant above trace-level that may remain present when the reaction is subjected to a treatment for complete separation of hybridised probes from unhybridised probes. Preferably, said portion is at least 5% from the unhybridised probes, more preferably 10% or more.

In several multiplex methods in the art, such as WO98/04746, immobilisation of sample nucleic acids is required in order to exchange buffer solutions and remove non target bound probe molecules. Hybridised probes can be separated from non-hybridised probes in a number of different ways. One way is to fix sample nucleic acid to a solid surface and wash away non-hybridised probes. Washing conditions can be chosen such that essentially only hybridised probes remain associated with the solid surface. The hybridised probes can be collected and used as a template for amplification. According to WO98/04746, probe separation was accomplished by addition of a tagged third target specific oligonucleotide.

It is preferred not to remove any of the unhybridised probes from the reaction mixture, i.e. that all unhybridised probes remain in the reaction mixture during the incubation step, the connecting step and the amplifying step. It is however possible to remove a portion of the unhybridised probes from the mixture if desired. The skilled person is aware of suitable methods for such partial removal. By not removing any of the unhybridised probes from the reaction mixture, the method according to the invention provides the possibility for an essential one-tube assay using more than 5 probes simultaneously and less than 10.000 copies of each target nucleic acid for each assay.

It is very attractive for the method to be carried out as a "one tube" assay; i.e. the contacting step, the connecting step and preferably also the amplification step are carried out in the same reaction vessel, the reaction mixture not being removed from the said vessel during the said steps.

The contacting, incubation and connecting step are usually carried out in a relatively small volume of 3–20 μl, although larger volumes, as well as increase of volume of the reaction mixture in subsequent reaction steps are tolerated. The amplification step is usually performed in a larger volume of 20–150 μl; for this, the optionally smaller volume of the reaction mixture in the connection step is usually completed to the desired volume for the amplification by adding the additional ingredients for the amplification reaction. In particular, in a typical reaction mixture of 3–150 μl, the the amount of: sample nucleic acid is 10–1000 ng, the first probe of each probe set is 0.5–40 fmol, the second probe of each probe set is 0–40 fmol, each first primer is 5–20 pmol, each second primer is 0–20 pmol.

In case that probe sets comprise a second probe, the amount of the second probe is 0.5–40 fmol; in case a second primer is used for the amplification reaction, the amount of the said second primer is preferably 5–20 pmol.

Another limitation of previously described ligation dependent amplification methods is that the ligation reaction was performed at low temperatures not permitting sufficient hybridisation selectivity for use on complex nucleic acid samples or that thermostable ligases were used that cannot easily be inactivated before the start of the amplification reaction. In a preferred embodiment of the current invention said ligation is performed with a thermostable nucleic acid ligase active at temperatures of 50° C. or higher, but capable of being rapidly inactivated above approximately 95° C. Once probes are connected it is preferred that essentially no connecting activity is present during amplification since this is not required and can only introduce ambiguity in the method. Since amplification steps usually require repeated denaturation of template nucleic acid at temperatures above 95° C. it is preferred to remove the connecting activity through said heat incubation. In order to prevent hybridisation of probes to sequences only partially complementary it is preferred to perform the ligation reaction at temperatures of at least 55° C. The present invention therefore in one aspect provides a method wherein ligation of probes annealed to a target nucleic acid is performed by a thermostable nucleic acid ligation enzyme, i.e. with an activity optimum higher than at least 50° C., under suitable conditions, wherein at least 95% of the ligation activity of the said ligation enzyme is inactivated by incubating said sample for 10 minutes at a temperature of approximately 95° C.

Another important limitation of the prior art is that only synthetic production of oligonucleotides is used. Synthetic produced oligonucleotides are cheap, essentially pure and are available from many suppliers. Synthetic production of long oligonucleotides has however serious limitations. The length of the complementarity region with the target nucleic acid in the probe is preferably long enough to allow annealing at elevated temperatures. Typically the length of the complementarity region is at least 20 nucleotides. The probes also contain a tag which can be of any size, however, typically a tag comprises a nucleic acid with a length of at least 15 nucleotides. A probe comprising a tag therefore typically comprises a length of 35 or more nucleotides. Amplicons of connected first and second probes typically have a length of at least 70 nucleotides. This minimum length is also preferred to discriminate amplicons from primer dimers and other side products that are often formed in PCR reactions in which only very small amounts of starting template are used.

A problem, particularly encountered in multiplex amplifications, is the discrimination of the different amplicons that can result from the amplification. Discrimination can be achieved in a number of different ways. One way is to design the multiplex amplification such that the size of each amplicon that can occur, is different. Size fractionation on for instance a gel and determination of the size of the detected amplicon then allows discrimination of the various amplicons. Alternatively, amplicons can be discriminated between on the basis of the respective sequences present in the amplicon. For instance through hybridising amplicons to specific probes. However, the latter method has the disadvantage that additional steps need to be included to detect and/or discriminate the amplicons. In the examples illustrating the present invention therefore the various amplicons were discriminated on the basis of size.

However, the discrimination of amplicons which differ only slightly in size is difficult. For optimum quantification of peaks in an electropherogram a size difference between different amplicons of at least 4 nucleotides is preferred. On the other hand longer probes, to allow more differences in size of the resulting amplicons, are not very easily synthesised synthetically. For proper discrimination of a plurality of different amplicons, preferably at least 10, more preferably at least 20 and most preferably 30–40 different amplicons on the basis of size and for optimal quantitation of amplicons, at least one of the probes of a number of amplicons is more than 50–60 nucleotides in size. Oligonucleotides longer than 60 nucleotides however typically suffer from less yield, lower purity and the reliability of the sequence of the probe becomes a problem. Chemically synthesised oligonucleotides are made stepwise in a 3'–5' direction. Coupling yield for each nucleotide is usually only 98.5%, resulting in the presence of a large number of different side products. Besides there is a risk on damaging the already synthesised part of the oligonucleotide during each new cycle of chemical polymerisation. A high reliability of the sequence of a probe is particularly important when already one false nucleotide can give false results.

In an attractive embodiment of the invention, this problem is overcome by utilising at least one probe comprising nucleic acid that is generated through enzymatic template directed polymerisation, at least prior to the hybridisation step. In this embodiment, the above-discussed probe amounts and relative primer-to-probe ratios are preferred. Enzymatic template directed polymerisation can be achieved for instance in a cell. It is preferably achieved through the action of a DNA polymerase, RNA polymerase and/or a reverse transcriptase. Such enzymatic template directed polymerisation is capable of generating large stretches of nucleic acid with a high fidelity, thereby enabling the generation of a reliable probe, that is substantially larger than currently reliably possible with the synthetic methods. A probe comprising nucleic acid that is generated through enzymatic template directed polymerisation is in the present invention further referred to as an enzymatic probe.

Using at least one enzymatic probe it is possible to increase the size differences between the various amplicons.

Size differences can be generated by increasing the length of the hybridising region of a probe or by introduction of a stuffer region that is not complementary to the target nucleic acid. By varying the size of the stuffer one can easily design probes that comprise the same hybridisation capacity (wherein the length of complementarity region with the target nucleic acid and the CG/AT content are adjusted to each other), while still being able to discriminate the resulting amplicons by size. Another advantage of non-hybridising stuffer sequences is that stuffer sequences with known amplification characteristics can be selected. Certain DNA sequences have a lower amplification efficiency in amplification reactions for instance due to polymerase pause sites such as hairpins. Stuffer sequences provide the possibility to use long amplification products while knowing that a major part of the probe has good amplification characteristics. In SNP/mutation screening the use of a short hybridising region in combination with a non-hybridising stuffer sequence provides the possibility to simultaneously use probes for SNP's or mutations that are close to each other without competition between probes during the hybridisation reaction while still using the advantages of long amplification products. This is also a great advantage in mRNA quantification as only a small (50–80) nucleotide cDNA fragment is needed for binding of probes, reducing the chance of reverse transcriptase pause sites or RNA breakdown influencing the results obtained. Finally the stuffer can of course also be used to introduce a tag, for instance for later discrimination of probe amplification products on the basis of stuffer sequence. In one aspect of the current invention a series of cloning vectors each containing different stuffer sequences is provided.

In a preferred embodiment of the invention, one of the probe oligonucleotides is generated by digestion of DNA, in particular plasmid, phage or viral DNA with a restriction endonuclease (also referred to as "restriction enzyme"). In a further preferred embodiment of the invention one of the probe oligonucleotides is obtained by restriction enzyme digestion of single stranded phage DNA that is made partially double-stranded by annealing of short oligonucleotides. The use of single stranded phage or phagemid DNA increases the effective probe concentration during hybridisation and reduces the amount of probe DNA present as well as the possibility of non-specific amplification products formed e.g. by elongation of one of the PCR primers or one of the short probe oligonucleotides at (partially) complementary sequences of the complementary probe oligonucleotide. In a further preferred embodiment the restriction enzyme is capable of cutting at least one strand of the DNA outside the enzyme recognition site sequence on said DNA, resulting in DNA fragments not containing any residues of the restriction enzyme recognition sequence at their ends. Digestion means cleavage of both or only one strand of a double stranded DNA, such as e.g. cleavage by the restriction enzyme BsmI.

Advantageously, the DNA used is single stranded DNA made partially double stranded by annealing one or more oligonucleotides.

In another attractive embodiment of the invention at least one probe comprises two separate probe parts being connected together in the step of connecting the essentially adjacent probes. "Probe parts" are herein defined as two nucleic acid sequence stretches that, once linked together, make up the probe. Said stretches may be of different length. Preferably, at least one of said probe parts comprises enzymatic template directed polymerised nucleic acid prior to said connecting. This embodiment can in one aspect be used to add a stuffer to the probes, resulting in a larger amplicon, whereas not all of said at least one probe needs to be generated through enzymatic template directed polymerisation prior to said connecting. This embodiment is elucidated in FIG. 12 below.

Further to the above, one of the applications of the current invention is the analysis of RNA. Non limiting examples are the relative quantification of mRNAs and SNP analysis of RNA viruses including the class of retroviruses. Direct detection of RNA sequences is not preferred as there is no thermostable ligase known acting on DNA-RNA duplexes. Furthermore RNA is extremely prone to degradation during the long incubations required for complete hybridisation of probes. When the target nucleic acid comprises RNA than one way to copy sequence information of the target nucleic acid into a DNA template is by using a reverse transcriptase. This retrovirus derived enzyme is capable of generating a DNA strand using RNA as a template. A drawback of using reverse transcriptase is however, that it is an enzymatic process that is susceptible to secondary structures in the template RNA. Moreover, reverse transcriptase activity is notoriously difficult to standardise when long sequences are copied thereby reducing the reliability of an amplification strategy. In one aspect, the present invention provides alternative means and methods to generate amplicons substantially longer than 80 nucleotides while needing only 80 nucleotides or less copy sequence of the RNA target.

A further application of the current invention is the detection of pathogens in a sample. There are many different pathogens that can contaminate food samples or be present in clinical samples. Determination of even minor quantities of a pathogen can be accomplished using nucleic acid amplification methods such as PCR, RT-PCR and 3SR. However, for these purposes, considering the wide variety of potential pathogens, a large number of different primer sets need to be used and their performance optimised. Although possible, this is a lengthy process. In addition, very often not all primer sets can be added in one reaction mix thus necessitating different reactions for full coverage of the potential pathogens. With the present invention it is possible to scrutinise the presence or absence of a large number of different pathogens in a sample. This can be accomplished by analysing RNA or DNA in a sample.

As much is known of the sequence of the tRNA's and ribosomal RNA's of different species, this information may be used to design oligonucleotides that will be aligned on either (cDNA of) these abundant RNA species, or the DNA coding for them. The resulting ligation finger-print may provide enough information to identify the specific strain or species from which the nucleic acid was derived. Due to the high copy number of tRNA's and ribosomal RNA molecules, sensitivity of detection techniques can be extremely high.

In another aspect, the invention further provides a nucleic acid probe for use in a method of the invention, the probe comprising enzymatic template directed polymerised nucleic acid.

In another aspect the invention provides a mixture of nucleic acids comprising two or more probes, at least one of these comprising enzymatic template directed polymerised nucleic acid.

In another aspect the invention provides a nucleic acid probe set for use in the current invention wherein the probes are capable of hybridising to adjacent sites on a DNA sequence which is complementary to a naturally occurring mRNA but having essentially separated target sequences on chromosomal DNA. Such a probe pair is specific for the detection of a cDNA sequence, as will be explained in more detail below.

In yet another aspect the invention provides a kit for performing a method of the invention, comprising a liquid medium containing at least one probe in a concentration of 20 nM or less. With such a kit, the probes are provided in the required low amount to perform reliable multiplex detection reactions according to the present invention.

In another embodiment, a kit for performing the method according to the invention is provided, the kit comprising a nucleic acid probe comprising enzymatic template directed polymerised nucleic acid, or a probe mixture comprising at least one of such probes.

In still another aspect, the invention provides a kit comprising a thermostable ligation enzyme of the invention, optionally further comprising a nucleic acid probe and or a mixture of probes according to the invention.

In still another aspect the current invention provides a series of related viral or plasmid cloning vectors that can be used to prepare probes for use in the current invention and having different stuffer sequences.

In the current invention not the target nucleic acids present in the sample are amplified, but (ligated) oligonucleotide probes provided to the sample. Target nucleic acid sequences originally found in the sample being analysed are not amplified because such target sequences do not contain amplification primer-specific tags.

Although the preferred embodiment of the invention uses the polymerase chain reaction for amplification of the probes used, other amplification methods for nucleic acids such as the 3SR and NASBA techniques are also compatible with the current invention.

An outline of the method described in the current invention is shown in FIGS. 1–3.

The method described herein is referred to as Multiplex Ligatable Probe Amplification (MLPA).

BRIEF DESCRIPTION OF THE DRAWINGS

FIGS. 1, 2 and 3 show graphic outlines of the MLPA invention.

FIG. 4 shows a graphic outline of a M13 clone used to prepare the long probe oligonucleotides.

FIG. 5 shows a simplified way of performing MLPA with the use of agarose gels for the detection of amplicons.

FIGS. 6–11 show the application of the MLPA invention for the detection of mRNA's.

FIG. 6: Detection of mRNA's.

FIG. 7: Detection of cDNA made with the use of oligo-dT as a reverse transcriptase primer.

FIG. 8: Detection of cDNA made with the use of gene specific reverse transcriptase primers.

FIG. 9: The use of tagged reverse transcriptase primers.

FIG. 10: The use of sequence tagged reverse transcriptase primers.

FIG. 11: The use of reverse transcriptase primers that are part of one of the probes.

FIG. 12 shows the use of the MLPA invention without the use of target specific clones.

FIG. 13 shows an alternative way of performing the MLPA invention.

FIG. 14 shows the use of "viagra"13 oligonucleotides to reduce internal secondary structures of the probes.

FIG. 15 shows an outline of the MLPA invention with the use of complete probes made by PCR.

FIGS. 21 and 22 show alternative ways of performing the MLPA invention.

FIG. 23 shows the use of MLPA for the detection of the breakpoint site in chromosomal rearrangements.

FIG. 24 shows a list of genes towards which the probes used in example 12 and shown in FIGS. 25 and 26 were directed.

FIGS. 26A, 27B and 27C show separation profiles of MLPA amplification products obtained on three DNA samples.

FIG. 27 shows a comparison of relative fluorescence ratios of amplicons from selected probes used in example 12.

Figure 16:
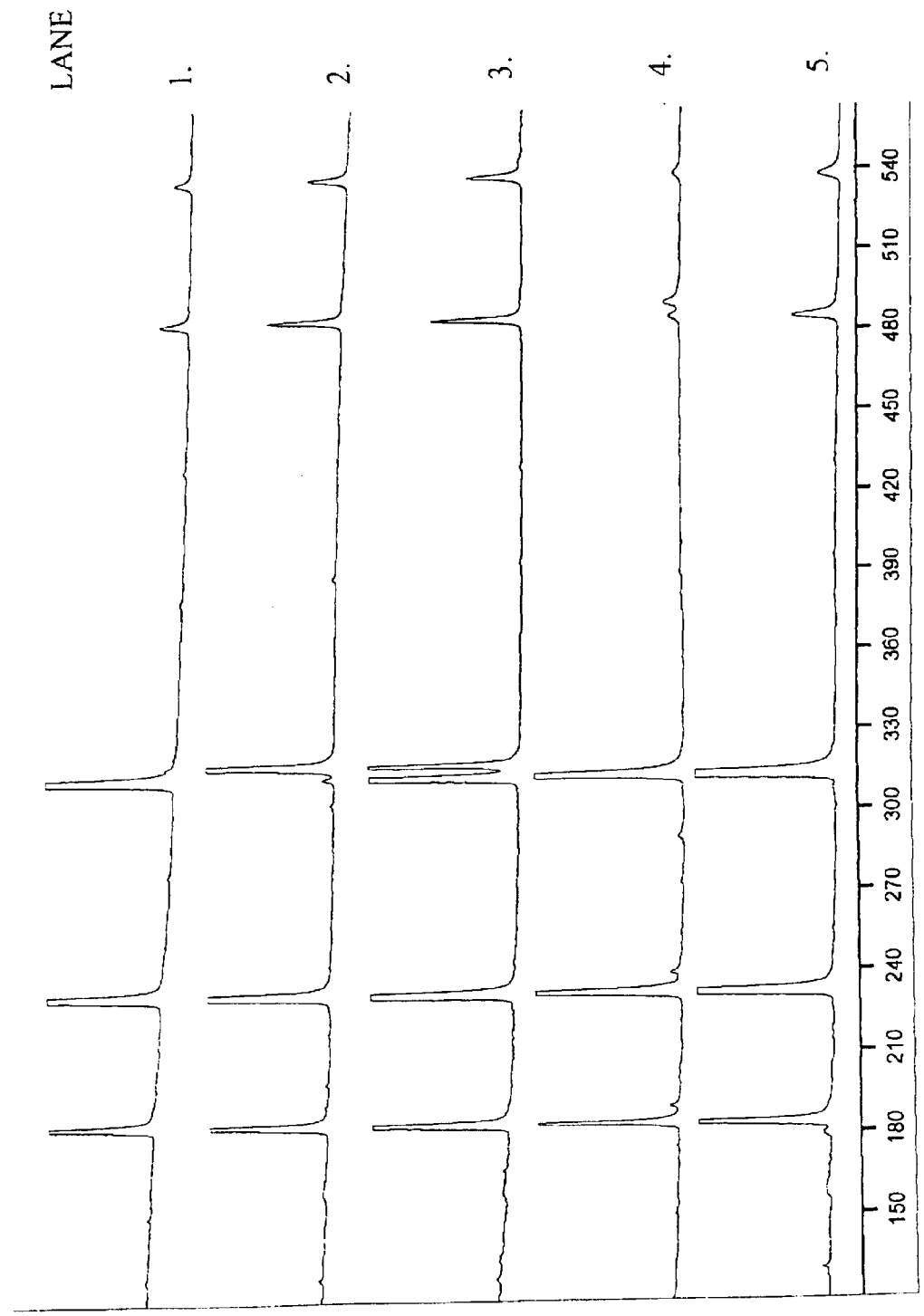
FIGS. 16 and 17 show the results of the MLPA invention for the analysis of the human CFTR gene.

As used herein, the term "DNA polymorphism" refers to the condition in which two or more different nucleotide sequences can exist at a particular site in the DNA.

A complementary nucleic acid is capable of hybridising to another nucleic acid under normal hybridisation conditions. It may comprise mismatches at a small minority of the sites.

As used herein, "oligonucleotide" indicates any short segment of nucleic acid having a length between 10 up to at least 800 nucleotides. Oligonucleotides can be generated in any matter, including chemical synthesis, restriction endonuclease digestion of plasmids or phage DNA, DNA replication, reverse transcription, or a combination thereof. One or more of the nucleotides can be modified e.g. by addition of a methyl group, a biotin or digoxigenin moiety, a fluorescent tag or by using radioactive nucleotides.

As used herein, the term "primer" refers to an oligonucleotide, whether occurring naturally as in a purified restriction digest or produced synthetically, which is capable of acting as a point of initiation of nucleic acid sequence synthesis when placed under conditions in which synthesis of a primer extension product which is complementary to a nucleic acid strand is induced, i.e. in the presence of different nucleotide triphosphates and a polymerase in an appropriate buffer ("buffer" includes pH, ionic strength, cofactors etc.) and at a suitable temperature. One or more of the nucleotides of the primer can be modified for instance by addition of a methyl group, a biotin or digoxigenin moiety, a fluorescent tag or by using radioactive nucleotides.

A primer sequence need not reflect the exact sequence of the template. For example, a non-complementary nucleotide fragment may be attached to the 5' end of the primer, with the remainder of the primer sequence being substantially complementary to the strand.

As used herein, the terms "target sequence" and "target nucleic acid" refer to a specific nucleic acid sequence to be detected and/or quantified in the sample to be analysed.

As used herein, "amplification" refers to the increase in the number of copies of a particular nucleic acid. Copies of a particular nucleic acid made in vitro in an amplification reaction are called "amplicons" or "amplification products".

As used herein, "probe" refers to a known sequence of a nucleic acid that is capable of selectively binding to a target nucleic acid. More specifically, "probe" refers to an oligonucleotide designed to be sufficiently complementary to a sequence of one strand of a nucleic acid that is to be probed such that the probe and nucleic acid strand will hybridise under selected stringency conditions. Additionally a "ligated probe" refers to the end product of a ligation reaction between a pair of probes.

As used herein, the term substantially "adjacent" is used in reference to nucleic acid molecules that are in close proximity to one another. The term also refers to a sufficient proximity between two nucleic acid molecules to allow the 5' end of one nucleic acid that is brought into juxtaposition with the 3' end of a second nucleic acid so that they may be ligated by a ligase enzyme. Nucleic acid segments are defined to be substantially adjacent when the 3' end and the 5' end of two probes, one hybridising to one segment and the other probe to the other segment, are sufficiently near each other to allow connection of the said ends of both probes to one another. Thus, two probes are substantially adjacent, when the ends thereof are sufficiently near each other to allow connection of the said ends of both probes to one another.

As used herein, the terms "detected" and "detection" are used interchangeably and refer to the discernment of the presence or absence of a target nucleic acid or amplified nucleic acid thereof or amplified probes specific for that target nucleic acid.

As used herein, the term "hot-start" refers to methods used to prevent polymerase activity in amplification reactions until a certain temperature is reached.

As used herein, the terms "restriction endonucleases" and "restriction enzymes" refer to bacterial enzymes each of which cut double-stranded DNA at or near a specific nucleotide sequence.

As used herein the term "PCR" refers to the polymerase chain reaction (Mulis et al U.S. Pat. Nos. 4,683,195, 4,683,202 and 4,800,159). The PCR amplification process results in the exponential increase of discrete DNA fragments whose length is defined by the 5' ends of the oligonucleotide primers.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "mutant" refers to a gene or gene-product having at one or more sites a different nucleic acid sequence when compared to the wild-type gene or gene product.

As used herein, "sample" refers to a substance that is being assayed for the presence of one or more nucleic acids of interest.

As used herein, the terms "hybridisation" and "annealing" are used in reference to the pairing of complementary nucleic acids.

Conventional techniques of molecular biology and recombinant DNA techniques, which are in the skill of the art, are explained fully in the literature. See, for instance, Sambrook, Fritsch and Maniatis, Molecular Cloning; A Laboratory Manual, Second Edition (1989) and a series, Methods in Enzymology (Academic Press, Inc.).

For multiplex analysis of ligation products using the length of the ligation product to identify the specific ligation products, at least one of the two oligonucleotides will have a length of more than 60 nucleotides in most (but not necessarily all) of the probes. Fragments substantially longer than 60 nucleotides are difficult to synthesise chemically in high yield and high quality. We discovered that fragments derived by restriction endonuclease digestion of plasmids, phages or phagemids are a preferred source of one of the two oligonucleotides used in ligatable probe amplification. These fragments typically contain less than one mistake in every 10.000 bp as template directed enzymatic nucleotide polymerisation occurs with high fidelity and is backed in vivo by several repair mechanisms. Alternatively fragments of a sufficient long length and having a sequence tag can be produced by in vitro enzymatic template directed nucleotide polymerisation as described in example 8. The other probe oligonucleotide to be ligated can be smaller and is most easily produced chemically. In case of SNP analysis, the SNP is preferably located on the small chemically synthesised fragment as only one phage or plasmid clone has to be produced for each SNP to be tested.

Chemically synthesised oligonucleotides are made in a 3'-5' direction. As coupling yield for each nucleotide is usually only 98.5%, a considerable number of fragments in unpurified oligonucleotides are shorter than the required oligonucleotide. The oligonucleotide end involved in the ligation reaction should however be constant. For the experiment described in example 1 we therefore chose to use chemically synthesised oligo's of which the 3'-end is joined by ligation to the 5'-end of the long (enzymatic produced) fragment (Type A probe). The 5'-end of DNA fragments produced by restriction enzyme digestion is phosphorylated. The smaller chemically synthesised oligonucleotide (type B probe) does not have to be phosphorylated as only the 3'-end is used for the ligation reaction. In case of SNP analysis, the SNP site should be close to the end, preferably at the end or at the penultimate site of the chemically synthesised oligonucleotide in order to obtain the largest difference in ligation efficiency between matched and mismatched oligonucleotides.

In a preferred embodiment, the long enzymatic produced oligonucleotide is made by an amplification reaction such as PCR with the use of two primers, one of which contains a sequence tag at its 5' end. In another preferred embodiment of the invention the long oligonucleotide is produced by restriction enzyme digestion of a plasmid or phage clone. In a further preferred embodiment, the 5'-end of the long fragment (type A probe) to be ligated should be complementary to the target nucleic acid. Some restriction endonucleases, among which the commercially available Bsm 1 isolated from Bacillus stearothermophilus NUB36 cleave the DNA outside their DNA recognition site and provide a means to produce oligonucleotides that have a 5' end with perfect complementarity to the target nucleic acid. Other restriction endonucleases such as Sph I and Aat II produce oligonucleotides that have left only one nucleotide of the restriction enzyme recognition site at the 5' end of the fragment produced and can be used for the production of some type A probes.

The vector for the production of the long ligation fragment can be double stranded, or can be obtained in both single stranded and double stranded form such as M13 phages and phagemids. A double stranded form of the vector is required for efficient cloning of the fragments that are complementary to the target nucleic acid sequence. The absence of a complementary strand of the probe has advantages during the hybridisation procedure as the concentration of the hybridisation probe does not drop during the incubation due to reannealing of the complementary strands. Also the absence of a DNA strand complementary to the probe diminishes the possibility of the formation of primer-dimers and other side products during the amplification reaction.

Reproducible restriction endonuclease digestion of single stranded DNA is not possible. Digestion of single stranded DNA made partially double stranded by annealing of complementary oligonucleotides has however been described in the literature for linearization of circular single stranded phage DNA.

We observed that digestion of single stranded DNA with a short complementary oligonucleotide annealed to the restriction endonuclease site provides a perfect substrate for digestion by Bsm I, EcoRV and several other restriction endonucleases. Furthermore it proved possible to use these digests even without further purification in ligation reactions as described in the current invention. Care has to be observed however in the digestion of these artificial substrates as single stranded DNA is more prone to degradation than double stranded DNA.

An outline of a phage M13 derived clone used for MLPA reactions as in Examples 1–3 and 12–14 is shown in FIG. 4.

First the single Bsm I site of phage M13mp18 was removed. A new Bsm I site was introduced in the region occupied by the multiple cloning site of M13mp18. This Bsm I site and a Sph 1 site can be used to insert an oligonucleotide having sequence complementarity to the target nucleic acid. In a preferred embodiment this target sequence specific oligonucleotide has a length of at least 20 nucleotides and a melting temperature when annealed to its complementary sequence of at least 60° C. At the 3' end of this fragment a stuffer fragment is inserted such as a fragment of phage Lambda or phage T7 DNA. We discovered that the use of a stuffer sequence in at least one of the two oligonucleotides has many advantages. In a preferred embodiment, the only purpose of this fragment is to obtain a specific length between the Bsm I site and sequence tag X, which is located at the 3' end of this stuffer sequence. In a second preferred embodiment this stuffer sequence is selected for not containing any polymerase pause sites and having an equal amplification efficiency in amplification reactions as compared to the stuffer sequences of other probes. In a third preferred embodiment, this stuffer sequence of one or more probes may contain a specific sequence tag used to identify ligation products for instance using real-time quantitative PCR with the use of molecular beacons as marketed by Stratagene Corp., fluorogenic probes such as Taqman probes that are based on the 5' nuclease activity of some heat stable polymerases and are marketed by the PE Biosystems Corporation or fluorescent probes using fluorescence resonance energy transfer (FRET) as used in the lightcyclers of the Roche company. In a fourth preferred embodiment the stuffer fragment of one or more probes may have a specific melting temperature that may be used to identify amplification products for instance with the use of the light cycler apparatus of the Roche company.

At the 3' end of sequence tag X an EcoR5 site is located that is used-to remove the type A probe from the bulk of the M13mp18 DNA. Each probe used preferably has a different stuffer sequence between the target specific sequence and the sequence tag in order to prevent amplification artefacts due to heteroduplex formation during later parts of the amplification reaction. The length between the sequence tag X which is used during the amplification reaction and the Bsm I site combined with the length between sequence tag Y and the 3' end of the other probe determine the length of the amplification product which may be used to identify the amplified probe.

In a preferred embodiment, the short probes contain a sequence tag Y at their 5' end and a target specific sequence at the 3' end. In a further preferred embodiment this target sequence specific oligonucleotide has a length between 18 and 45 nucleotides and a melting temperature when annealed to its complementary sequence of at least 55° C., preferably at least 60° C. By using for a specific target sequence more than one short probe differing in one, or a few nucleotides close to the 3' end involved in the ligation reaction as well as in the length between sequence tag Y and the 3' end, closely related target nucleic acid sequences such as an SNP at the site of the ligation-reaction can be distinguished as shown in example 1.

The formation of specific abundant amplification products may be limited by providing for a specific target nucleic acid a (competitor) oligonucleotide capable of annealing to the same target nucleic acid sequence as the probe used but lacking the sequence tag used for the amplification reaction. This may be useful when studying target nucleic acids sequences that differ greatly in copy number for instance when using a probe specific for the cDNA copy of an abundant mRNA sequence as well as probes specific for the cDNA copies of rare mRNA sequences.

The target nucleic acid is rendered single stranded and exposed to the various added oligonucleotides in order to enable duplex formation. As certain regions of chromosomal DNA may have a very high G/C content, it may be difficult to denature these stretches of DNA in the solutions of high ionic strength that are preferred for the annealing of the probes. Addition of salt after the denaturation step is therefore preferred.

Annealing of the oligonucleotides to the template is faster in buffers of high ionic strength. The salt concentration of the buffer has to be reduced however to less than approximately 150 mM after the annealing reaction for optimal ligase activity. Inclusion of certain chemicals such as polyethyleenglycol polymers or proteins such as BSA may increase both the ligation activity as well as the oligonucleotide hybridisation speed and do not interfere below certain limits with the ligation and amplification reactions. An increase in hybridisation speed will also be obtained by concentration of all nucleic presents in a small region of the reactionvolume by means of applying an electric potential across the reaction volume. As shown in the examples it is possible to obtain a so called "one-tube reaction" by careful selection of the hybridisation, ligation and amplification reaction conditions.

The duration of the probe annealing is very important. Some probes will hybridise faster than others. This is due to a difference in length of the hybridising sequence; the presence or absence of regions with a high % G/C (GC-clamps); secondary structure of the probes and/or the target sequence etc. In case the purpose of the experiment is the relative quantification of nucleic acid sequences, care has to be taken that either hybridisation of each probe is complete, or that hybridisation of none of the probes is complete. In case the purpose of the experiment is the relative quantification of genomic DNA sequences, it will be advantageous to prolong the duration of the annealing reaction in order to make sure that all target sequences have probes annealed to them. Most target sequences will be present in diploid form in most tissues and will generate signals of almost equal strength provided that hybridisation of all probes is complete and that ligation- and amplification-efficiency of all probes are similar. Annealing of the probes to the target nucleic acid is concentration dependent and is preferably performed in a small volume in the order of 10 ul. and at temperatures of 50–65° C. in order to prevent annealing of probes to a specific sites. In order to prevent evaporation the use of a thermocycler with heated lid is preferred.

In a preferred embodiment, the two target specific sequences of the two probes are complementary to adjacent but not overlapping sites of the target nucleic acid.

In case probes are used that anneal close to each other but not to adjacent sites on the same nucleic acid strand, the probe with the target specific sequence at its 3' end can be elongated by a polymerase in the presence of a suitable buffer and dNTP's in order to make ligation of the two probes possible. As a more suitable alternative the gap between the probes can be filled by complementary oligonucleotides that can be ligated to the probes. In this embodiment more than one ligation site is present and more than site will influence the amount of amplification product obtained. This will be useful for detection of mutations or SNP's that are close to each other.

When both oligonucleotides to be ligated are annealed to the target nucleic acid, a covalent phosphate link between the two fragments can be formed enzymatically by a ligase.

DNA ligases are enzymes capable of forming a covalent phosphate link between two oligonucleotides bound at adjacent sites on a complementary strand. These enzymes use either NAD or ATP as a cofactor to seal nicks in ds DNA. Alternatively chemical autoligation of modified DNA-ends can be used to ligate two oligonucleotides bound at adjacent sites on a complementary strand (Xu, Y. & Kool, E. T. (1999), Nucleic Acid Res. 27, 875–881).

Both chemical as well as enzymatic ligation is much more efficient on perfectly matched oligonucleotide-target nucleic acid complexes compared to complexes in which one or both of the oligonucleotides form a mismatch with the target nucleic acid at, or close to the ligation site (Wu, D. Y. & Wallace, R. B. (1989) Gene, 76, 245–254; Xu, Y. & Kool, E. T. (1999), Nucleic Acid Res. 27, 875–881). During recent years many attempts have been made to increase the specificity of the ligation reaction as measured by the relative ligation efficiencies of perfectly matched and mismatched oligonucleotides. The use of longer oligonucleotides, higher reaction temperatures and ligases active at these elevated temperatures has considerably increased specificity. In a preferred embodiment of the current invention a ligase is used that remains active at 50–65° C. for prolonged times, but which can be easily inactivated at the higher temperatures used during a PCR reaction. The only ligases commercially available at the moment are enzymes that function only at temperatures below 50° C. such as the DNA ligase encoded by *E.coli* and by phage T4, and thermostable enzymes that have a half-life of more than 30 minutes at temperatures of 95° C. such as the DNA ligase encoded by Thermus aquaticus.

For our experiments we purified a NAD requiring DNA ligase from a gram positive bacterium present in our laboratory (Strain MRCH 065). This ligase is designated "Ligase 65" and is commercially available from MRC Holland. Ligase-65 is active at 60–65° C. In contrast to Tth- and Taq DNA ligase however, the activity of ligase-65 is destroyed more than 90% by incubation in the optimum reaction buffer for 10 minutes at 95° C.

In another embodiment, a thermostable ligase such as the ligase from Thermus aquaticus may be used and the annealing and ligation reactions can be repeated several times by alternate cycles of heat denaturation and probe annealing. This particular embodiment is more time consuming unless higher concentrations of probes are used to increase the speed of the annealing reaction. Higher concentrations of probes increases however the chance on primer-dimer formation during the amplification reaction. The amount of probes used in the preferred embodiment of the MLPA reaction (approximately 1–10 femtoMol in a 10 ul ligase reaction) is more than one magnitude lower than the amounts routinely used in the ligase chain reaction. This is important when using a large number of probes in one assay. One of the two PCR primers is complementary to the end of one of the probe oligonucleotides. This means that this probe oligonucleotide even when not ligated to the other probe oligonucleotide can be amplified by PCR but only by linear amplification. For a probe mix containing 4 femtomoles each of 40 MLPA probes, 160 femtomoles of this PCR primer is consumed resulting in the consumption of 4800 femtomoles or 48% of the available 10 picoMoles PCR primer that is used in a typical PCR reaction. The use of much more than 10 times higher amounts of probe will substantially reduce the number of effective PCR cycles and thus the sensitivity of the assay as well as reduce the number of probes that can be used in one assay. The use of probe amounts in the previous art up to 1500 femtomoles/reaction which is 375 times the amounts used in the current invention also results in strongly increased chances on the formation of primer-dimers, other side-products and false positive signals. In a preferred embodiment of the current invention the majority of probes are present in amounts of less than 40 femtomoles/reaction. In a second preferred embodiment most of the probes containing a sequence tag complementary to one of the two PCR primers are present-in amounts less than 15 femtomoles/reaction. In a third preferred embodiment the ratio between the amounts present of each probe having a sequence tag complementary to one of the two PCR primers, and the amount used of that PCR primer during the amplification reaction is less than 1:500 for the majority of these probes. This ratio is important for both enzymatic as well as synthetically produced probes when multiplex reactions with more than 5 probe pairs are performed.

Following the ligation reaction, the ligation products consisting of a type A probe covalently joined to a type B probe can be amplified with the use of two oligonucleotide primers, dNTP's and a polymerase, one primer being complementary to one of the sequence tags and the other primer corresponding in sequence to the second sequence tag. The preferred method for amplification is PCR. As shown by Vos et al (Nucleic acid Research 23, 4407–4414; 1995), conditions can be found in which DNA fragments between 70 and 700 nucleotides containing the same sequence tags are amplified with almost equal efficiency as they are present in the same amplification reaction and use the same primers. The preferred conditions include a sufficiently long elongation time and the presence of a higher concentration of Taq polymerase than in ordinary PCR reactions. Other amplification methods than PCR such as NASBA or 3SR (Guatelli et al., Proc. Natl. Acad. Sci. USA 87:1874–1878, 1990) can also be used in combination with the current invention. The sequence tags used for the PCR reactions can easily be replaced by RNA polymerase binding sites.

The activity of the polymerase used in the polymerase chain reaction can temporarily be inhibited e.g. by chemical modification of the enzyme or by addition of antibodies to the enzyme. As a result the polymerase activity will be apparent only after heating the sample permitting the development of a test in which the ligase and polymerase can be added simultaneously and wherein the ligase is active at moderate temperatures and is inactivated at high temperatures whereas the polymerase is activated only after the heating step. A so-called hotstart for the PCR reaction is advantageous since in case one of the two PCR primers (complementary to the primer sequence of the long enzymatic produced oligonucleotide) anneals to one of the short probes containing the other PCR primer sequence, a primer dimer is formed upon elongation of the primer. One of the disadvantages of the use of (denatured) double stranded long probes is the increased chance of primer dimer formation as also the second amplification primer can form primer dimers upon annealing to and elongation on the unused strand of the long probe. As mentioned already also the probe oligonucleotides can easily produce primer dimers and other side products during the amplification reaction, particularly if present at high concentration.

The formation of primer dimers can be further inhibited by using a two-step nested primer amplification reaction. The sequence tag on the long probes used in the examples is 36 nucleotides long which is sufficient for the design of two different primers having limited sequence similarity for use in a nested primer amplification reaction.

When only extremely low amounts of target nucleic acid are available it may be preferred to use more probe mixes simultaneously in one assay. All ligated probes can be amplified simultaneous in a first PCR reaction using PCR tags common to all probes. Subsequently this first PCR reaction can be divided in several aliquots and specific subsets of probes can be further amplified in a second amplification reaction using PCR tags common to probes of a specific subset only.

In general the amplification conditions for PCR can be equal to the conditions used for AFLP reactions (Vos et al, Nucleic acid Research 23, 4407–4414; 1995). AFLP and MLPA reactions usually stop as a cause of all primers being consumed. Additional amplification cycles have therefore no or only limited influence on the results obtained and results obtained do not depend strongly on the amount of target nucleic acid in the sample.

There is no need to ensure that each amplification cycle has a 100% efficiency as long as the chance of each fragment being elongated is almost equal. As only one primer pair is used in AFLP and in MLPA reactions, this appears to be the case. Care has to be taken however that all primers being elongated during a PCR cycle are also completed. Long fragments require a longer elongation time and higher polymerase concentrations for complete elongation as compared to short fragments. Longer fragments also have a higher chance of remaining unfinished due to a non-complementary nucleotide being incorporated. Addition to the PCR reaction of a small amount of a proof-reading polymerase such as the Pfu polymerase purified from Pyrococcus furiosis may prevent this.

Many PCR protocols as for example "touch-down" PCR deliberately sacrifice the efficiency of the first amplification cycles in order to gain specificity and reduce background. In traditional multiplex PCR using multiple primer pairs this is difficult as the various primer pairs will have different annealing rates especially at temperatures close to, or slightly above the Tm of the primers. As only one primer pair is used in AFLP and MLPA reactions, protocols such as "touchdown" PCR can be used.

Several agents known to increase the speed of the annealing reaction have no or only a limited influence on a PCR reaction. Polyethyleenglycol e.g. has only a limited influence on the PCR reaction at concentrations up to 1%, implicating that concentrations up to at least 5% may be present during the annealing reaction as performed in examples 1–3 and 12–14.

In some of the examples provided, only 10 ul of the 50 ul ligation reactions are used for the amplification reaction. As the buffer composition during the ligation reaction is very similar to a standard PCR buffer, it proved also possible to use the complete volume of the ligation reaction and start the amplification reaction by the addition of primers, dNTP's, a small amount of a non-ionic detergent such as 0.01% triton X-100 and a heat stable polymerase such as Taq polymerase. The presence of other compounds such as betaine, are known to improve some multiplex PCR amplification reactions and do not severely inhibit the ligation reaction.

For most experiments it is advantageous to use PCR conditions that prevent a bias in the amplification of some amplicons. Important in this respect is that the concentrations of the amplicons during the later stages of the amplification reaction do not reach very high concentrations. This can be accomplished by using only low amounts of one of the PCR primers. A bias in the amplification of some amplicons will be due to faster renaturation kinetics of some amplicons after each denaturation cycle and displacement of PCR primers by the complementary strand of the amplicon.

Important in this respect is also the nature of the first nucleotide following the PCR primer, G or C being the preferred first nucleotides. This displacement will be reduced when using PCR primers containing one or more LNA residues at their 3' end. LNA (Locked Nucleic Acids) residues have an improved thermostability of duplexes towards complementary DNA strands (Wahlestedt, C. Et al. Proc.Natl.Acad.Sci.USA 97, 5633–38).

For some experiments it is advantageous to use PCR conditions that promote the amplification of rare templates as compared to the amplification of more abundant templates in order to obtain bands of almost equal intensity for the different nucleic acid target sequences tested. These PCR conditions may include: (1) The use of higher salt concentrations which promote the annealing of complementary strands and reduce the polymerase activity; (2) High concentrations of primers (3) Reduced annealing/extension temperatures during the last PCR-cycles; (4) Additives to the PCR buffer such as betaine and DMSO.

In a preferred embodiment detection of the amplification products is accomplished after separation of the fragments by gel-electrophoresis. In some cases it may be desirable to digest the amplification products with one or more restriction endonucleases before gel-electrophoresis in order to differentiate between different possible amplification products.

In several of our examples we have obtained labelled amplification products by using a fluorescent primer and have separated the amplification products using an acrylamide based gel electrophoresis system with a one colour fluorescent detection system. Some automatic sequenators rely on the use of four differently fluorescently labelled primers each having a unique colour signature, enabling the analysis of more than one sample in a single lane and the use of internal size standards. It is however also possible to use PCR primers which are radioactively labelled, or that are labelled with other compounds that can be detected with the use of the appropriate calorimetric or chemiluminescent substrates. In a clinical setting and for general use in many clinical testing laboratories, it is preferable that methods not requiring the use of radiolabeled nucleotides be used.

In another preferred embodiment, mass spectrometry is used to detect and identify the amplification products.

In a third preferred embodiment, the melting temperature of the amplification products which can be influenced by the choice of the stuffer fragment is used to identify the amplification-products.

In a fourth preferred embodiment, the presence of a sequence tag on the amplification products is used to detect the amplification products and to analyse the results of the experiment. A sequence tag can easily be incorporated in the stuffer region of the probes and can be used to discriminate e.g. probes specific for wild-type sequences and probes specific for mutant sequences. Separation of the fragments by gel electrophoresis is not necessary as the use of fluorogenic probes and the use of the 5' nuclease activity of some polymerases that can be used in the amplification reaction permits real time quantitative detection of the formation of at least two different sequence tags for instance one tag specific for a control wild-type specific probe and the other tag being specific for one or more different mutant sequences.

The necessary fluorogenic probes are described for instance by Lee et al (Nucleic Acid Research 21: 3761–3766; 1993). Detection of fluorescence during the thermal cycling process can be performed for instance with the use of the ABI Prism 7700 sequence detection System of the PE Biosystems Corp. Other real time detection methods that do not rely on the destruction of sequence tag bound oligonucleotides by the 5' nuclease activity of a polymerase but on the increased fluorescence of some fluorogenic probes (molecular beacons) upon binding to the sequence tag can also be used in the present invention as well as detection probes consisting of two entities, each being complementary to sequences present on one or more amplification-products and each containing a fluorescent moiety wherein fluorescent resonance energy transfer (FRET) occurs upon binding of both entities to the target amplification product.

Application of a MLPA Assay for SNP Characterisation and Mutation Detection:

In one embodiment the current invention employs a mixture of probes in one reaction, each probe being specific for one nucleic acid sequence. Each type B probe contains an oligonucleotide that has a region complementary to the target DNA sequence e.g. the sequence essentially flanking the SNP, as well as a common sequence-tag that can be used for the amplification reaction. For each SNP two or more type B oligonucleotides are used that differ in the nucleotide at the position of the SNP and in the number of nucleotides between the sequence tag used for the amplification reaction and the SNP site. Alternatively it is possible to use only one type B probe specific for the rare SNP allele. In addition another single stranded DNA fragment (type A probe) is provided that has at one end a nucleotide sequence complementary to the nucleotide sequence flanking the SNP, as well as a sequence tag common to all type A probes which is used in the amplification reaction.

When more than one SNP is analysed, the length of the type A and type B probes can be chosen such that each possible ligation product results in an amplification product that has a unique size.

After incubation of the probes and the single stranded template to be analysed under conditions promoting hybridisation of the probes to the target nucleic acid, the mixture is treated with a DNA ligase. In case more than one type B probe is used, one or more of the type B probes will have a mismatch at the position of the SNP, which is at the end, or close to the end of the type B probe. These probes will be ligated at a lower efficiency to the type A probe than the type B probe(s) that has no mismatch at the SNP position. Upon successful ligation of a type A and a type B probe, a DNA fragment is produced that can be amplified e.g. by PCR using a primer specific for the DNA sequence common to all type A probes and a primer specific for the sequence common to all type B probes.

NAD requiring ligases are very sensitive to the presence of mismatches between the complementary strands that are closer than approximately 9 bp from the site of ligation. The greatest difference in ligation efficiency between perfectly complementary strands and complexes having a mismatch is however obtained when the mismatch is exactly at the site of ligation.

Type B-probes have a preferred length of 30–60 nucleotides and differ for instance 2–4 nucleotides in length dependent on the nucleotide at the SNP position. Type A probes preferably have a length of 45–600 nucleotides. For each SNP a different set of two or more type B probes and one type A probe is added. Upon multiplex amplification and detection e.g. on sequencing type polyacrylamide gels, by capillary electrophoresis or by mass spectroscopy, a banding pattern is obtained in which the length and the relative intensity of the bands obtained depend on the length of the type A and type B probes and the efficiency of ligation of the different type B probes to the type A probes.

It has been well established that two oligonucleotides annealed to adjacent sequences on a target nucleic acid are efficiently ligated provided that there is no mismatch between the oligonucleotides and the target nucleic acid close to the ligation site. Thus the type B probe having the best complementarity to the target nucleic acid will be ligated more efficiently to the type A probe than the other type B probes.

When both sequence variants are present i.e. the sample is heterozygote for the SNP, two closely related amplicons are produced, one originating from ligation of the first type B probe with the type A probe, while the other originates from the ligation product of the second type B probe and the type A probe. An example is shown in Example 1 and FIG. 16. It was noted that one of the two amplicons, most often the smallest, was often produced in higher amounts than the other amplicon. We discovered that the incorporation of small non-identical stuffer sequences between the hybridising sequence and the PCR tag in both type B probes diminished this bias in amplification efficiency. As the type B probes can be made synthetically and should therefore preferably be small, a stuffer region was present in only one of the two type B primers used in example 1 and in FIG. 1. The only function of this 3–4 nucleotide stuffer region was to obtain a size difference between the two closely related amplicons. The incorporation of a (different) stuffer region in both type B probes was therefore not the first choice. As the two amplicons in this particular embodiment have an almost identical sequence, not only homoduplexes but also heteroduplexes will be formed during the final part of the amplification reaction. During later stages of the PCR reaction a competition takes place between primer-binding/elongation and duplex formation of the amplicons. Quite often a heteroduplex will be formed between strands at which a PCR primer is already annealed as it takes some time for the polymerase enzyme to find the annealed primer and start its elongation. During this time the PCR primer might be displaced by the long complementary amplicon. This will not happen as easily when a short mismatch region is present immediately adjacent to the PCR primer binding site. Both the majority of the hybridising region as well as the PCR tag region are complementary in the heteroduplex. A small non identical stuffer region will accomplish that the target hybridising region and the PCR tag region behave as independent regions in the heteroduplex and will accomplish that the PCR primer will not as easily be displaced. This part of the invention will be of use in both assays using a enzymatic type A probe as well as assays in which a synthetic type A probe is used.

Different oligonucleotide sets for different SNP's can be tested simultaneously provided that each possible amplification-product has a unique length. Using sequencing type electrophoresis systems and multicolour fluorescently labelled PCR primers, more than 100 SNP's may be analysed in one lane.

RNA or cDNA can also be used for the alignment of oligonucleotides designed for detection of the SNP specific nucleotide. For multiplex SNP detection however it is more convenient to use denatured DNA as a target as the number of targets for each SNP is than almost identical. The amount of a specific mRNA may be higher but is more variable. If the purpose of the experiment is however the identification of a strain or species, ribosomal RNA or the cDNA thereof or the multiple DNA copies coding for it may be a useful target.

Application of a MLPA Assay for the Detection of Mutations or Other Specific Nucleic Acid Sequences In case the purpose of the experiment is only to detect the presence or absence of a specific nucleic acid sequence, only one A and one B type probe specific for that particular nucleic acid sequence and annealing to adjacent sites on that target nucleic acid need to be provided. Again by changing the length of one or both of the probe oligonucleotides, all ligated oligonucleotides can be detected and identified by virtue of the unique length of the amplification products of the ligation products. Samples can therefore be tested simultaneously for the presence of a large number of nucleic acid sequences in one assay.

In case the nucleic acid sequence to be detected is relatively rare, it is often to be preferred to detect only this sequence and not for instance the wild type allele as would be done in SNP analysis. For any mutation to be detected a probe is provided that has the sequence unique for that mutation at or close to one of the ends of the probes that are ligated. No probe specific for wild-type sequences needs to be provided. Only in case a mutation recognised by one of the probes is present in the target nucleic acid, amplicons of a specific size or having a specific sequence will be generated. As the number of bands obtained is small, the amplification products can be analysed by rapid and cheap methods such as agarose gel electrophoresis. Samples containing a mutation can be analysed further using methods with higher separating power such as acrylamide type sequencing gels or by sequence analysis of the amplification product. In many cases it may be preferred to detect only one or a few wild-type sequences as a control for the presence of sufficient target nucleic acids and the correct performing of the MLPA assay and a large number of mutant target nucleic acid sequences. In a further preferred embodiment the signal obtained from the wild-type specific probes is reduced by the addition of competing oligonucleotides binding to the same wild-type nucleic acid sequences. As a result the relative amount of signal obtained from the mutant specific probes is increased. In general the wild-type sequences are present in both chromosomal copies while the mutant sequences are present on one chromosome only. An outline of this MLPA variant is shown in FIG. 5. This particular embodiment is described in further detail in Example 6.

In most examples of the present invention probes containing non hybridising stuffer regions are used. The use of a small hybridising region permits the screening of mutations that are close to each other. In case different probe pairs have part of their target sequence in common, they will compete with one another for binding to this common target sequence. In a preferred embodiment, the combined hybridising region of a probe pair has a length of 40–120 nucleotides. In a further preferred embodiment this length is 45–80 nucleotides.

In case no, or only limited amounts of sample material containing the mutation of interest are available, it is possible to use a synthetic copy of the sequence of interest in order to test the performance of the probe pair. Great care has to be observed to prevent contamination of pipettes and other laboratory equipment with these oligonucleotides as contamination of samples with only zeptomoles of this oligonucleotide will produce positive MLPA test results.

In case tumour samples are analysed it must be realised that biopsy material from a tumour can have a significant complement of normal cells. MLPA assays as described in FIG. 5 and example 6 can be used to detect mutated nucleic acid sequences in a high background of normal DNA provided that the sequence of the mutation is known.

MLPA assays as described in FIG. 5 and example 6 have an advantage over traditional nucleic acid amplification based detection methods as traditional PCR, 3SR and Nasba in that internal controls are provided for each sample confirming that a negative test result was not due to any error made during preparation of the sample or during sample analysis.

In another preferred embodiment wild-type and mutant specific probes may be distinguished by the presence or absence of a specific sequence tag in the stuffer region of the probe oligonucleotides. This sequence tag can be used for the binding of complementary labelled oligonucleotides that can be used in real time amplification methods. Useful oligonucleotides are for example the so-called "Molecular Beacons" marketed by Stratagene Corporation and Taqman probes marketed by PE Biosystems Corp. both containing a reporter fluorescent dye as well as a quencher dye and dual fluorescently labelled hybridisation probes capable of fluorescence energy transfer as marketed by Roche company for use in the lightcycler. Detection of amplification products containing a specific sequence tag is accomplished by detection of increased fluorescence due to binding of the molecular beacon to the sequence tag or by degradation of target bound taqman probes by the 5' nuclease activity of some polymerases such as Taq polymerase. The advantage of the use of these real time fluorescence detection methods is that labour intensive gel-electrophoresis for the separation of wild-type (control) and mutant specific amplification fragments is avoided and that tubes do not have to be opened after the amplification reaction, diminishing the chance on contamination of other samples that have not yet been amplified. A disadvantage is that only a very limited number of different fluorescence signals can be discriminated as compared to the simultaneous discrimination of more than 50 different amplification products by gelelectrophoresis or mass spectrometry.

Finally it is also possible to use only probes specific for certain sequences and detect amplification products by the appearance of long double stranded DNA for instance by measuring the increased fluorescence of some DNA intercalating dyes such as SYBR Green. The long amplification products formed in the process of the current invention can be easily distinguished from primer dimers for instance by the measurement of the melting temperature after or during the amplification procedure.

MLPA assays as outlined in FIG. 5 can easily be combined with the MLPA variant described in example 3 and outlined in FIG. 12. Using one long oligonucleotide containing a sequence tag and a mixture of target specific short chemically derived oligonucleotides that can be ligated to each other and to the long oligonucleotide, a multiplex test for the detection of specific nucleic acid sequences can be rapidly developed. In a preferred embodiment such test is used for the detection of relatively rare mutations or the presence of relatively rare nucleic acids such as those from specific pathogens.

Application of a MLPA Assay for the Relative Quantification of DNA Sequences

DNA rearrangements as well as amplification or deletion of large segments of chromosomal regions due to genetic instability are frequently linked to neoplasia. Deletions are usually detected by loss of heterozygosity (LOH) of microsatellite sequences which is a method difficult to perform on a large number of genes. Gene amplification or loss of gene copies can be detected by cytogenetic analysis for instance by fluorescent in situ hybridisation ("FISH") or by comparative genomic hybridisation methods which require specialised expertise, are time consuming and require large probes. These methods cannot be used to study microdeletions or -amplifications.

The current invention can be used to detect amplification of chromosomal regions or loss of heterozygosity at 10–100 sites simultaneously. In addition the relative number of copies of particular genes can be determined without knowledge of micro-satellites or SNP's in these genes. This provides the possibility to determine clonality of tumors in an easy way and provides the possibility to detect trisomy of human chromosomes in foetal samples. Other non-limiting applications are the discrimination of benign and malignant tumors using extremely small amounts of DNA available from microbiopts as malignant tumors generally have more and other chromosomal aberrations. Important in this respect is the reproducibility of the test results. As shown in example 13 it is possible to make probes and to use reaction conditions wherein the standard deviation of the relative amounts of the various amplicons produced in one assay was below 10% for a great majority of the probes used. Detection of both a 50% loss in number of target sequences (One vs. two copies) as well as a 50% increase in copy number (Three vs. two copies) were easily detected. Thus the MLPA process of the current invention constitutes a significant advance over prior processes.

Application of a MLPA Assay for the Relative Quantification of mRNA Sequences

In case the purpose of the experiment is the relative quantification of a number of different nucleic acids, such as different mRNA's, only one type A and one type B probe specific for each particular nucleic acid sequence and annealing to adjacent sites on that target nucleic acid need to be provided. RNA can be a ligation template when T4 DNA-ligase is used as the ligation enzyme, preferably in the presence of Mn ions in the buffer ((Hsuih et al (1996) J. Clin.Microbiology 34, 501–507). RNA is however easily degraded by RNAses and is a poor template for ligation reactions in which thermophilic NAD+ requiring bacterial ligases are used. Our attempts for the detection of the mRNA coding for the human ribosomal protein S24 using probes that could hybridise to directly adjacent sites of the mRNA were not successful (EXAMPLE 1). As only a very small template (40–70 nucleotides) is needed for the ligation reaction of the two probes, RNA can be efficiently reverse transcribed in the region required with the use of a specific primer located very close to the hybridisation sequences of the probes (FIG. 8). The cDNA obtained is an efficient substrate for the alignment of the two hemiprobes used. Alternatively the RNA can be reverse transcribed with the use of oligo-dT (FIG. 7) or a mixture of small oligonucleotides of random sequence as a primer. Finally a reverse transcription primer sequence can be part of one of the two probes (FIG. 11). After reverse transcription, the RNA can be removed from the cDNA by RnaseH treatment or by heating. In case a probe is used with a target (cDNA) specific sequence at its 5' end, a reverse transcription primer sequence at its 3'-end and the oligomer tag used for the amplification reaction in-between, a (large) hairpin will be formed easily when the target specific sequence anneals to its complementary cDNA sequence (FIG. 11). In this case only one hybridisation event needs to take place before the ligation reaction apart from the rapid hairpin formation.

A pair of probes to be ligated and designed for the detection of mRNA's can both bind within one exon in which case detection of the corresponding DNA sequence can be used to check the performance of the probes. It is however difficult to remove all contaminating DNA from a RNA preparation. Fragments smaller than 50 nucleotides are sufficient to give a positive signal in MLDA reactions but are difficult to degrade to much smaller fragments by DNAse treatment. Alternatively one of the two probes can be designed to detect a cDNA sequence which is predominantly located in another exon. In this case the pair of probes should be specific for the cDNA sequence and the signal obtained will not be sensitive to DNA contamination of the RNA sample. These probe pairs can be tested on a synthetic DNA copy of the RNA region to be detected.

The primers used for the reverse transcription reaction whether gene-specific or oligo-dT can also be used for the purification of the mRNA's or the cDNA produced from cell homogenates. Using reverse transcriptase primers with a gene specific sequence at the 3'-end and a hapten such as biotin, digoxigenin or a specific DNA sequence at the 5'-end (FIG. 9), mRNA's can be purified from cell homogenates with the use of immobilised hapten binding agents such as Streptavidin or a complementary DNA-sequence.

One preferred embodiment of the current invention makes use of reverse transcription primers containing a common sequence tag such as a GT repeat as used e.g. in the oligonucleotides SEQ ID NO:81–84. These sequence tags can be used before or after the reverse transcription-reaction to enrich the nucleic acid sequences of interest for instance by providing a complementary CA repeat containing a hapten such as biotin and immobilised streptavidine for the binding of the biotin moieties (FIG. 10). An advantage of this indirect purification system compared to biotinylated reverse transcription primers is the possibility to remove the enriched nucleic acids from the immobilised streptavidin-biotin complex by heating. Alternatively the CA oligonucleotides can be immobilised directly.

In general relative quantification of target sequences can be accomplished by using a high enough probe concentration and long enough annealing times in order to make sure that 100% of the target nucleic acids have probes annealed to the target sequences. This is a preferred embodiment of the MLPA method. Alternatively relative quantification can be accomplished by ensuring that at all target sequences annealing of one probe of each probe pair is incomplete.

The relative amount of specific amplification products can be reduced compared to the amount of other amplification products by providing a competitor oligonucleotide capable of annealing to a target sequence, preventing the annealing of one or both of the probes specific for that target sequence. By using mixtures of target specific probes and competing oligonucleotides binding to the same target sequence, the relative amount of amplification products from abundant mRNA's can be reduced.

It is to be preferred that the relative amounts of the cDNA targets to be detected accurately reflects the relative amounts of the RNA sequences present in the sample. In a preferred embodiment of the current invention a reverse transcriptase lacking strand displacement activity or reaction conditions in which strand displacement activity is reduced are used.

The application of the MLPA invention for the relative quantification of mRNA's is described in Example 2. An outline of the method is presented in FIGS. 6–11.

Long MLPA Amplicons without Target Specific Enzymatic Oligonucleotides.

If the current invention is applied to the analysis of one, or a small number of target nucleic acids, only relatively short (40–80 bp.) chemically produced oligonucleotides are required. For the simultaneous analysis of larger numbers of target nucleic acids however, long (60–600 nucleotides) oligonucleotides are required. With the current technology for the chemical synthesis of these molecules, oligonucleotides longer than approximately 80 nucleotides will preferably be enzymatic produced. Although technically no problem for one of ordinary skill in the art, this is time consuming as a new clone has to be produced for every SNP to be tested. We have therefore devised an alternative way to detect the specific nucleotide present at the site of an SNP that requires only SNP specific short (40–60 nucleotides) chemically produced oligonucleotides. This approach can also be used for the other applications of the current invention such as the detection and relative quantification of nucleic acid species, and is outlined in FIG. 12.

With this approach two ligation events are necessary to produce an amplification template consisting of two target specific oligonucleotides and a chemical or enzymatic produced oligonucleotide that has no relation at all to the target nucleic acid.

Two target nucleic acid specific oligonucleotides are aligned by the target nucleic acid and are a substrate for chemical or enzymatic ligation. Oligonucleotide 77 contains a sequence complementary to the target nucleic acid as well as a sequence tag to be used in the amplification reaction. For SNP detection, a mixture of two or more oligonucleotides 77 can be used which differ in length as well as in the nucleotide present at the SNP site.

Oligonucleotide 89 contains a sequence complementary to the target nucleic acid adjacent to the target specific sequence present in oligonucleotide 77, as well as a sequence complementary to oligonucleotide 90. Oligonucleotide 89 should be phosphorylated at its 5' end.

Oligonucleotide 90 contains a sequence complementary to oligonucleotide 89 as well as a sequence complementary to oligonucleotide M227. The function of oligonucleotide 90 is only to align oligonucleotides 89 and M227 in order to make chemical or enzymatic ligation of these oligonucleotides possible.

Oligonucleotide M227 contains a sequence complementary to oligonucleotide 90 as well as a sequence tag to be used in the amplification reaction. In case many target nucleic acids are analysed simultaneously, oligonucleotide M227 has to be relatively long for some target nucleic acids and may be preferably enzymatic produced. As this oligonucleotide has no target specific sequences, a standard set of oligonucleotides 90 and M227 can be used for many different target sequences.

For a true multiplex assay, different probes can be used which result after successful template directed ligation in amplification products having different characteristics such as length, mass, sequence, presence of a sequence tag or melting behaviour.

Alternative Embodiments for Performing a MLPA Assay:

In the experiment described in example 1 we have used chemically synthesised oligo's of which the 3' end is joined by ligase to the 5' end of the long (enzymatic produced )fragment. It is however also possible to use enzymatic produced long oligonucleotides of which the 3' end is joined to the 5' end of chemically produced short oligonucleotides. An outline of this MLPA variant is presented in FIG. 13.

The 3' end of the long fragment to be ligated should be complementary to the target nucleic acid. This fragment can be produced by restriction endonuclease digestion of a plasmid or phage clone. Some restriction endonucleases, among which the commercially available Sau 3A-I isolated from *Staphylococcus aureus* and Mbo I isolated from *Moraxella bovis* cleave the DNA outside their DNA recognition site and provide a means to produce fragments that have a 3' end with perfect complementarity to the target nucleic acid. Digestion of single stranded DNA obtained e.g. from phage M13 derivatives can be accomplished by rendering the phage nucleic acid partially double stranded at the restriction site by incubation with a complementary oligonucleotide. In case of digestion with Mbo I, the phage DNA has to be produced in a bacterial strain that does not contain a functional dam methylase, such as the *E. coli* JM110 strain available from Stratagene corp.

Many restriction endonucleases such as EcoR I and Hind III produce oligonucleotides that leave only one nucleotide of the restriction enzyme recognition site at the 3' end of the fragment produced and can be used for the production of some probes.

An advantage of this alternative approach is that the long oligonucleotide used can be made partially double stranded by incubation with a complementary oligonucleotide and a DNA polymerase. An oligonucleotide that is partially double stranded may be a more efficient hybridisation probe as a result of reduced internal secondary structure.

Disadvantages of this embodiment of the current invention however are the increased rise on formation of long primer dimers and the need to phosphorylate the short chemically synthesised probe oligonucleotides.

In the examples provided only probe sets are used of which the two probes to be ligated each have a part complementary to the target nucleic acid and where these target specific sequences hybridise with sequential and contiguous portions of the target nucleic acid. Alternatively, the two type A and type B probes may hybridise to non contiguous portions of the target nucleic acid. The gap between the two probes can be filled before the ligation reaction by one or more other target specific oligonucleotide as depicted in FIG. 21, or by a polymerase filling in the gap as depicted in FIG. 22. The polymerase should preferably have no or only a low level of strand displacement activity and 5' nuclease activity. In this last embodiment in which a polymerase is used to fill the gap between the two probes, there is no need to use long enzymatic produced probe oligonucleotides in order to obtain amplicons of sufficient length to perform multiplex analysis and to have a sufficient length to distinguish amplicons from primer dimers. In example 11 this embodiment is used to determine the site of chromosomal breakpoints.

In case the target DNA is immobilised before or after hybridisation to probes, the non-bound probes can be easily removed and will not be present during the amplification reaction. Although not necessary for most applications, this will reduce the background in case less than 1000 target molecules are present. Immobilisation can be accomplished for instance by cross-linking denatured target nucleic acid to filters as is often accomplished in dot-blot hybridizations. Alternatively the target DNA can be tagged by modification with biotin or digoxigenin residues by commercially available reagents. Before or after hybridisation tagged target nucleic acid can be separated from non tagged nucleic acid probes by well known procedures involving for instance magnetised micro-particles coated with streptavidin or coated with digoxigenin specific antibodies.

In the approach used in EXAMPLES 1–3, a chemically synthesised oligonucleotide (type B probe) is ligated at its 3'-end to the 5'-end of a long enzymatic produced type A probe. This way the probes can be made partially double-stranded next to the part that hybridises to the target nucleic acid by addition of a complementary oligonucleotide (FIG. 14). This "viagra"-oligonucleotide reduces the internal secondary structure of the probe and results in some cases in a faster hybridisation of the probe to its target sequence.

In a further embodiment "full length probes" may be used, consisting of a single oligonucleotide containing the two different sequence tags and giving rise to an amplification product of a specific size. Amplification reactions such as PCR are capable of detecting less than 100 molecules containing the two sequence tags. For many purposes not the absolute signal strength but the relative strengths of the signals obtained with different probes are interesting. Amplification reactions are often allowed to proceed for more than the minimum number of cycles needed in order to obtain signals of comparable intensities for different samples that may contain different amounts of target sequences and are stopped when one of the necessary ingredients, usually the amount of primers, becomes limiting.

The large number of amplification cycles increases the danger of minor contaminants being amplified to detectable levels when the amount of amplifiable ligation products is very low. A small amount of a "full length probe" e.g. 100 molecules, may therefore be provided to each sample. Detection of the amplification product of this full length probe is a warning that insufficient target specific ligation products were present at the start of the amplification reaction and that the results obtained should be regarded with caution.

Complete probes may also be used as spiked internal controls added after or even before purification of the nucleic acids from a sample in order to check the sample preparation and to estimate the absolute amount of the ligation products specific for the target sequences that are present before the amplification reaction.

As an alternative to ligation dependent formation of amplifiable molecules, "full length probes" containing not only the two oligomer tags needed for the amplification reaction at a certain distance from each other but also in-between or next to these oligomer tags a sequence capable of hybridising to a target sequence, can be used for multiplex detection of a large number of different target sequences. As in a MLPA assay, each probe can be distinguished by the unique length or mass of its amplification product. In order to obtain probes of sufficient length for multiplex analysis, probes are preferably derived from plasmid or phage DNA by digestion with restriction-endonucleases. Alternatively probes can be made by PCR using suitable primers as shown in FIG. 15. After hybridisation to the target sequences in a sample to be analysed, hybridised probes have to be separated from non-hybridised probes which can be accomplished e.g. by immobilising the sample nucleic acids (dot-blots), biotinylation of sample nucleic acids and binding of these sample nucleic acids+ hybridised full length probes to magnetic particles coated with streptavidin, and various other means.

In EXAMPLE 8 the results obtained with the use of two full length probes made by PCR with human DNA as the template are described.

The method of the present invention is advantageously practised for any set of target nucleic acids using a kit containing two or more probes that can be amplified with the same amplification primers wherein each probe contains a sequence complementary to one of the target nucleic acids. Such kits may also contain, in packaged combination, one or more of the following: a hybridisation/ligation buffer; a ligase enzyme; amplification primers specific for the sequence tags of the probes; and amplification reagents.

It will be evident to one of ordinary skill in the art that the invention described herein
can be modified and adapted without departing from the spirit and scope thereof.

The artisan will further acknowledge that the Examples recited herein are demonstrative only and are not meant to be limiting.

EXAMPLE 1

Detection of Mutations in the Human CFTR Gene.

For the preparation of long ligatable single stranded oligonucleotides of different length, we used phage M13mp18 which is available from New England Biolabs. The M13mp18 sequence is available from Genbank, accession number X02513. Double strand DNA of M13mp18 was digested with EcoR1 and Hind 3. The oligonucleotides of SEQ ID NO: 8 and SEQ ID NO:9 which form together a duplex having ends that can ligate to the EcoRI and Hind III sites of the digested M13mp18 was inserted. After ligation and transformation, plaques containing the inserted oligonucleotide were selected and
double stranded DNA was prepared of transformant MRCH001.

Double stranded DNA of this virus was digested with Nco I and Acc I. The oligonucleotides of SEQ ID NO:10 and SEQ ID NO:11 which form together a duplex having ends that can ligate to Nco I and Acc I sites of the digested MRCH001 was inserted. After ligation and transformation, plaques containing the inserted oligonucleotide were selected and double stranded DNA was prepared of transformant MRCH002. M13mp18 contains a Bsm 1 recognition site at position 1745–1750 which we removed from phage MRCH002 by changing the T-nucleotide at position 1748 into a C-nucleotide.

A primer (SEQ ID NO:12) was annealed to single stranded M13mp18 DNA. This primer was elongated by the Klenow fragment of DNA Polymerase I. After closing the resulting double stranded DNA with T4-DNA ligase, the DNA was heated 5 minutes to 95° C. in the presence of 10 pMol of an oligonucleotide (SEQ ID NO:13). This oligonucleotide was again elongated by Klenow fragment and the resulting d.s. DNA preparation was transformed in *E.coli* strain JM109 (Promega). Transformants were cultured together in one bottle for 5 hrs. Double stranded virus DNA was purified from the mixture of transformants and was digested with Bsm I. The digested DNA was again transformed in *E.coli* strain JM109, and virus plaques were tested for the presence of a Bsm 1 site. One transformant (MRCH106) not containing a Bsm I site was selected.

Double stranded DNA of this virus was digested with Nco I and EcoR I. The oligonucleotides of SEQ ID NO:14 and SEQ ID NO:15 which form together a duplex having ends that can ligate to Nco I and Hind 3 sites of the digested MRCH106 was inserted. After ligation and transformation, plaques containing the inserted oligonucleotide were selected and double stranded DNA was prepared of transformant MRCH107.

Double stranded DNA of MRCH107 was digested with PinA1 and Acc1 and the oligonucleotide SEQ ID NO:16+ SEQ ID NO:17 which together form a duplex having ends that can ligate to PinA1 and Acc 1 digested MRCH107 DNA was inserted. After ligation and transformation, plaques containing the inserted oligonucleotide were selected and double stranded DNA was prepared of transformant MRCH214.

The result of these steps is a M13mp18 derivative that lacks the Bsm I site at position 1745–1750 and has the sequence shown in SEQ ID NO:18 inserted in the EcoR 1 and
Hind 3 sites of M13mp18.

Four different PCR fragments derived from phage T7 DNA with the use of the following primer pairs were inserted in MRCH214: SEQ ID NO:19+20; 21+22; 23+24 or 25+26. These 4 PCR fragments were digested with Sph 1 and Xba 1 and ligated to Sph 1 and Xba 1 digested d.s.DNA of phage MRCH214. Primers SEQ ID NO:19, 21, 23 and 25 have an Sph 1 site close to their 5' end. Primers SEQ ID NO:20, 22, 24 and 26 have an Xba 1 site close to their 5' end. Phage T7 is available from the American Type Culture Collection. The T7 DNA sequence is available from Genbank as Acc. nr. V01146. In addition two oligonucleotides SEQ ID NO:27 and 28 which together form a duplex having ends that can ligate to Sph 1 and Xba 1 sticky ends was inserted in Sph 1 and Xba 1digested MRCH214 DNA. As a result five different phages were obtained that each have a DNA sequence of different length between the Bsm 1 site and the nucleotides 77–112 (sequence tag Y) of SEQ ID NO:18.

MRCH228 has a 34 bp T7 fragment inserted ; MRCH266 has a 79 bp T7 fragment inserted; MRCH273 has a 151 bp T7 fragment inserted; MRCH285 has a 310 bp T7 fragment inserted and MRCH113 contains a 349 bp T7 fragment.

The important features of these phages are depicted in FIG. 4 and can be summarised as follows:

A double stranded DNA fragment A having a CATG overhang at the 3' end of one oligonucleotide and a GG overhang on the other oligonucleotide, and having a sequence complementary to the sequence of interest can be inserted in the phages after digesting the double stranded phage DNA with Bsm 1 and Sph 1.

When single stranded DNA of the resulting clones is annealed with oligonucleotides of approx. 20 nucleotides that are complementary to the Bsm 1 site of these clones and the EcoR5 site at position 110–115 of SEQ. ID 18 and their flanking regions, the single stranded DNA can be digested with Bsm 1 and EcoRS and single stranded fragments are obtained that have the sequences of oligonucleotide A at their 5'-end and a specific length between the 5'-end and the sequence tag Y that is complementary to one of the primers used in the amplification reaction. The oligonucleotide used for digesting the EcoR5 site is shown in SEQ ID NO:29.

Each of the 5 phages made produces blue plaques on agar plates containing IPTG and X-gal. Upon insertion of an oligonucleotide X with a length that is not (2+a multiple of 3), white plaques are obtained.

In each of the five clones containing a T7 stuffer fragment an oligonucleotide was inserted into Bsm 1 and Sph 1 digested double stranded DNA. Each oligonucleotide is identical to the sequence at the 3'-side of a known mutation in the human CFTR gene (Genbank seq. nr. M55108–M55130).

The partially complementary oligonucleotides SEQ ID NO:30 and 31 were inserted in the Bsm 1 and Sph 1 sites of MRCH228; SEQ ID NO:32+33 in MRCH266; SEQ ID NO: 34+35 in MRCH273; SEQ ID NO:36+37 in MRCH285 and SEQ ID NO:38+39 in MRCH113, resulting respectively in phage clones MRCH231, 236, 243, 258 and 252. Single stranded phage DNA from these five clones was produced as described by Reddy, P. and McKenney K. (Biotechniques 20: 854–860; 1996). This single stranded DNA was annealed to two oligonucleotides: SeQ ID NO:29+40 for the MRCH231 DNA; SEQ ID NO:29+41 for MRCH236 DNA; SEQ ID NO:29+42 for MRCH243 DNA; SEQ ID NO:29+ 43 for MRCH258 DNA and SEQ ID NO:29+44 for MRCH252 DNA. Digestion was performed by incubation of 400 pMol of an M13 derivative single stranded DNA with 2.2 nMol of each of the two oligonucleotides and 8000 units EcoR5 in 10 mM Tris-HCl pH 7,6; 100 mM KCl; 10 mM MgC12 and 1 mM Dithiothreitol at 37° C. After incubation for 30 minutes, 4000 units Bsm 1 was added and the temperature raised to 50° C. After incubation for another 30 minutes the digested DNA was phenol extracted, ethanol precipitated and dissolved in TE.

For each mutation/SNP to be tested, two oligonucleotides were synthesised that have a common part used to amplify ligated oligonucleotides (Sequence tag X), and a part complementary to the CFTR sequence at the position of the mutation.

These oligonucleotides differ in length (4 bp) and in the nucleotide present at the site of the mutation. The site of the mutation is at the penultimate position or at the 3' end of the oligonucleotide.

Oligonucleotides SEQ ID NO:45 and 46 can anneal to a site adjacent to the insert of clone M231 on CFTR wild-type DNA or to DNA containing mutation E60X of the CFTR gene respectively. Oligonucleotides SEQ ID NO:47 and 48 can anneal to a site adjacent to the insert of clone M236 on CFTR wild-type DNA or to DNA containing mutation 621+1G>T of the CFTR gene respectively. Oligonucleotides SEQ ID NO:49 and 50 can anneal to a site adjacent to the insert of clone M243 on CFTR wild-type DNA or to DNA containing mutation deltaF508 of the CFTR gene respectively. Oligonucleotides SEQ ID NO:51 and 52 can anneal to a site adjacent to the insert of clone M258 on CFTR wild-type DNA or to DNA containing mutation 3659delC of the CFTR gene respectively. Oligonucleotides SEQ ID NO:53 and 54 can anneal to a site adjacent to the insert of clone M252 on CFTR wild-type DNA or to DNA containing mutation 2184delA of the CFTR gene respectively.

DNA of five different humans (50 ng in TE) was mixed in a 200 ul vial with 4 FemtoMol of each of the five digested phage DNA's and 10 femtoMoles of each of the ten oligonucleotides designated SEQ.ID. 45–54 in a final volume of 8.5 ul. DNA was denatured by heating for 5 minutes at 95° C. in a thermocycler with heated lid. To the mixture was added 1.5 ul salt mix: 1500 mM KCl; 300 mM Tris-HCl pH 8.5; 1 mM EDTA. Annealing of the probes to the target DNA was for 6 hrs. at 60° C. in a thermocycler with heated lid. To the mixture was added 40 ul dilution-buffer (2 mM MgCl2; 1 mM NAD+) and 10 units Ligase-65. The mixture was incubated for 15 minutes at 60° C. followed by 5 minutes at 95° C. 10 ul of the mixture was used as a template for a PCR reaction in a 50 ul volume containing 2 units Taq polymerase; 15 mM Tris-HCl pH 8.5; 50 mM KCl 1.5 mM MgCl2 and 0.01 Triton X-100.

After heating the mixture to 65° C., 10 pMol of FITC-labelled PCR primer Seq ID NO:55; 10 pMol unlabeled primer SEQ ID NO:56 and 2.5 nMol of each of the four dNTP's were added.

PCR was performed in 200 ul tubes in a Biometra Uno 2 thermal cycler using the following conditions 2.5 minute denaturation at 95 C.

10 cycles consisting of 30 second denaturation at 95 C; 30 second annealing at 70 C and 60 second elongation at 72 C.

40 cycles consisting of 30 second denaturation at 95 C; 30 second annealing at 60 C and 60 second elongation at 72 C.

Following the PCR reaction, 2 ul of this reaction was mixed with 2 ul of formamide containing 5 mg/ml blue dextran, heated for 5 minutes at 80 C. in order to denature the DNA and was analysed on a 6% acrylamide gel (acrylamide-bisacrylamide 29:1), containing 8 M urea in 100 mM Tris-borate pH 8.3; 2 mM EDTA. A Pharmacia ALF apparatus was used to run the gel and detect the fluorescent PCR products. The results obtained are shown in FIG. 16.

The probes used were designed to give rise upon successful ligation to amplification products of the following lengths when using the above mentioned amplification primers:

Probes MRCH231+SEQ ID NO:45: 148 bp.;Target: wild-type CFTR gene exon 3.
Probes MRCH231+SEQ ID NO:46: 152 bp.;Target: CFTR gene mutation E60X
Probes MRCH236+SEQ ID NO:47: 193 bp.;Target: wild-type CFTR gene intron 4.
Probes MRCH236+SEQ ID NO:48: 197 bp.;Target CFTR gene, mutation 621+1G>T.
Probes MRCH243+SEQ ID NO:49: 265 bp.;Target: wild-type CFTR gene exon 10.
Probes MRCH243+SEQ ID NO:50: 269 bp.;Target: CFTR gene mutation deltaF508.
Probes MRCH258+SEQ ID NO:51: 409 bp.;Target: wild-type CFTR gene exon 19.
Probes MRCH258+SEQ ID NO:52: 413 bp.;Target: CFTR gene mutation 3659delC.
Probes MRCH252+SEQ ID NO:53: 454 bp.;Target: wild-type CFTR gene exon 13.
Probes MRCH252+SEQ ID NO:54: 458 bp.;Target: CFTR gene mutation 2184delA.

Samples of human chromosomal DNA to be analysed were obtained from the Dept. of Antropogenetica, Free University of Amsterdam, and were known to contain the following mutations in the CFTR gene: Lane 1 of FIG. 16: No mutations; Lane 2: deltaF508 mutation on both chromosomes. Lane 3: deltaF508 mutation on one chromosome only. Lane 4: 3659delC mutation on one chromosome. Lane 5: R117H mutation on one chromosome.

The scale on FIG. 16 is not in bp. but in minutes after starting the gel-electrophoresis. As expected, 5 bands were obtained on wild-type DNA corresponding in size with the expected fragment sizes. In lane 2 the third band is running slightly slower through the gel corresponding to a size four bp. longer than the third band of lane 1 and corresponding in size to the fragment expected from the probe specific for the deltaF508 mutation. This same band as well as the wild-type band appear in lane 3, proving that both the wild-type probe as well as the probe specific for the deltaF508 mutation have given rise to an amplification product and thus proving that successful ligation of the probes has occurred. In Lane 4, an extra band has appeared corresponding in size to the probe specific for the 3659delC mutation. As expected no extra bands were observed in Lane 5 as no R117H specific probe was used.

As the resolving power of acrylamide sequence gels is good enough to use probes that give rise to amplification products differing only 4–6 bp in length, the number of probes used in one assay and to be distinguished by the specific length of the amplification products can be 50 or more.

EXAMPLE 2

The Relative Quantification of mRNA's:

In order to use the MLPA technique for the detection and relative quantification of mRNA's, probes were made that were complementary to two abundant human mRNA's coding for beta-actin (Genbank acc. nr. M10277) and the S24 ribosomal protein (Genbank acc. nr. U12202).

The probes were used in a MLPA assay as described in example 1 using 0.5 ug total human RNA derived from adrenal gland tissue (Clontech) as a ligation template.

Attempts were made to use either Ligase-65 at 50° C. or 60° C. or T4-DNA ligase with ATP as a cofactor at 37° C. or 45° C. and with either Mg or Mn as divalent ion during the ligation reaction. None of our attempts was very successful confirming that ligation of two DNA strands annealed to an RNA template is very inefficient when currently known ligases are used. Human chromosomal DNA was a good ligation template for both probes (not shown). Total human RNA gave no signal at all when ligase-65 was used and only a very faint signal when T4-ligase was used. Replacement of Mg by Mn improved the signal somewhat, but detection of the single copy gene sequence in human DNA was much more efficient than the detection of the multiple copy mRNA sequence in human total RNA.

As described below much more successful results were obtained by first preparing a cDNA copy of the mRNA's to be detected with the use of reverse transcriptase and a gene specific primer.

The Relative Quantification of cDNA's:

Four probes were made that were complementary to cDNA of human mRNA's coding for the S24 ribosomal protein (Genbank acc. nr. U12202), the prostate specific antigen (PSA; Genbank acc. nr. M27274), thymosin beta-10 (Genbank acc.nr. S54005) and MDA-6 (Gen-bank acc. nr. L25610).

In the same way as described in Example 1, four different PCR fragments derived from phage T7 DNA with the use of the following primer pairs were inserted in MRCH214: SEQ ID NO:57+58; 59+60; 61+62 or 63+64. As a result four different M13 derivatives were obtained: MRCH270 has a 115 bp T7 fragment inserted; MRCH275 has a 169 bp T7 fragment inserted; MRCH292 has a 208 bp T7 fragment inserted and MRCH202 contains a 304 bp T7 fragment.

For the S24 probe the partially complementary oligonucleotides SEQ ID NO:65+66 were inserted in vector MRCH202 digested with Bsm I and Sph 1. The resulting clone was designated MRCH213. For the PSA probe the partially complementary oligonucleotides SEQ ID NO:67 and 68 were inserted in vector MRCH270 digested with Bsm I and Sph 1. The resulting clone was designated MRCH215. For the Thymosin probe the partially complementary oligonucleotides SEQ ID NO:69+70 were inserted in vector MRCH292 digested with Bsm I and Sph 1. The resulting clone was designated MRCH216. For the MDA-6 probe the partially complementary oligonucleotides SEQ ID NO:71 and 72 were inserted in vector MRCH275 digested with Bsm I and Sph 1. The resulting clone was designated MRCH217. Single stranded DNA was prepared from each clone and was digested with Bsm I and EcoRV in the presence of oligonucleotides SEQ ID NO:29 and 73 (S24) or SEQ ID NO: 29 and 74 (PSA) or SEQ ID NO:29 and 75 (Thymosin) or SEQ ID NO:29 and 76 (MDA-6) as described in example 1. These probes were used in a MLPA assay as described in example 1 using oligonucleotide SEQ ID NO:77 (S24) or SEQ ID NO:78 (PSA) or SEQ ID NO:79 (Thymosin) or SEQ ID NO:80 (MDA-6) as the second probe.

A cDNA copy of the RNA to be analysed was made by incubation of 1 ug total RNA from liver, prostate, salivary gland or pancreas tissue (Clontech human total RNA panel V) with one specific primer for each mRNA to be detected. We used primer SEQ ID NO:81 (S24), SEQ ID NO: 82 (PSA), SEQ ID NO:83 (Thymosin) and SEQ ID NO:84 (MDA-6) in order to make a cDNA copy of the specific mRNA's to be analysed, but a mixture of random oligonucleotides or oligo-dT can also be used to prepare a cDNA copy of all mRNA's present in the sample.

A mixture of 1 ug RNA and 2.5 pMol of each cDNA primer in a volume of 3.5 ul was incubated for 5 minutes at 70° C. To this was added 2 ul dNTP mix (2.5 mM of each of the four dNTP's), 1.4 ul concentrated buffer (250 mM Tris-HCl pH 8,3; 75 mM KCl; 15 mM MgCl2; 40 mM Dithiothreitol) and 0.3 ul (60 units) MMLV-Reverse Transcriptase (Promega). Incubation was for 30 minutes at 37° C. in a thermocycler with heated lid followed by denaturation of the cDNA-RNA hybrids by heating 5 minutes at 98° C. Alternatively a RnaseH treatment can be used to remove the RNA part of the RNA-cDNA hybrid. RnaseH treatment has the advantage that no heat denaturation of the RNA-cDNA hybrid is necessary which is to be preferred in case the RNA preparation to be analysed is contaminated with DNA. Without heat denaturation this DNA will not be accessible for probe annealing and does not need to be removed.

To the mixture was added 1.4 ul 30×ligase buffer (1500 mM KCl; 300 mM Tris-HCl pH 8.5; 1 mM EDTA) and 10 femtoMol of each short probe (SEQ ID NO:77, 78, 79 and 80) and 1 ng digested M13 clones MRCH213 (S24) and MRCH216 (Thymosin) and 10 ng digested M13 clones MRCH215 (PSA) and MRCH217 (MDA6). Final volume was 10 ul. Following incubation at 60° C. for two hrs. in a thermocycler with heated lid in order to accomplish annealing of the probes to the cDNA ligation template, 40 ul dilution-buffer (2 mM MgCl2; 1 mM NAD+) and 10 units Ligase-65 were added. Ligation was for 15 minutes at 60° C. and was followed by a 5 minutes incubation at 98° C. in order to inactivate the ligase-65. 10 ul of the 50 ul mixture was used as a template for a PCR reaction containing 10 pMol of each PCR primer (Seq ID NO:55 and 85), 50 uM dNTP's and 2 units Taq polymerase as described in example 1.

Figure 18:
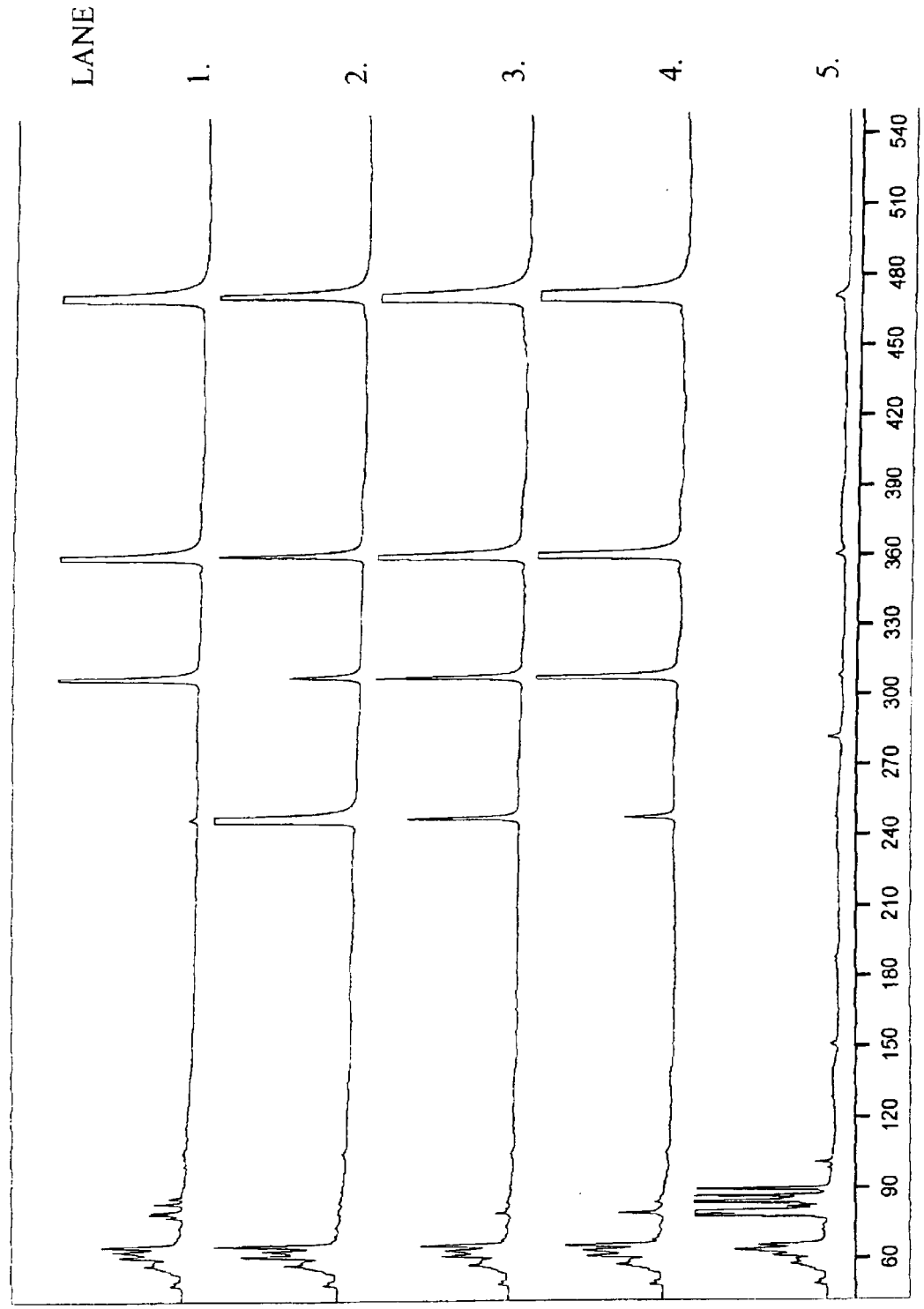
FIG. 18 shows the results obtained with MLPA for the analysis of total RNA samples from four different human tissues tested for the presence of four different mRNA's.

Results are shown in FIG. 18. The probes were designed to produce PCR products of 404 bp (S24), 310 bp (Thymosin), 265 bp (MDA6) and 211 bp (PSA) upon successful template directed ligation of the probes. As expected a strong band of 211 bp corresponding to the PSA probe was detected in samples of prostate RNA. The amounts detected in other tissues was far less. In each sample the amount of amplified thymosin-beta 10 probe was between 64 and 81% of the amount of Thymosin probe. The MDA6 probe was detected in smaller quantities: between 28% and 53% of the amount of S24 probe. Please note that the amount of each probe used was adjusted in order to increase signal from rare mRNA's such as the MDA6 mRNA and to relatively decrease the signal obtained from abundant mRNA's such as the S24 mRNA. Control reactions lacking RNA were blanc.

The amount of PSA mRNA can be compared to the results of Ishikawa et al (Jap. J. of Clin. Oncology, 28, 723–728; 1998). Using quantitative dot blot hybridisation, they found a very high expression in prostate RNA, but also expression of PSA mRNA (although at a 28 fold level) in Salivary gland RNA, Pancreatic RNA (48× lower level) and in many other tissues. this corresponds well with the results obtained by us using the MLPA method. The PSA signal obtained with prostate total RNA was 115% of the S24 signal strength. In salivary gland RNA 20%; In pancreas RNA 8% and in liver RNA only 2%. The signal obtained after PCR amplification with MLPA is non linear with the amount before amplification especially when using a limited number of probes. During the final amplification cycles annealing of complementary probes competes with primer annealing for abundant fragments. This is prevented by using larger number of probes as the amplification reaction stops by depletion of primers before extremely high amounts of fragments are produced.

EXAMPLE 3
Detection of mRNA's without Sequence Specific Clones.

In order to detect the S24 mRNA without the use of a enzymatic produced oligonucleotide containing a S24 specific DNA sequence, we produced single stranded DNA from M13 clone MRCH227. This clone contains a 268 bp. stuffer fragment derived from phage T7 inserted in M13 derivative MRCH214 described in example 1. Double stranded DNA of MRCH214 as well as a DNA fragment obtained by PCR from a T7 DNA template using primer SEQ ID NO:86 and 87 were both digested with Xba 1 and Sph 1 and ligated. An M13 clone containing the 268 bp T7 insert was designated MRCH227.

MRCH227 single stranded DNA was digested with EcoR5 and SpaH1 which is a true isoschizomer of Sph 1. Digestion was performed by incubation of 400 pMol MRCH227 single stranded DNA with 2.2 nMol of each of the oligonucleotides SEQ ID NO:29 and SEQ ID NO:88 and 8000 units each of EcoR5 and SpaH1 in 10 mM Tris-HCl pH 7,6; 100 mM KCl; 10 mM MgCl2 and 1 mM Dithiothreitol at 37° C. Following digestion for 1 hr, the DNA was phenol extracted, ethanol precipitated and dissolved in TE.

Figure 19:
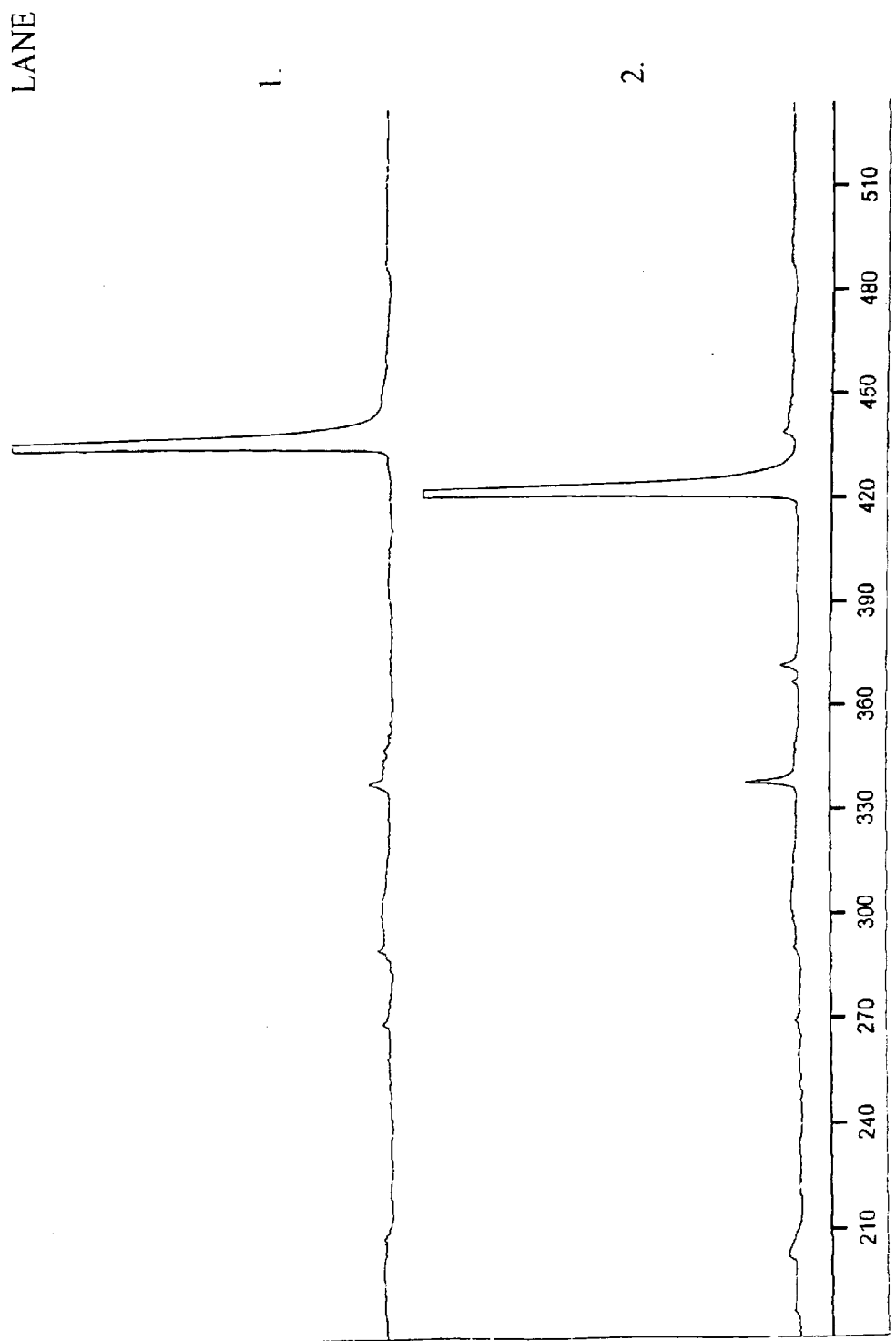
FIG. 19 shows the detection of a human mRNA without the use of a specific clone for that mRNA sequence.

A cDNA copy of the S24 mRNA was produced as described in example 2, starting with 50 ng total RNA of human adrenal gland tissue (Clontech) and 100 fMol reverse transcription primer SEQ ID NO:81. The ligation and PCR reaction were performed as described in example 2 except that the probe used consisted of a mixture of 5 fMol each of three chemically produced oligonucleotides SEQ ID NO: 77, 89 and 90 and 10 ng digested MRCH227 DNA. Oligonucleotide SEQ ID NO:89 was purified by PAGE and was phosphorylated with the use of T4-polynucleotide kinase. As can be seen in FIG. 12, oligonucleotide SEQ ID NO:90 binds both the MRCH227 DNA as well as oligonucleotide SEQ ID NO:89 and functions as a ligation-template. Oligonucleotides SEQ ID NO:77 and 89 can both be bound to, and aligned by DNA or cDNA containing sequences of the S24 gene. In the presence of S24 cDNA and oligonucleotide SEQ ID NO:90, the oligonucleotides SEQ ID NO:77 and 89 as well as the Sph1-EcoR5 fragment of clone MRCH227 can be ligated to one molecule which can be amplified using primers Seq. ID. 55 and 85 as described in example 1. The resulting amplification product has a length of 394 bp. and was indeed observed when only 50 ng of human total RNA was used as a template for the cDNA reaction (FIG. 19 lane 2).

As a control, the S24 mRNA was detected in a 5 ng sample of human total adrenal gland RNA using the probe described in example 2 consisting of Bsm 1 and EcoR5 digested MRCH213 single stranded DNA and oligonucleotide SEQ ID NO:77. The amplification fragment obtained has a length of 404 bp and is indeed observed in Lane 1.

The sensitivity of the assay with this latter assay, using two oligonucleotides, appeared to be 8 fold higher than the assay for S24 mRNA using the probe outlined in FIG. 12 that contains 4 oligonucleotides.

EXAMPLE 4
Relative Quantification of DNA Sequences:

Using denatured chromosomal DNA from either normal or cancer cells as a ligation template, and probes specific for oncogenes, the relative strength of the signals obtained for each probe after amplification will reflect the relative copy numbers of these oncogenes in the samples used. The absence of an amplification product of a particular probe in the DNA sample derived from cancer cells indicates the loss of both copies of the target sequence. A reduced amount of the amplification product of a particular probe relative to other probes and relative to results obtained with normal cells indicates loss of one copy of the particular target sequence (Loss of heterozygosity). A larger amount of amplification product of a particular probe relative to other probes and relative to results obtained with normal cells indicates amplification of the particular target sequence.

Figure 17:
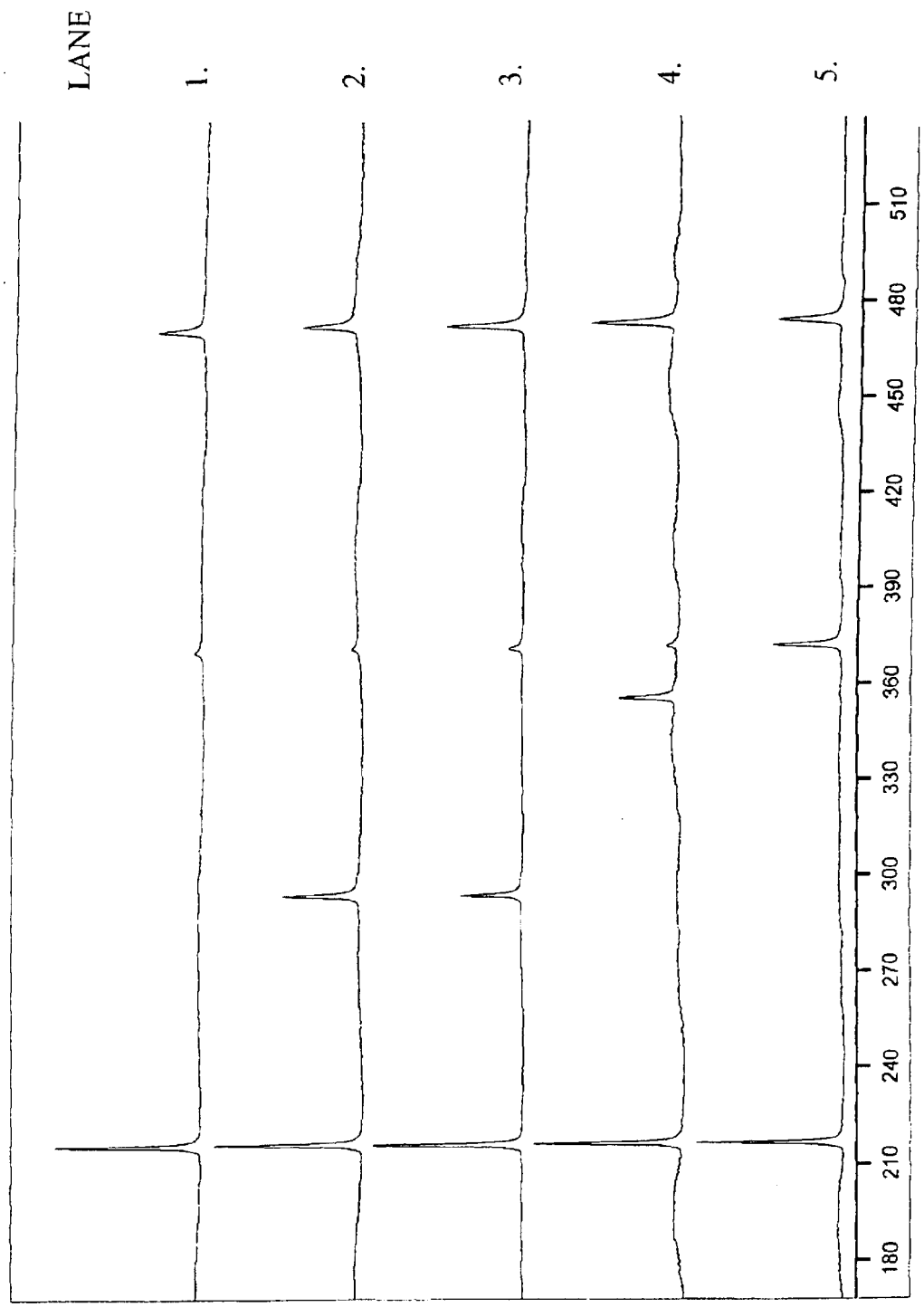

The approach is illustrated in lanes 2 and 3 of FIG. 17 (Example 6). Two probes recognising wild-type sequences are used as well as one probe recognising the relatively common deltaF508 of the human CFTR gene involved in cystic fibrosis. No amplification product specific for the deltaF508 probe is detectable when analysing DNA from non carriers (Lanes 1, 4 and 5). A small amount of delta F508 amplification product relative to the bands obtained with wild-type specific probes is detected when DNA from a person known to carry this mutation on one chromosome was used (Lane 3). A larger amount of amplification product of the deltaF508 probe as compared to the amplification products of the two wild-type probes, was detected when a sample of DNA from a person homozygote for this mutation was analysed (Lane 2).

EXAMPLE 5
Detection of Genomic Imprinting:

For genes in which the maternal and paternal derived copies differ in one or more single nucleotide polymorphisms, the relative amounts of transcription of these alleles can be determined by using probes specific for these SNP sites and by comparing the relative amounts of the amplification products of each SNP specific probe with the use of either cDNA or denatured chromosomal DNA as a ligation template. For some genes, transcription frequency of the maternal and paternal derived gene copies differ as a result of genomic imprinting.

EXAMPLE 6
Multiplex Detection of Nucleic Acid Sequences:

In order to rapidly screen samples for the presence of certain rare mutations/SNP's, probes can be used specific for these mutations/SNP's without the use of probes specific for the wild-type sequence or the common SNP variant. The appearance of an amplification product for these mutation specific probes can e.g. be tested on simple agarose gels or by real time PCR methods.

As an example, a series of probes was constructed for different mutations in the human CFTR gene. As in example 1, all probes of enzymatic origin contained non variable sequences adjacent to the site of the mutation, whereas the chemically produced probes contained the site of the mutation at or very close to the 3' end of the oligonucleotide. For each mutation to be detected a enzymatic produced probe 1 was provided (10 ng single stranded M13 clone DNA, digested with Bsm I and EcoR5 and each probe containing the same oligonucleotide tag used for the amplification reaction). For each mutation was also provided a chemically produced oligonucleotide probe 2, (4 fMol each) specific for the rare mutation sequence. Each combination of probes 1 and 2 specific for a certain CFTR mutation could give rise upon template directed ligation and subsequent amplification to an amplification product between 300 and 350 bp except for the probes specific for the more common deltaF508 mutation which could give rise to an amplification product of 260 bp.

In addition two probes for other wild-type CFTR sequences were provided as a control for correct processing of the samples. These wild-type probes could give rise upon template directed ligation and subsequent amplification to amplification products of respectively 200 and 400 bp. An outline of the assay is provided in FIG. 5.

Two different PCR fragments derived from phage T7 DNA with the use of the following primer pairs were inserted in the MRCH214 vector described in example 1: SEQ ID NO:91+92; 93+94. These 2 PCR fragments were digested with Sph 1 and Xba 1 and ligated to Sph 1 and Xba 1 digested d.s.DNA of phage MRCH214. Primers SEQ ID NO:91 and 93 have an Sph 1 site close to their 5' end. Primers SEQ ID NO:92 and 94 have an Xba 1 site close to their 5' end. Phage T7 is available from the American Type Culture Collection. As a result two different phages were obtained that each have a DNA sequence of different length between the Bsm 1 site and the nucleotides 77–112 (sequence tag Y) of SEQ ID NO:18: MRCH287 has a 331 bp T7 fragment inserted and MRCH294 contains a 232 bp stuffer T7 fragment.

In each of the three different clones containing a T7 stuffer fragment an oligonucleotide was inserted into Bsm 1 and Sph 1 digested double stranded DNA. Each oligonucleotide is identical to the sequence at the 3'-side of a known mutation in the human CFTR gene (Genbank seq. nr. M55108–M55130).

The partially complementary oligonucleotides SEQ ID NO:95 and 96 were inserted in the Bsm 1 and Sph 1 digested MRCH287; SEQ ID NO:97+98 in MRCH292 described in example 2; SEQ ID NO:99+100 in MRCH294, resulting respectively in phage clones MRCH261, 308 and 314. Single stranded phage DNA from these three clones was produced as described by Reddy, P. and McKenney K. (Biotechniques 20: 854–860; 1996). This single stranded DNA was annealed to two oligonucleotides: Seq ID NO:29+ 101 for the MRCH261 DNA; SEQ ID NO:29+102 for MRCH308 DNA and SEQ ID NO:29+103 for MRCH314 DNA. Digestion was performed as described in example 1.

For each mutation to be tested one oligonucleotides was synthesised containing a common part used to amplify ligated oligonucleotides (Sequence tag X), and a part complementary to the CFTR sequence at the position of the mutation. The site of the mutation is at the penultimate position or at the 3' end of the oligonucleotide.

Oligonucleotide SEQ ID NO:104 can anneal to a site adjacent to the insert of clone M308 on human CFTR gene DNA containing mutation 1717–1G>A. Oligonucleotide SEQ ID NO:105 can anneal to a site adjacent to the insert of clone M314 on human CFTR gene DNA containing mutation R1162X. Other clones and oligonucleotides used are described in example 1.

DNA of five different humans (50–200 ng in TE) was mixed in a 200 ul vial with the following probes: 4 femto-Mol EcoR5 and Bsm I digested MRCH236 DNA described in example 1+4 femtoMol oligonucleotide SEQ ID NO:47+6 femtoMol oligonucleotide SEQ ID NO:48 which together give rise to an amplification product of 193 bp on human DNA having a wild-type sequence in intron 4 of the CFTR gene.

4 FemtoMol EcoR5 and Bsm I digested MRCH261 DNA +5 FemtoMol oligonucleotide SEQ ID NO:106+5 Femto-Mol oligonucleotide SEQ ID NO:107 which together give rise to an amplification-product of 436 bp on human DNA having a wild-type sequence in exon 20 of the CFTR gene.

4 FemtoMoi EcoR5 and Bsm I digested MRCH243 DNA described in example 1+10 FemtoMol oligonucleotide SEQ ID NO:50 which together give rise to an amplification product of 269 bp on human DNA having a delta F508 mutation (deletion) in exon 10 of the CFTR gene.

4 FemtoMol EcoR5 and Bsm I digested MRCH308 DNA+10 FemtoMol oligonucleotide SEQ ID NO:104 which together give rise to an amplification product of 326 bp on human DNA having the 1717–1G>A mutation in intron 10 of the CFTR gene.

4 FemtoMol EcoR5 and Bsm I digested MRCH314 DNA+10 FemtoMol oligonucleotide SEQ ID NO:105 which together give rise to an amplification product of 341 bp on human DNA having the R1162X mutation in exon 19 of the CFTR gene.

Target DNA denaturation, probe annealing, template directed probe ligation and amplification were as described in EXAMPLE 1 except that the annealing reaction was for 16 hrs at 60° C. Detection of amplification products was performed on ethidium bromide stained 1.8% agarose gels or on acrylamide gels with fluorescent detection as described in example 1.

Results obtained using 50–200 ng samples of human chromosomal DNA are shown in FIG. 17. In a control sample of human DNA (Lane 1) only the two probes specific for wild-type sequences give rise to an amplification product (193 & 436 bp.). Samples 2 and 3, known to be derived from a deltaF508 homozygote and a deltaF508 heterozygote respectively give in addition to the 193 and 436 bp bands rise to an amplification product of 269 bp. Sample 4, known to be derived from an individual with a 1717–1G>A mutation on one of the chromosomes gives rise to a band of 326 bp in addition to the 193 and 436 bp bands. Sample 5 was derived from an individual having a R1162X allele and gives an amplification product of 341 bp in addition to the 193 and 436 control bands.

The relative amount of amplification product specific for the control sequences has been reduced compared to the amount of amplification product specific for the CFTR mutations by providing an oligonucleotide capable of annealing to the control sequence and preventing the annealing of the control wild-type specific short probe.

EXAMPLE 7
Detection of Microorganisms, Parasytes or Pathogens.

In order to detect a specific micro-organism, parasite and/or pathogen, probes were designed for a ribosomal RNA sequence that is unique to this organism or a specific variant of this organism. From a sample total nucleic acids are isolated. from this nucleic acid sample, cDNA is prepared using a primer specific for the ribosomal RNA to be detected, reverse transcriptase, dNTP's and a suitable buffer. The cDNA is made single stranded e.g. by RnaseH treatment, alkali treatment or heat denaturation, and used as a ligation template for the probes.

When using several probes, each specific for a particular organism, or variant of an organism, and each giving rise to an amplification product of unique size, several nucleic acid sequences/organisms can be identified in a single assay.

As a control for the sensitivity of the assay and the release of RNA from bacteria during the RNA purification, a specific amount of a unique RNA sequence or a small number of bacteria containing a unique RNA sequence can be added to the sample when starting the nucleic acid purification.

A microbial cell contains approx. 25,000 ribosomes. When the goal is to detect a minimum of 1 Agrobacterium cell in 10 mg plant tissue, 10.000–20,000 copies of a control RNA sequence generated e.g. in vitro by methods known in the art, can be added to the 10 mg plant tissue immediately preceding the isolation of the total nucleic acids. To a sample of approx. 1 ug of the purified RNA, reverse transcriptase primers specific for the agrobacterium ribosomal RNA and the control RNA sequences are provided and cDNA is made as described in example 3. Following the reverse transcription reaction a MLPA assay is performed as described in examples 1–3, using e.g. two probes for the control RNA and four probes for regions of the agrobacterium ribosomal RNA that are quite specific for this organism. In the absence of Agrobacterium cells only the probes specific for the control RNA will be amplified and will generate two bands detectable on agarose gels. In the presence of Agrobacterium cells the probes specific for the agrobacterium ribosomal RNA will generate stronger bands than the control bands even when only one bacterial cell was present in the sample. Care has to be taken during nucleic acid isolation that not only the plant cells, but also bacterial cells are disrupted. As an alternative control a defined number of intact microbial cells containing a unique RNA or DNA sequence can be added to the plant sample to be analysed.

EXAMPLE 8
Complete Probes.

The presence of two different human mRNA in samples of total RNA from 2 different human tissues was determined with the use of two complete probes.

Samples of total RNA from human prostate and salivary gland were purchased from Clontech Company.

DNA fragments complementary to the human ribosomal protein S24 and the human prostate specific antigen were made with the use of the polymerase chain reaction using 5 ng human genomic DNA (Promega) as a template and oligonucleotides SEQ ID NO:1 & 2 (prostate specific antigen) or SEQ ID NO 3 & 4 (ribosomal protein S24) as PCR primers. These primers contain a part complementary to the DNA fragment to be amplified, as well as a part to be used in the detection reaction. PCR conditions were: 2 minutes denaturation at 95° C.; 30 cycles of 30 seconds denaturation at 95° C., 30 seconds annealing at 60° C. and 60 seconds elongation at 72° C. The concentration of the PCR fragments were estimated by ethidium bromide stained agarose gel-electrophoresis with standards. The PCR fragments were used without purification.

The hybridisation selection reaction was carried out in a 500 ul eppendorf tube containing the following 12,9 ul deionised formamide, 0.5 ul of the RNA sample (0.5 ug RNA), 0.2 ul each of the two PCR fragments (~5 ng DNA), 0.5 ul biotin-dT43 (SEQ ID NO 7, 50 pMol/ul, dissolved in TE), 1 ul of Rsa 1 digested Lambda DNA (0.5 ug/ul). This mixture was incubated for 5 minutes at 65 ¦C. in order to denature the probe DNA fragments. To this mixture was added 2,6 ul water and 8,1 ul 20×SSC. Hybridisation was performed by incubation for 2 hrs at 42 ¦C, after which 80 ul of paramagnetic streptavidin particles were added. The paramagnetic streptavidin particles (SA-PMP) preparation consisted of 40 ul SA-PMP's (Promega)+40 ul denatured herringsperm DNA (0.5 mg/ml) mixed 20 minutes before use. After incubation at room temperature for 15 minutes in order to allow the binding of the oligo-dT-biotin to the streptavidin-particles, the streptavidin-particles were collected with the use of a magnet (Promega) and washed 4 times at room temperature with 1 ml. 0.5×SSC+0.1% SDS, twice with 0.5×SSC and twice with 20×SSC. The particles were transferred to a clean tube and washed twice in 1×PCR buffer (10 mM Tris-HCl pH 8.5; 50 mM KCl and 1.5 mM MgCl2). The particles were finally suspended in 50 ul 1×PCR buffer containing 10 ug/ml RNaseA (Roche biochemicals). After incubation for 10 minutes at room temperature, the particles were removed by centrifugation and the supernatant collected. To 10 ul of this supernatant was added 40 ul PCR buffer, 15 pMol of the two PCR primers (SEQ ID NO 5 and 6), 1 unit taq polymerase and dNTP's to a final concentration of 100 uM each. One of the PCR primers (SEQ ID NO 5) is fluorescent labelled as it contains a FITC group covalently bound to its 5'-end.

Figure 20:
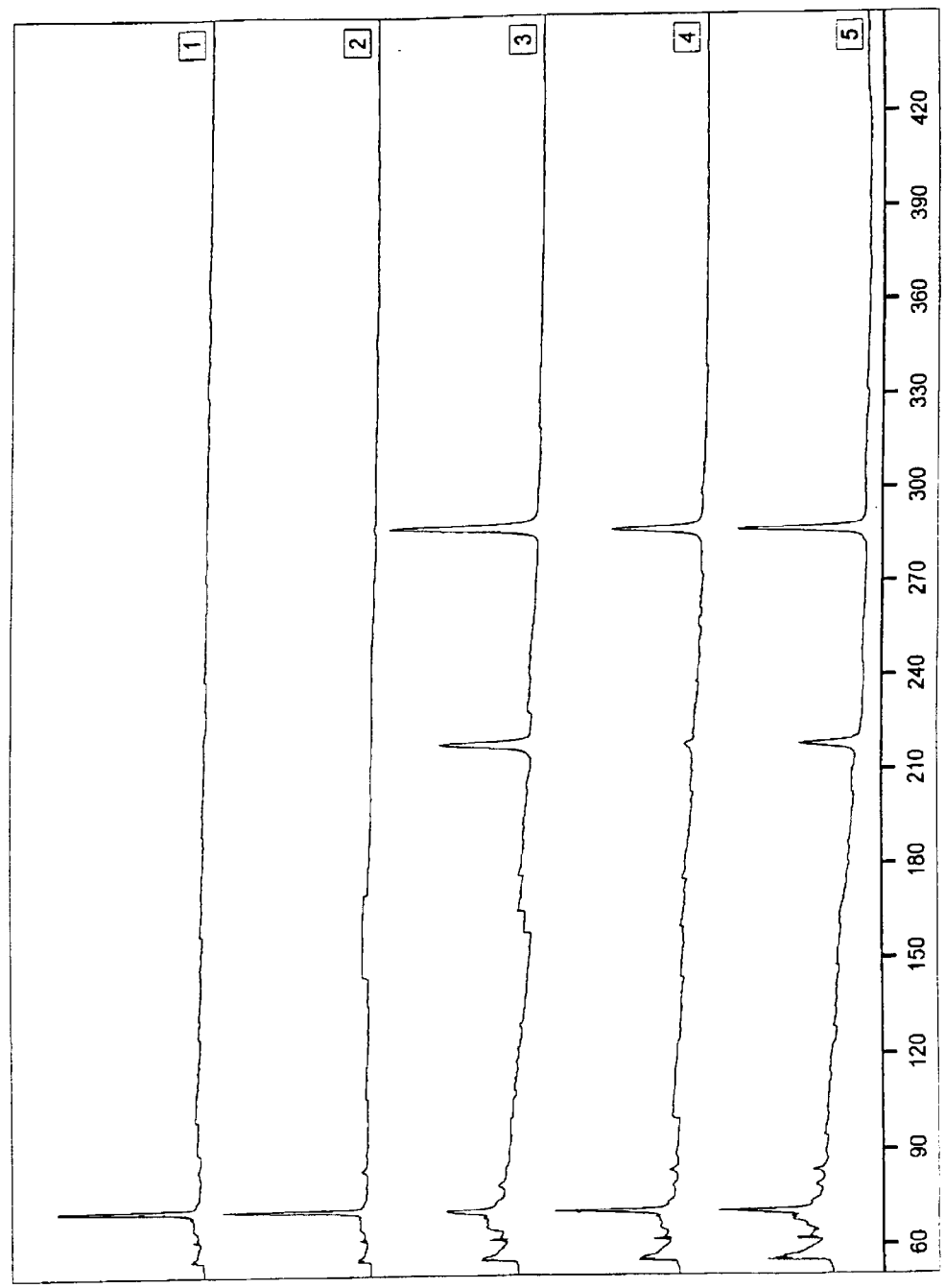
FIG. 20 shows the results obtained with two complete probes on human total RNA samples.

After addition of 3 drops paraffin oil, the samples were submitted to 30 cycles of PCR. PCR conditions were 2.5 minutes 95° C., followed by 30 cycles of 30 seconds denaturation at 95° C., 30 seconds annealing at 60° C. and 60 seconds elongation at 95 |C. After mixing with a formamide containing loading solution and denaturation, 0.5 ul of this PCR reaction was analysed on a 6% acrylamide gel containing 7 M urea in Pharmacia ALF apparatus. The results are shown in FIG. 20. A graphic outline of the method used to detect and quantify mRNA's with the use of complete probes is shown in FIG. 15.

Lanes 1–3 are control reactions. Lane 4 shows the results obtained with RNA from salivary glands. Lane 5 shows the results obtained with RNA from prostate tissue.

No RNA was added to the hybridisation reaction for the sample shown in Lane 1. Lane 2 was a reaction with prostate RNA, but no biotin-dT43 was added. In lane 3, both DNA fragments used as probe (lpgram) were added to the PCR reaction as a positive control.

The two peaks at 218 and 286 minutes correspond to fragment-lengths of 196 and 267 nucleotides as compared to DNA markers in a different lane. This is very close to the expected size of the fragment specific for the prostate specific antigen (195 nucleotides) and the expected size of the ribosomal protein S24 fragment (265 nucleotides). The size of the S24 peak in lane 4 is 12.1 times larger as the size of the psa specific fragment. In lane 5, the size of the S24 peak is only 2,1 times larger than the psa peak. The S24 mRNA is expected to be present in most if not all human tissues. The prostate specific antigen has been detected in several human tissues, but is expected in a relatively larger amount in human prostate tissue.

Identical results were obtained if 100 times less template was used in the amplification reaction, suggesting that even without optimisation of the hybridisation conditions, RNA samples of less than 10 ng might be sufficient for MLPA experiments using complete probes. The control reactions shown in lanes 1 and 2 remained blank when the PCR reaction was extended to 45 cycli.

EXAMPLE 9

Detection of DNA Methylation:

The genomic DNA of some genes may be more or less modified by cytosine methylation in different tissues or under different growth conditions. Methylation can be detected by digestion with pairs of restriction endonucleases wherein one isoschizomer is sensitive and the other is insensitive to methylation. An example are the enzymes Hpa II and Msp I, both recognising the DNA sequence CCGG and both commercially available from several sources including New England Biolabs. Digestion by Hpa II is blocked when one of the two cytosine residues in the recognition site is methylated, whereas methylation of the internal cytosine residue does not affect Msp I digestion.

By choosing a MLPA probe hybridising to a DNA sequence containing a Hpa II/Msp I site close to the site of ligation, formation of amplifyable ligated probes is prevented when the target DNA is unmethylated and the target DNA is digested with either Hpa II or Msp I before denaturation and hybridisation to the probes, whereas amplifyable ligated probes are obtained when using Hpa II digested target DNA in case part or all of the target DNA is methylated at the internal C of the CCGG sequences.

In case the sample DNA is purified as a chromosomal complex and is not digested with a restriction-endonuclease but with increasing amounts of DNAse I, the amount of signal obtained with the various probes will reflect the DNAse I hypersensitivity of the particular genes which differs between active and inactive genes and in some cases differ between maternal and paternal inherited copies of a gene.

EXAMPLE 10

Determination of Haplotypes:

Usually only particular combinations of polymorphisms in a certain chromosomal region are present in a population. Such a combination is called a haplotype. It has for instance been shown that in the Dutch population only five out of eight possible combinations of four polymorphisms in the human TNF gene are present (Crusius J B A et al, Eur.Cytok.Network, 1994;2:168.). In order to determine the haplotypes in a particular chromosomal region, DNA is tested for polymorphisms using an assay as described in example 1. In case more than one locus is heterozygote, primers are designed ending at the outermost polymorphism site, one primer being specific for allele A and the other for allele B. These primers are used to amplify either the chromosomal copy of allele A or the chromosomal copy of allele B, for instance by linear amplification using repeated cycles of denaturation, primer annealing and primer-elongation. Following amplification the DNA is again tested for the polymorphisms present as described in example 1.

EXAMPLE 11

Determination of the Site of a Chromosomal Breakpoint.

Chromosomal instability is encountered in most cancer cells. Rearrangements in which part of one chromosome is linked to a part of another chromosome is usually detected by histological methods. Some rearrangements are very common in particular types of cancer. Often specific chromosomal regions are involved but exact breakpoints in each region differ between different patients. As an example the chromosomal rearrangement called the Philadelphia chromosome is encountered in many cases of leukemia and involves the linking of part of the BCR gene with part of the ABL gene which are located on different chromosomes. The exact breakpoint can be anywhere in the first intron of these genes and may differ as much as 70.000 bp between different cases. Philadelphia chromosomes can be detected both histologically as well as with the use of RT-PCR on RNA from the cancer cells. Knowing the exact chromosomal breakpoint site is very useful. This information can be used to design primers that can be used to detect DNA fragments specific for cancer cells and not present in wild-type cells of the patient by for instance (nested) PCR. This can make detection of a single cancer cells in more than a thousand other cells possible and can be used to follow the effect of a therapy.

In order to determine the exact site of the chromosomal breakpoint, a sample containing chromosomal DNA in single stranded form is provided with a large number of chemically synthesised type A probes. These probes each contain at the 3' end a different sequence complementary to a part of one of the chromosomal region involved at distances of approximately 1000 bp and each probe contains the same sequence tag, 5' of the hybridising sequence. In addition a large number of chemically synthesised probes B are provided to the sample each containing at the 5' end a different sequence complementary to the second chromosomal region involved at distances of approximately 1000 bp and each containing a second sequence tag 3' of the hybridising sequence. Following incubation of the chromosomal DNA with the probes under conditions allowing hybridisation of complementary sequences, the 3' ends of the type A probes are elongated by a DNA polymerase such as sequenase (exo- T7 DNA polymerase), the Klenow fragment of E. Coli DNA polymerase I or the Kienow fragment of Taq polymerase. The DNA polymerase used has preferably no or only a limited amount of strand displacement activity. Probes of which the elongated 3' end have become adjacent to the 5' end of a type B probe can be connected by ligation and can be amplified with the use of a primer complementary to the sequence tag of the type B probe and a primer essentially identical to the sequence tag of the type A probe.

The resulting amplicons are separated on size and analysed in order to determine which probes have become connected and/or analysed by sequence determination in order to find the exact site of the chromosomal breakpoint.

If the distance between the different probes is approximately 1000 bp, the resulting amplicons will be between 40 and 2000 bp. In contrast to multiplex amplification methods described in the other examples, only one amplicon is expected. As the size of this amplicon is most often larger than 500 bp, it is possible to chose the sequence tags of the type A and the type B probes to be each others complement thereby permitting the use of only a single primer during the amplification reaction. PCR reactions in which only one primer is used are efficient for amplification of longer fragments and have the advantage that amplification of short fragments such as primer dimers is reduced due to the formation of hairpin-structures in the amplicons.

One of the main differences between the approach used in this example and ordinary multiplex PCR with multiple primers is that the concentration of probes used in MLPA reactions is typically 10.000 fold lower than in ordinary multiplex PCR reducing the chance on artefacts and formation of primer dimers. Only during the final PCR reaction high concentrations of primers are used, but only of one primer pair specific for the sequence tags common to all probes.

As an example of this approach, we generated two probes specific for sequences of exon 11 (Genbank acc. Nr. M55116) of the human CFTR gene that bid to target sequences which are at a distance of 95bp from each other and filled the gap with a polymerase (sequenase; exo- T7 DNA to polymerase) followed by a ligation reaction to connect the probes that became adjacent and an amplification reaction. Using 0.5 ug human chromosomal DNA (provide the target CFTR sequences, we indeed observed the expected 383 bp amplification product consisting of 49 bp of CFTR sequence +sequence tag of probe SEQ ID NO:113, 95 bp CFTR sequence that was filled in by the polymerase, the 42 bp CFTR sequence of probe M245, the 169 bp stuffer sequence of probe M245, 5 bp between the CFTR sequence and the stuffer region of M234 and 23 bp of primer SEQ ID NO:56. The presence of the CFTR sequence between the probes was confirmed by digestion of the amplification product with Dra III which has a recognition sit at nucleotide 350–358 of sequence M55116, producing fragments of 298 and 85 bp. (not shown).

The probes used were 4 femtomol of a oligonucleotide containing a tag at its 5' end and a CFTR sequence at its 3' end SEQ ID NO:113; complement of nucleotides 389–418 of Genbank sequence M55116) and 10 nanogram of digested single stranded M13 clone M234 containing 169 bp stuffer DNA between the sequence tag and the 42 nucleotides CFTR specific sequence (Complement of nucleotides 252–293 of Genbank sequence M55116). Clone M234 was prepared as described in example 1 by inserting 169 bp PCR fragment of phage T7 DNA obtained with primer SEQ ID NO:108+109 in clone M214. In the clone obtained (M275), a double stranded synthetic DNA fragment (SEQ ID NO:110+111) was inserted. Single stranded DNA from the clone obtained (M245) was digested with EcoR5 and Bsm I in the presence of oligonucleotides SEQ ID NO:112 and SEQ ID NO:29 as described in example 1.

0.5 ug human chromosomal DNA (Promega Corp.) was mixed with 4 femtomol probe SEQ ID NO:113 and 1 ng robe M245 and was diluted with water to 8.5 ul. The DNA was denatured by heating 5 minutes at 98° C. in a UNO 2 thermocycler with heated lid. To the DNA was added 1.5 ul of a salt solution (1500 mM KCl; 300 mM T is-HCl pH 8.5; 1 mM EDTA.). Annealing of the probes to the target DNA was for 16 hrs. at 60° C. in a thermocycler with heated lid. After decreasing the temperature to 37° C., to the mixture was added 40 ul dilution-buffer (2 mM MgCl2; 1 mM NAD+; 5 mM Tris-HCl pH 8, 5 and 62,5 uM of each dNTP.) and 1.5 units sequenase. The mixture was incubated for 5 minutes at 37° C. After increasing the temperature to 60° C., 10 units Ligase-65 were added and incubation was for 15 minutes at 37° C. followed by 5 minutes enzyme inactivation at 95° C. 10 ul of the mixture was used as a template for a PCR reaction in a 50 ul volume containing 2 units Taq polymerase; 15 mM Tris-HCl pH 8.5; 50 KCl; 1.5 MgC 2 and 0.01 Triton X-100.

After heating the mixture to 65° C., 10 pMol each of PCR primers SEQ ID NO:55 and SEQ ID NO:56 were added to provide a hot start.

PCR was performed in 200 ul tubes in a Biometra Uno 2 thermal cycler using the following conditions:

2.5 minute denaturation at 95 C.

40 cycles consisting of 30 second denaturation at 95 C; 30 second annealing at 60 C and 60 second elongation at 72 C. Following the PCR reaction, 10 ul of this reaction was analysed on a 1.8% agarose gel.

EXAMPLE 12

DNA samples derived from a female, a male or from the cell line SKBR3 were tested with three different mixes of MLPA probes each containing 4 femtomoles of each of 37–38 probe pairs. Probes were made as described in examples 1 and 2. A list of the genes towards which these probes were directed, their chromosomal locations and the length of their amplification products is presented in FIG. 24. Each probe pair was designed to detect a unique chromosomal DNA sequence of the particular gene.

Tests were performed on 100 ng samples of the DNA essentially as described in example 1. DNA in 5 ul TE was denatured by heating 5 minutes to 98° C. To the samples was added 1.5 ul TE containing 4 femtomoles of each probe+1.5 ul 1500 mM KCl; 350 mM Tris-HCl pH 8,5; 1 mM EDTA. After mixing, the reactions were heated for 1 minute at 95 ° C. followed by a 16 hrs. incubation at 60° C.

While at 60° C., 30 ul 2,67 mM MgCl2; 0.2 mM NAD; 5 mM Tris-HCl pH 8,5 and containing 1 unit Ligase-65 was added to the samples. The reactions were mixed and incubated 1 t 60° C. for 15 minutes followed by a 5 minute 98° C. incabation. After lowering the temperature to 60° C., to the samples was added 10 ul of a mix containing 0.25 mM of each dNTP; 10 pMol of the two PCR primers SEQ ID 55 (either IRD-800 or D4-labeled) and SEQ ID 85; 5 mM Tris-HCl pH 8,5; 20 mM KCl; and 2.5 units Taq Polymerase.

Separation of amplification products was performed on a LICOR IR2 DNA Analyzer (IRD-800 label; denaturing 25 cm gel containing 6,5% acrylamide) or a Beckman CEQ2000 capillary electrophoresis apparatus (D4-label) according to the instructions of the manufacturer.

Figure 25:
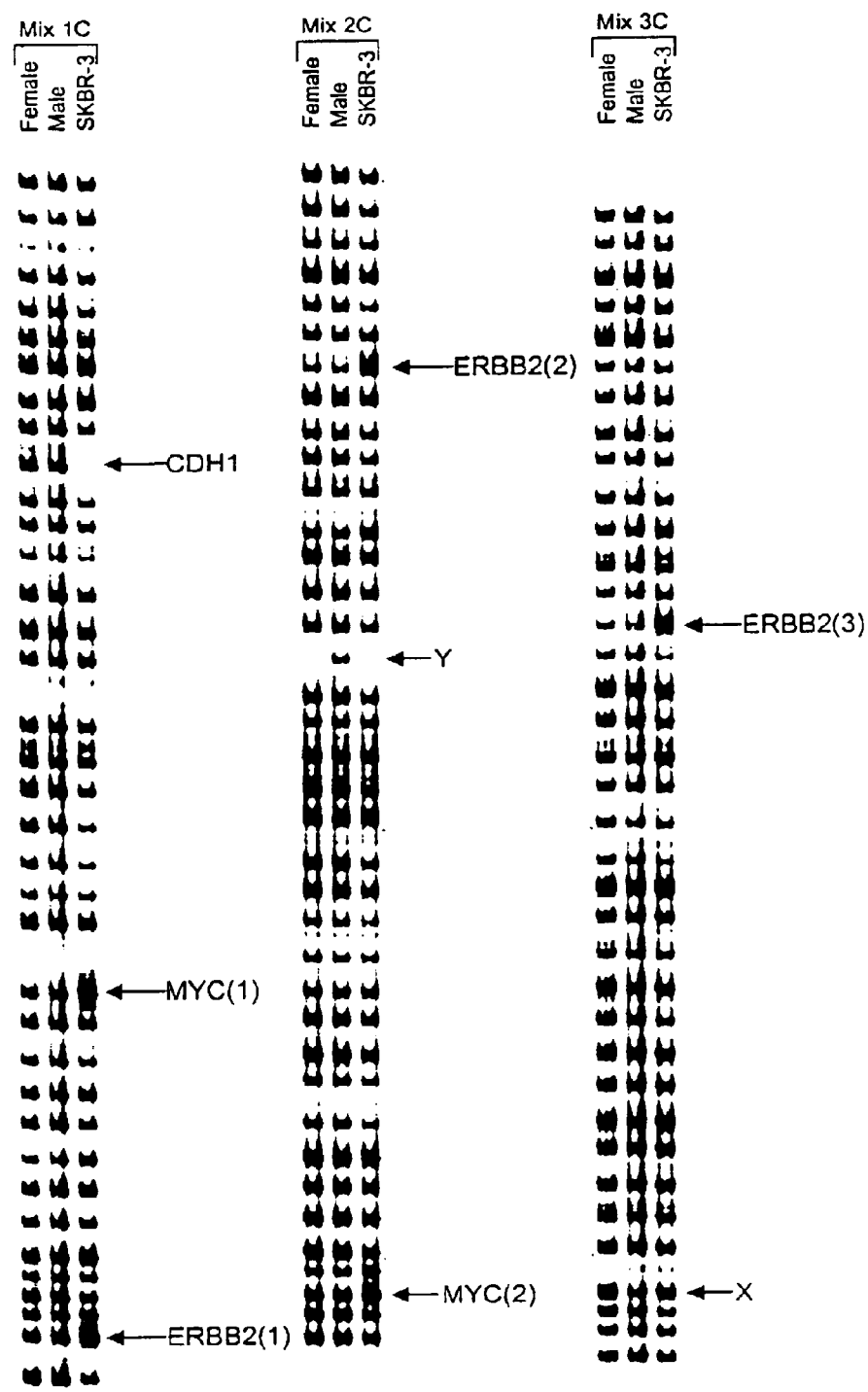
FIG. 25 shows a gel image of probe amplification products obtained upon MLPA analyses of three DNA samples as described in example 12.
Figure 26A:
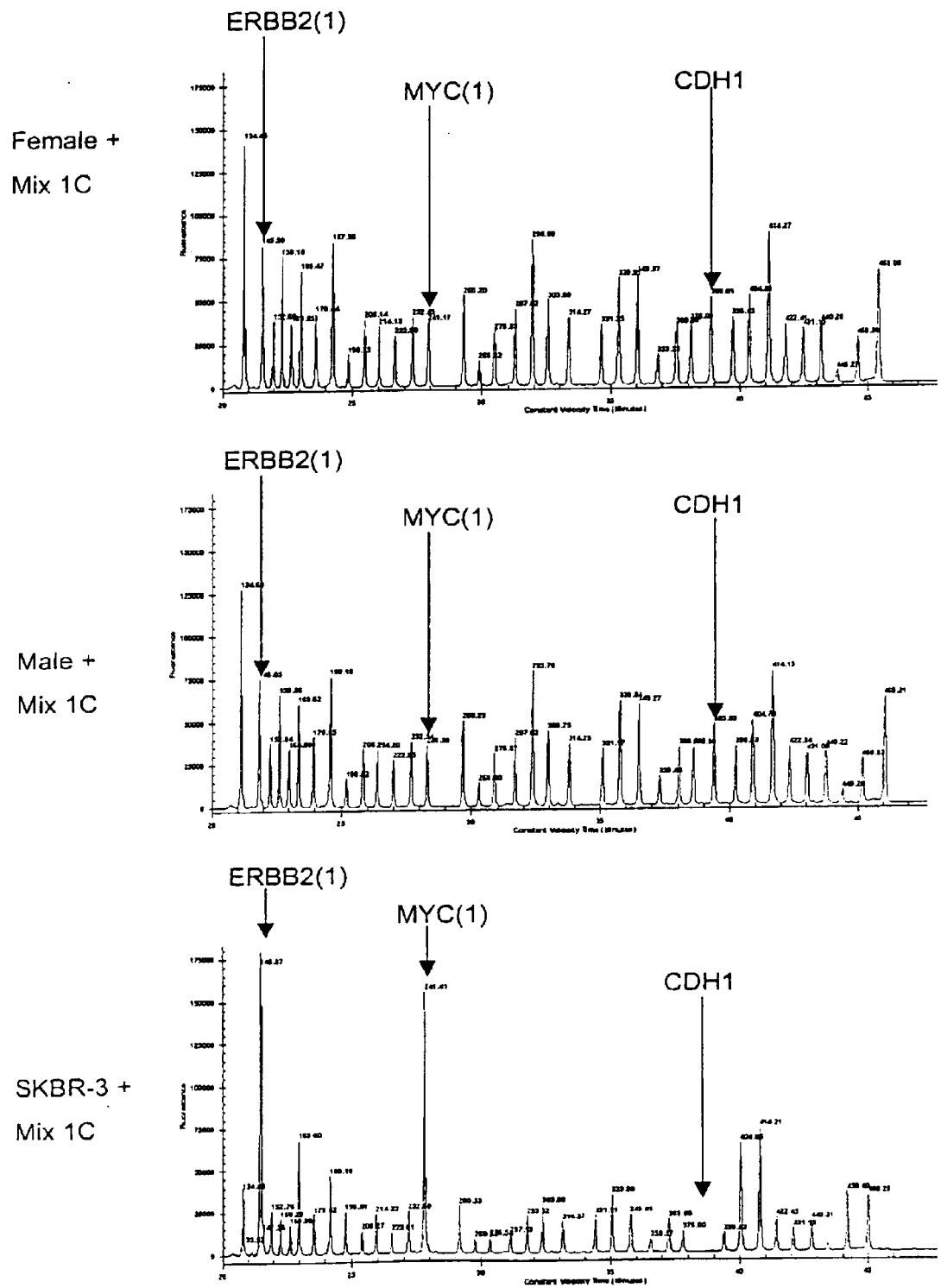
Figure 26B:
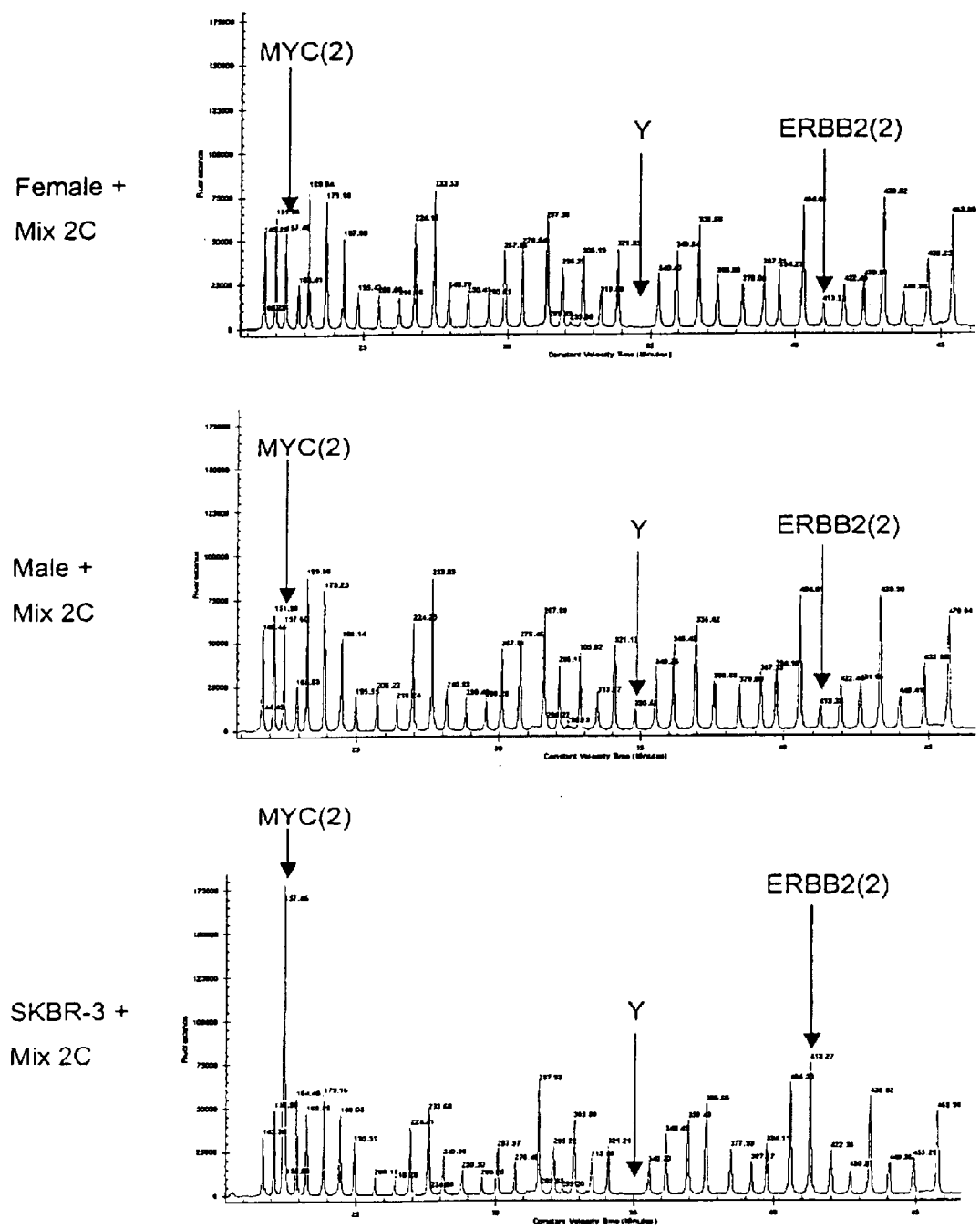
Figure 26C:
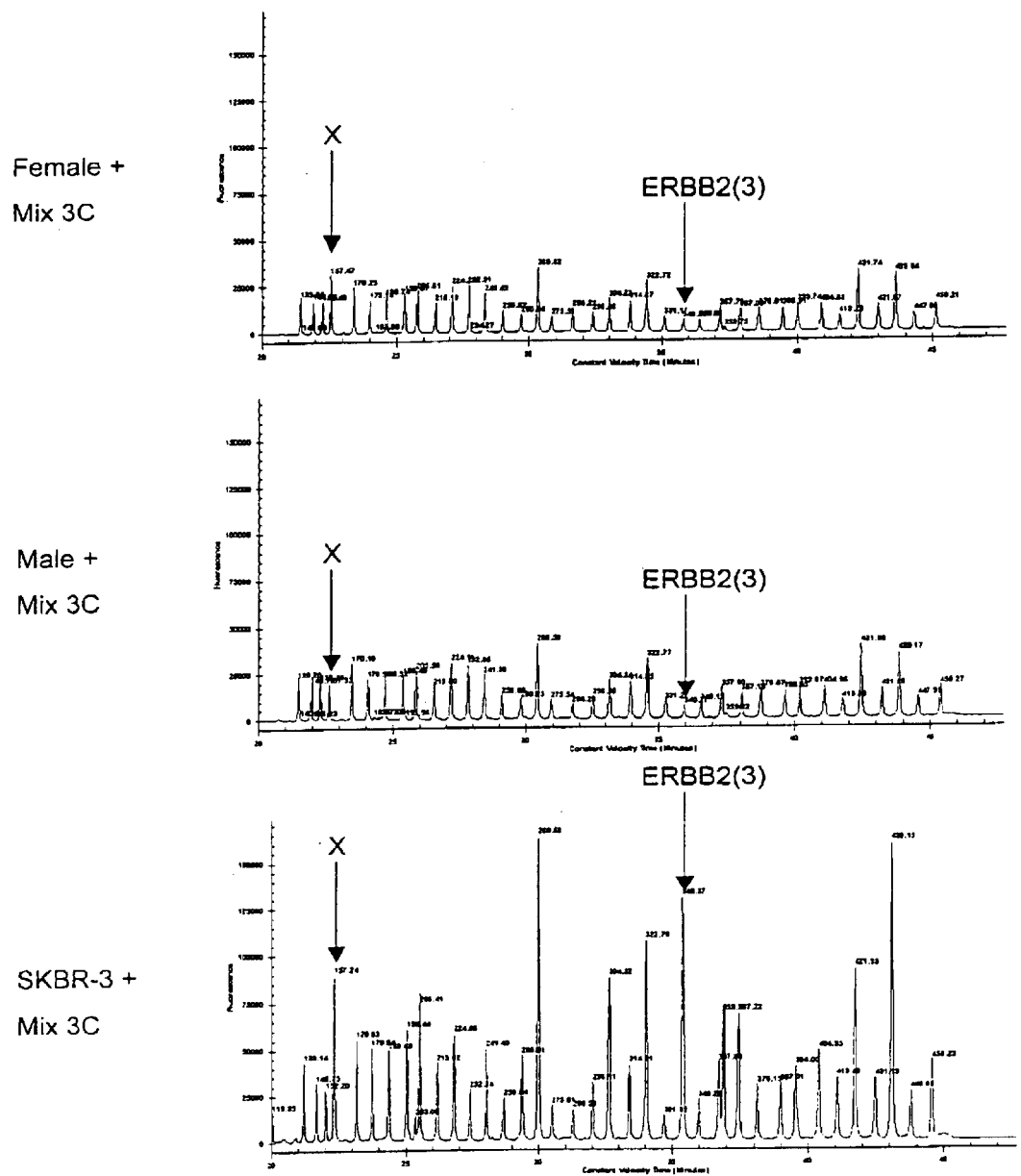

Results are shown in FIG. 25 (Licor) and FIGS. 26A, 26B and 26C (Beckman). The results obtained from the analysis on the Beckman apparatus was used for comparison of relative peak areas. Some of these results are summarized in FIG. 28. Female and male DNA samples differ in the presence or absence of the Y-chromosome and in the number of copies of the X chromosome present. The cell line SKBR3 is known to contain an amplified ERBB2 locus. We noticed that the MYC locus is also amplified and that both copies of the CDH1 gene on chromosome 16q22.1 are missing.

FIG. 24. List of genes represented in probe mix 1c, 2c and 3c. Used are the HUGO names for the genes towards which the probes were directed as used by the Unigene resource of the National Centre for Biotechnology Information (www.ncbi.nlm.nih.gov/unigene). Also shown are the chromosomal locations of these genes and the size of the amplification products obtained from the probe pairs used, in basepairs.

FIG. 25. Gel image obtained after electrophoresis on a Licor IR2 DNA analyser. Only the region of the gel between 125 and 470 bp. is shown. Arrows indicate the sites of amplification in the case of ERBB2 (Chr. 17q21.1) and MYC (Chr. 8q24.12), deletion in the case of CDH1 (Chr. 16q22.1), the presence of the SRY locus of the Y-chromosome in the male DNA sample and the presence of one or two copies of the X chromosome in the male and female DNA sample respectively. Apart from the CDH1 loss and the MYC and ERBB2 amplification, the DNA of the SKBR3 cell line has several loci with a change in copy number.

FIG. 26. Peak profiles obtained with the Beckman CEQ 2000XL DNA analysis system. By comparing the relative peak area of a probe pair amplification product obtained on a test sample with the corresponding value obtained on control DNA, the relative gene copy number in the sample can be estimated.

FIG. 26A. Profile obtained with the use of probe mix 1C. Arrows indicate the probe amplification products of the first ERBB2 and the first MYC specific probe pairs that appear to be amplified in cell line SKBR3 as well as the amplification product of the CDH1 specific probe pair.

FIG. 26B. Profile obtained with the use of probe mix 2C. Arrows indicate the probe amplification products of the second ERBB2 and the second MYC specific probe pairs that appear to be amplified in cell line SKBR3 as well as the presence or absence of the amplification product of a probe pair specific for the SRY region on the Y chromosome.

FIG. 26C. Profile obtained using probe mix 3C. Arrows indicate the probe amplification products of the third ERBB2 that appears to be amplified in cell line SKBR3 as well as the amplification product of a probe pair specific for the AR gene located on chromosome X.

FIG. 27. Comparison of the relative peak area values (=percentage of the total area of all peaks between 130 and 463 bp. in that lane). The relative peak area values obtained for the female DNA sample were compared with the corresponding relative peak value of the male DNA sample (top) and of the SKBR3 DNA sample (bottom) The three ERBB2 probe pairs and the two MYC probe pairs are specific for DNA sequences in different regions of these genes.

EXAMPLE 13

In order to test reproducibility of MLPA results and the possibility to detect small deletions in the human genome, DNA from 12 individuals was tested with three different MLPA mixes containing 37–38 probe pairs each. DNA samples were provided by Dr. G. Pals of the Free University of Amsterdam. DNA samples were obtained from 12 healthy individuals, 2 of whom were known to have a deletion of one copy of exon 13 of the BRCA1 gene, and 6 were known to contain a deletion of exon 22 of this gene (Petrij-Bosch A, et al., Nat Genet.1977 Nov;17(3):341–5). Reaction conditions were as described in example 1 except that only 4 femtomoles of each probe was used and that one of the PCR primers was labelled with a D4 fluorescent group (Research Genetics). Approximately 100 ng DNA was used for each test. Detection of amplicons was done by capillary electrophoresis using a Beckman CEQ2000 apparatus. All 112 different probe pairs yielded a detectable amplification product. Fluorescence peak areas were measured and relative peak areas were calculated by dividing the peak area through the total area of all peaks in that sample. For each probe pair the average relative peak size was calculated. It appeared that for only 7 probe pairs the standard deviation of the average relative peak area was higher than 10% (respectively 11; 12; 12; 12; 13; 15 and 175).

The relative peak area of a probe pair specific for the exon 13 sequence of BRCA1 was 50% (S.D.<1%) in the two samples known to have a deletion of this exon in one gene copy as compared with the average relative peak area of the other 10 samples. Standard variation of these other 10 samples was below 4%.

The relative peak area of a probe pair specific for exon 22 sequence of the BRCA1 gene was 50% (S.D.<7%) in the 6 samples known to have a deletion of one gene copy of exon 22 as compared to the average relative peak area of the other 6 samples. Standard deviation for this probe in the other 6 samples was below 10%. These results clearly establish the possibility to use MLPA for gene multiplex copy determinations in human chromosomal DNA samples.

EXAMPLE 14

Nine total RNA samples derived from different human tissues were analysed with a mix of 34 MLPA probe pairs. Probes were made as described in example 1. Probe pairs were designed to produce amplification products ranging from 130 to 409 bp upon successful ligation. Each probe pair was designed to detect a unique cDNA sequence of an mRNA derived from the particular gene and should not detect chromosomal DNA as the recognition site of one of the probes of each probe pair was interrupted by an intron sequence. For each probe pair a gene-specific reverse transcription primer was used located within 25 nucleotides downstream in the gene as compared to the cDNA sequence recognised by the M13 derived probe.

For the reverse transcription reaction, 100 ng RNA; 500 femtoMoles of each cDNA primer; 1,25 nMol of each dNTP; 200 nMol Tris-HCl pH 8,5; 120 nMol KCl; 20 nMol MgCl2 and 25 nMol Dithiothreitol in a total volume of 4.5 ul was incubated for 1 minutes at 80° C. and 5 minutes at 45° C. To this was added 1.5 ul MMLV-Reverse Transcriptase (Promega, diluted to 40 units/ul). Incubation was for 15 minutes at 37° C. in a thermocycler with heated lid followed by denaturation of the cDNA-RNA hybrids by heating 2 minutes at 98° C.

To the mixture was added 1.5 ul buffer (1500 mM KCl; 300 mM Tris-HCl pH 8.5; 1 mM EDTA) and 4 femtoMol of each probe. Final volume was 9 ul. After 16 hrs. at 60 ° C., 30 ul dilution-buffer (2 mM MgCl2; 1 mM NAD+) and 1 unit Ligase-65 enzyme were added. Ligation is performed for 15 minutes at 60° C. and is followed by a 5 minutes incubation at 98° C. in order to inactivate the ligase-65. 10 ul of the 40 ul mixture was used as a template for a PCR reaction containing 10 pMol of each PCR primer (SeQ ID NO:55 and 85), 50 uM dNTP's and 2.5 units Taq polymerase as described in example 1 except that the PCR primer with SEQ ID 55 was labelled with an IRD-800 moiety.

Separation of amplification products was performed on a LICOR IR2 DNA Analyzer (IRD-800 label; denaturing 25 cm gel containing 6,5% acrylamide) according to the instructions of the manufacturer.

Figure 28:
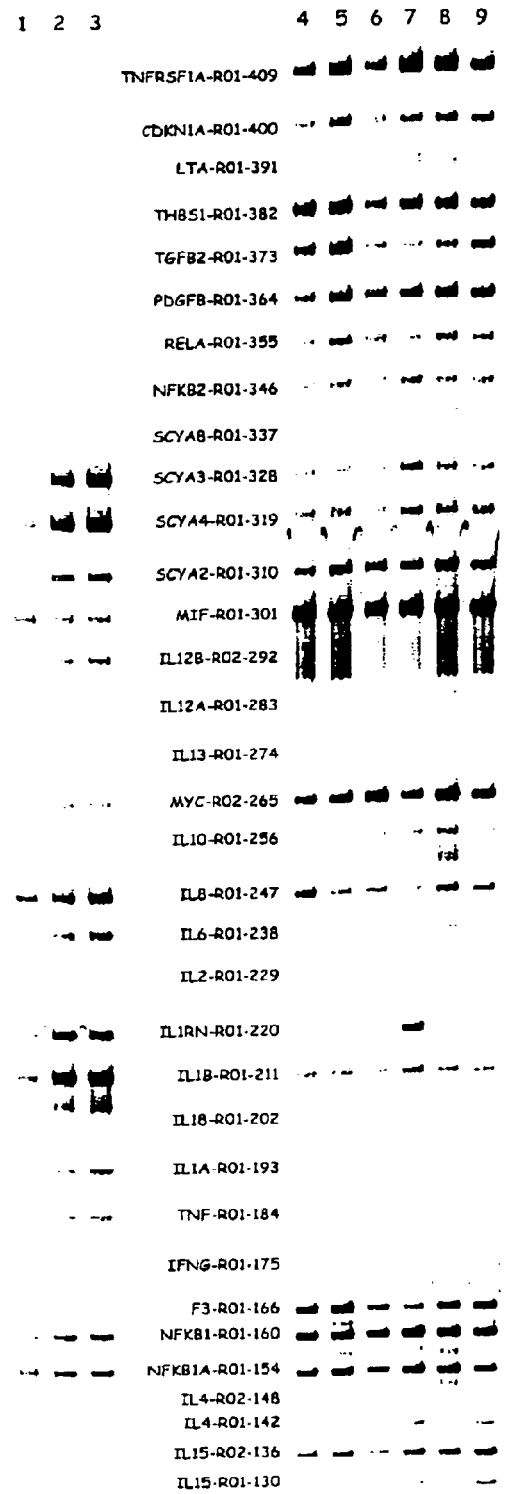
FIG. 28 shows a gel image of probe amplification products obtained upon MLPA analyses of several RNA samples using cDNA specific probes as described in example 14.

Results are shown in FIG. 28. Next to the gel image, a list of the genes (HUGO names) towards which these probes were directed as well as the length of their amplification products is listed.

Lane 1 shows results obtained obtained on total RNA from human blood.

Lane 2 shows results obtained on total RNA from human blood incubated for 4 hrs. in vitro in the presence of 1 nanogram/ml of lipopolysacharids (LPS) in order to stimulate the immune response.

Lane 3 shows results obtained on total RNA from human blood incubated for 4 hrs. in vitro in the presence of 10 nanogram/ml lipopolysacharids (LPS) in order to stimulate the immune response. Several mRNAs known to be over-expressed after such treatments including the Interleukin 8, IL1B, IL1RN, SCYA3 and SCYA4 mRNA's are detected in strongly increased amounts by MLPA analysis in lanes 2 and 3.

As a large amount of labelled primer is used for amplification of a limited number of ligated probe pairs, the amplification products of the other probe pairs are reduced in absolute amounts but may have remained unchanged when compared relative to an internal standard such as a probe for the beta-actin gene. No competitor oligo's were used to decrease the amount of amplification products of some probes in the samples shown. The RNA samples used in lanes 1–3 were a gift from Dr. P. Reitsma of the University of Amsterdam.

Lane 4–9 shows results obtained on 500 ng total RNA each from human salivary gland (Lane 4); human prostate tissue (Lane 5); human pancreatic tissue (Lane 6); human liver tissue (Lane 7); human adrenal gland tissue (Lane 8) and human thyroid gland tissue (Lane 9). These RNA samples were obtained from Clontech Comp.

References:

Vos, P., Hogers, R., Bleeker, M., Reijans, M., Lee, van de T., Hornes, M., Frijters, A., Pot, J., Peleman, J., Kuiper, M., and Zabeau, M. (1995) Nucleic Acid Research 23, 4407–4414.

Welsh, J. et al (1992) Nucleic Acid Research 20, 4965–4970.

Zabeau, M., and Vos, P. (1992) European Patent Application 0534 858 A1.

---

What is claimed is:

1. Method for detecting in a sample, comprising a plurality of sample nucleic acids of different sequence, the presence of at least one specific single stranded target nucleic acid sequence comprising a first and a second segment, and optionally a third segment being located between the first and second segments, the segments located essentially adjacent to one another, comprising, in a reaction mixture, the steps of:
- contacting the sample nucleic acids with a plurality of different probe sets, each probe set comprising
    - a first nucleic acid probe having
        - a first target specific region complementary to the first segment of said target nucleic acid sequence and
        - a first non-complementary region, 3' from the first target specfic region, being essentially non-complementary to said target nucleic acid sequence, comprising a first tag sequence,
    - a second nucleic acid probe having
        - a second target specific region complementary to the second segment of said target nucleic acid sequence and
        - a second non-complementary region, 5' from the second target specific region, being essentially non-complementary to said target nucleic acid sequence, comprising a second tag sequence, and, optionally,
    - a third nucleic acid probe having a third target specific region, complementary to the third segment,
- incubating the plurality of sample nucleic acids with the probes allowing hybridisation of complementary nucleic acids,
- connecting to one another the first, second and optionally the third nucleic acid probes, hybridised to the first, second and, if present, third segment of the same target nucleic acid sequence, respectively, the hybridised probes being located essentially adjacent to one another, forming a connected probe assembly,
- amplifying the connected probe assemblies, wherein amplification is initiated by binding of a first nucleic acid primer specific for the first tag sequence followed by elongation thereof,
    - detecting an amplicon, wherein the amount of at least the first nucleic acid probe of at least one probe set in the mixture is less than 40 femtomoles, and molar ratio between the first nucleic acid primer and the first nucleic acid probe being at least 200.

2. Method according to claim 1, wherein the amount of at least the first nucleic acid probe of each probe set in the mixture is less than 40 femtomoles, and the molar ratio between the nucleic primer and the first nucleic acid probe being at least 200.

3. Method according to claim 1, wherein the molar ratio between the first nucleic acid primer and the first probe of at least one probe set, preferably of each probe set, is at least 400, preferably at least 800, most preferably at least 1600.

4. Method according to claim 1, wherein the molar amount of at least the first nucleic acid probe of at least one probe set, preferably of each probe set is less than 10 femtomoles, preferably 4–5 femtomoles.

5. Method according to claim 1, wherein the first tag sequences of the first nucleic acid probes of the different probe sets are identical.

6. Method according to claim 1, wherein the amplification step comprises binding of a second nucleic acid primer, specific to the second tag sequence, to the elongation product of the first nucleic acid primer.

7. Method according to claim 1, wherein the molar amount of the second nucleic acid probe of at least one probe set, preferably of each probe set, is less than 40 femtomoles, preferably less than 10 femtomoles, most preferably 4–5 femtomoles.

8. Method according to claim 1, wherein the molar ratio between the second nucleic acid primer and the second probe is at least 200, preferably at least 500, more preferably at least 1000, most preferably at least 2000.

9. Method according to claim 1, wherein the second tag sequences of the second nucleic acid probes of the different probe sets are identical.

10. Method according to claim 9, wherein the molar ratio between the second nucleic acid primer and the total amount of probes present in the reaction mixture is at least 5, preferably at least 15 and more preferably at least 25.

11. Method according to claim 1, wherein the reaction mixture comprises at least 10 probe sets, preferably at least 20, most preferably 30–40 different sets of probes.

12. Method according to claim 1, wherein at least a portion of the unhybridised nucleic acid probes remain in the reaction mixture during the incubating step, the connecting step and the amplifying step.

13. Method according to claim 1, wherein all unhybridised probes remain in the reaction mixture during the incubating step, the connecting step and the amplifying step.

14. Method according to claim 1, wherein the contacting step, the connecting step and the amplification step are carried out in the same reaction vessel, the reaction mixture not being removed from the said vessel during the said steps.

15. Method according to claim 1, wherein, in a reaction mixture of 3–150 µl, the amount of:
- sample nucleic acid is 10–1000 ng,
- the first nucleic acid probe of each probe set is 0.5–40 fmol,
- the second nucleic acid probe of each probe set is 0–40 fmol,
- each first nucleic acid primer is 5–20 pmol,
- each second primer is 0–20 pmol.

16. Method according to claim 1, wherein the reaction mixture, at least during the connection step, comprises ligation activity, connecting the essentially adjacent probes.

17. Method according to claim 16, wherein the ligation activity is performed with a thermostable nucleic acid ligase, at least 95% of the activity being inactivated within ten minutes above a temperature of approximately 95° C.

18. Method according to claim 1, wherein at least one nucleic acid probe comprises enzymatic template directed polymerised nucleic acid.

19. Method according to claim 18, wherein at least one nucleic acid probe is generated by digestion of DNA with a restriction endonuclease.

20. Method according to claim 19, wherein the restriction endonuclease cuts at least one strand of the DNA outside the enzyme recognition site sequence on said DNA.

21. Method according to any of the claim 19, wherein the DNA used is single stranded DNA made partially double stranded by annealing of one or more oligonucleotides.

22. Method according to claim 1, wherein at least one nucleic acid probe comprises two separate probe parts being connected together in the step of connecting the essentially adjacent probes.

23. Method according to claim 22, wherein at least one of said probe parts comprises enzymatic template directed polymerised nucleic acid prior to said connecting.

24. Method according to claim 1, further comprising extending a 3' end of a hybridised nucleic acid probe prior to the connecting step.

25. Method according to claim 1, further comprising providing said sample with a competitor nucleic acid comprising a nucleic acid sequence which competes with at least one nucleic acid probe for hybridisation to a target nucleic acid.

26. Method according to claim 1, wherein said sample is further provided with a known amount of a target sequence for one or more probe pairs, prior to the connection step.

27. Method according to claim 1, wherein said sample is further provided with a known amount of one or more connected probes, prior to said amplification.

28. Method according to claim 1, further comprising quantification of the relative or absolute abundance of a target nucleic acid in said sample or sub-sample.

29. Method according to claim 1 for detecting a nucleotide polymorphism, preferably a single nucleotide polymorphism.

30. Method according to claim 1, for the detection of multiple single stranded target nucleic acids.

31. Method according to claim 30, wherein said multiple single stranded target nucleic acids are detected through the detection of multiple amplicons.

32. Method according to claim 31, wherein at least two of said multiple amplicons can be discriminated on the basis of a difference in size of said at least two amplicons.

33. Method according to claim 1, for determining the absolute or relative abundance of multiple single stranded target nucleic acids in the sample.

34. Method according to claim 1 for the detection of a breakpoint region in rearranged nucleic acid.

35. Method for detecting in a sample, comprising a plurality of sample nucleic acids of different sequence, the presence of at least one specific single stranded target nucleic acid sequence comprising a first and a second segment, and optionally a third segment being located between the first and second segments, the segments located essentially adjacent to one another, comprising, in the same reaction vessel, the steps of:

contacting the sample nucleic acids with a plurality of different probe sets, each probe set comprising
a first nucleic acid probe having
a first target specific region complementary to the first segment of said target nucleic acid sequence and
a first non-complementary region, 3' from the first target specific region, being essentially non-complementary to said target nucleic acid sequence, comprising a first tag sequence,
a second nucleic acid probe having
a second target specific region complementary to the second segment of said target nucleic acid sequence and
a second non-complementary region, 5' from the second target specific region, being essentially non-complementary to said target nucleic acid sequence, comprising a second tag sequence, and, optionally,
a third nucleic acid probe having a third target specific region, complementary to the third segment, incubating the plurality of sample nucleic acids with the probes allowing hybridisation of complementary nucleic acids, connecting to one another the first, second and optionally the third nucleic acid probes, hybridised nucleic acid to the first, second and, if present, third segment of the same target nucleic acid sequence, respectively, the hybridised probes being located essentially adjacent to one another, forming a connected probe assembly,
amplifying the connected probe assemblies, wherein amplification is initiated by binding of a first nucleic acid primer specific for the first tag sequence followed by elongation thereof,
detecting an amplicon, wherein at least one nucleic acid probe comprises enzymatic template directed polymerised nucleic acid prior to the hybridisation step.

* * * * *